United States Patent [19]

Mansuri et al.

[11] Patent Number: 5,744,600
[45] Date of Patent: Apr. 28, 1998

[54] PHOSPHONOMETHOXY CARBOCYCLIC NUCLEOSIDES AND NUCLEOTIDES

[75] Inventors: Muzammil M. Mansuri, Cheshire, Conn.; John C. Martin, San Carlos, Calif.; Thomas W. Hudyma, Durham, Conn.; Joanne J. Bronson, Madison, Conn.; Louis M. Ferrara, Meriden, Conn.

[73] Assignees: Institute of Organic Chemistry and Biochemistry of the Academy of Sciences of the Czech Republic, Czech Rep.; Rega Stichting v.z.w., Belgium

[21] Appl. No.: 357,561

[22] Filed: Dec. 16, 1994

Related U.S. Application Data

[63] Continuation of Ser. No. 110,841, Aug. 24, 1993, abandoned, which is a continuation of Ser. No. 785,645, Oct. 31, 1991, abandoned, which is a continuation-in-part of Ser. No. 617,489, Nov. 23, 1990, abandoned, and a continuation of Ser. No. 270,331, Nov. 14, 1988, abandoned.

[51] Int. Cl.$^6$ .................... A61K 31/675; C07F 9/6561; C07D 473/18; C07D 473/34
[52] U.S. Cl. .................... 544/243; 544/229; 544/244; 544/276; 544/277; 544/317; 544/195; 546/23; 548/112
[58] Field of Search .................... 544/243, 244, 544/195; 546/23; 548/112

[56] References Cited

U.S. PATENT DOCUMENTS

| | | | |
|---|---|---|---|
| 4,396,623 | 8/1983 | Shealy et al. | 424/251 |
| 4,605,659 | 8/1986 | Verheyden et al. | 514/262 |
| 4,613,666 | 9/1986 | Fukukawa et al. | 544/277 |
| 4,689,407 | 8/1987 | Morr et al. | 536/27 |
| 4,719,214 | 1/1988 | Shealy et al. | 514/274 |
| 4,730,001 | 3/1988 | Shealy et al. | 514/274 |
| 4,808,716 | 2/1989 | Holy et al. | 544/244 |
| 4,916,224 | 4/1990 | Vince et al. | 544/254 |
| 4,950,758 | 8/1990 | Vince et al. | 544/276 |
| 4,975,434 | 12/1990 | Marquez et al. | 514/274 |
| 5,470,857 | 11/1995 | Borcherding et al. | 514/258 |

FOREIGN PATENT DOCUMENTS

| | | | |
|---|---|---|---|
| 0015584 | 9/1980 | European Pat. Off. | |
| 0236935 | 9/1987 | European Pat. Off. | |
| 0369409 | 5/1990 | European Pat. Off. | |
| 468119 | 1/1992 | European Pat. Off. | 544/244 |
| 2134907 | 8/1984 | United Kingdom | |

OTHER PUBLICATIONS

Orchin, Ed. "Vocabulary of organic chemistry" (Wiley & Sons, 1980) pp. 84,92.
"Webster's 9th New College Dictonary" (Merriam Websters), 1986, pp. 51-70, 822, 853.
Morrison & Boyd "Organic Chemistry, 3rd Edition" (1973), pp. 81-83, 151-154, 250-251.
Streetweison, Jr., "Introduction to Organic Chemistry," 2nd Edition, 1981, pp. 1203-1204.
J Med Chem 28, 1198 (1985), Wood et al.
The Merck Index, 11th Edition, 1989, p. 9287.
Hawley's Condensed Chemical Dictionary, 11th Edition, 1987, p. 1148.
Kinney-Thomas et al, Biochemical Pharmacology, vol. 36, No. 3 (1987), pp. 311-316.
DDI Promising in Clinical Trials, Scrip, Jun. 21, 1989, p. 1422.
Mitsuya et al, Proc. Natl. Acad. Sci., USA 83 (1986), pp. 1911-1915.
Chemical Engineering News, Nov. 23, 1987, pp. 44, 45, 48.
Baba et al, Biochem & Biophys. Res. Comm., vol. 142, No. 1, 1987, pp. 128-134.
Yarchoan et al, The Lancet, Jan. 16, 1988, pp. 76-80.
Hayashi et al., J. Antibiotics 34 675 (1981).
Lim et al., Tet. Lett. 24 5559 (1983).
Trost et al., J.A.C.S. 110 621 (1988).
Kusaka et al. J. Antibiotics 21 255 (1968).
Herdewijn et al., J. Med. Chem. 28 1385 (1985).
Holy et al., Nucl. Acids. Res., Symposium Ser., 14 277 (1984).

(List continued on next page.)

Primary Examiner—Mark L. Berch
Attorney, Agent, or Firm—Mark L. Bosse

[57] ABSTRACT

A compound of the Formula I or Formula II

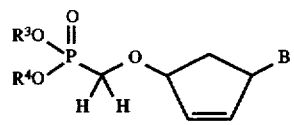

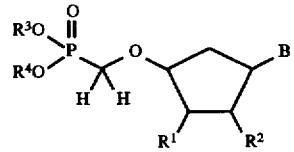

wherein
$R^1$ and $R^2$ are independently hydrogen, hydroxy, chlorine, fluorine, bromine, or an organic substituent having 1 to 5 carbon atoms and selected from acyloxy having a hydrocarbon stem of 1 to 4 carbon atoms, alkoxy, alkylthio, amino, alkylamino and dialkylamino;

$R^3$ and $R^4$ are independently hydrogen, or organic phosphonic ester substituents having 1 to 12 carbon atoms and selected from alkyl, alkenyl, aryl, and aralkyl; and B is a heterocyclic group selected from the group consisting of pyrimidine, purine, triazine, deazapurine, and triazole, attached through a ring nitrogen atom thereof optionally substituted with 1 to 3 substituents selected from the group consisting of hydroxy, mercapto, amino, hydrazino, fluoro, chloro, bromo, iodo, $C_1$ to $C_3$ alkyl, C2–C3 alkenyl, C2–C3 haloalkenyl, C1–C3 alkoxy, and C1–C3 alkylthio;

and the pharmaceutically acceptable acid addition, metal, and amine salts thereof.

The compositions of the invention are useful for, among other things, antiviral agents.

14 Claims, No Drawings

OTHER PUBLICATIONS

Holy et al., *Coll. Czech. Chem. Commun.* 47 3447 (1982).
Rosenberg, *Coll. Czech. Chem. Commun.*, 52 2572 (1987).
Coe et al., *J. Chem. Soc., Chem. Commun.* 312 (1991).
Vince et al., *J. Med. Chem* 33 17 (1990).
Montgomery, *Antiviral Res.* 12 113 (1989).
Borthwick et al., *J. Chem Soc., Chem Commun.* 656 (1988).
Ferrara et al., Presentation (Aug. 28, 1990), ACS Meeting, Washington D.C.
DeClerq, et al., *Nature* (1986) 323 464.
Shealy et al., *J. Heterocyclic Chem.* 13 1041 (1976).
Shealy et al., *J. Heterocyclic Chem.* 18 383 (1981).
Shealy et al., *J. Med. Chem.* 26 156 (1983).

PHOSPHONOMETHOXY CARBOCYCLIC NUCLEOSIDES AND NUCLEOTIDES

CROSS-REFERENCE

This is a continuation of application Ser. No. 08/110,841, filed Aug. 24, 1993, now abandoned, which was a continuation of application Ser. No. 07/785,645, filed Oct. 31, 1991, now abandoned; which was a continuation-in-part of application Ser. No. 07/617,489, filed Nov. 23, 1990, now abandoned; which was a continuation of application Ser. No. 07/270,331, filed Nov. 14, 1988, now abandoned.

SUMMARY OF THE INVENTION

The present invention relates to compounds of Formulae (I) and (II):

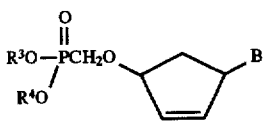

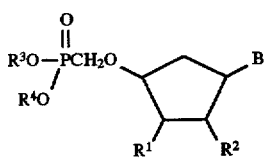

in which $R^1$ and $R^{2'}$ are, independently, selected from H or OH, and substituents preparable therefrom. $R^3$ and $R^4$ are independently selected from H, alkyl, alkenyl, aryl, and aralkyl having up to 12 carbon atoms. B refers to a purine or pyrimidine base of the sort found in the natural nucleosides, attached to the cyclopentane or cyclopentene nucleus through a ring nitrogen atom thereof, and the synthetic analogs of the purine and pyrimidine bases wherein one of the ring nitrogens is replaced with carbon or one or more of the ring carbons is replaced with nitrogen, oxygen, or sulfur. There is at least one ring nitrogen atom. Formulae (I) and (II) are shown in a non-specific representation with respect to stereochemical configuration. The cis stereochemical form, relative to B and the phosphonylmethoxy group in the 4-position, however, is preferred.

The present invention includes processes for producing compounds of Formulae (I) and (II), and certain intermediates useful in these processes.

The invention includes methods for using the compounds to treat viral diseases and diseases of microbial origin in animals or plants, and compositions useful for these purposes. They are also effective against infectious conditions caused by other microorganisms, and against tumors in experimental animals.

Additionally, the compounds of Formula (I) or Formula (II) can exist as enantiomers. The racemic, individual (+)- or (−)-enantiomeric forms, or diastereomeric mixtures of the compounds of Formula (I) or Formula (II) are encompassed by the present invention.

BACKGROUND AND PRIOR ART

The carbocyclic analog of thymidine has been described by Shealy, et al. in *J. Heterocyc. Chem.* 13, 1041–1047 (1976):

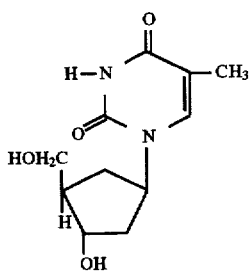

Other references disclosing purine and pyrimidine bases having respectively an $N^9$-, or $N^1$-cyclopentyl substituent of this type are disclosed in the following references:

Shealy, et al., *J. Heterocyc. Chem.* 18, 383–389, (1981).

Shealy, et al., *J. Med. Chem.* 26, 156–161 (1983).

Taniyama, et al., European Specification 236,935, published Sep. 16, 1987.

Shealy, et al., U.S. Pat. No. 4,730,001 patented Mar. 8, 1988.

Shealy, et al., U.S. Pat. No. 4,396,623 patented Aug. 2, 1983.

Shealy, et al., U.S. Pat. No. 4,719,214 patented Jan. 12, 1988.

The foregoing references disclose compounds having antiviral activity.

The neplanocins are antitumor antibiotics in which the ribose unit of a purine nucleoside is replaced by a substituted cyclopentene ring. Five of them have been isolated from *Ampullarilla regularis* A11079 fermentation broths. Their structures have been determined, and they have been synthesized (Hayashi, et al., *J. Antibiot.* 34, 675–680, (1981); Lim, et al., *Tetrahedron Lett.* 24 5559–5562 (1983)).

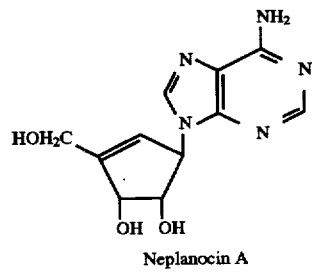

Neplanocin A

Of significance to the present invention is the synthesis of the antibiotic aristeromycin by Trost, et al., *J. Am. Chem. Soc.*, 110, 621–622 (1988), by the following route:

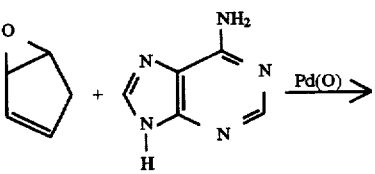

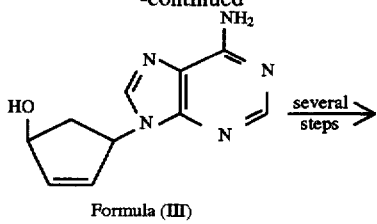

Formula (III)

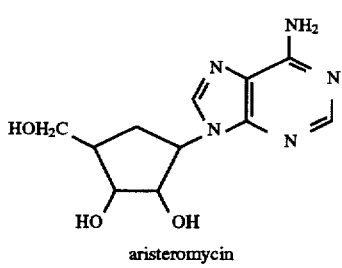

aristeromycin

Aristeromycin is a fermentation product having growth inhibitory activity against phytopathogenic bacteria and fungi (Kusaka, et al., *J. Antibiotics*, (1968), 21, 255). It is cytotoxic, active against murine leukemia L1210 in vitro, and has antiviral activity (Herdewijn, et al., *J. Med. Chem.* (1985), 28, 1385–1386).

A series of 3-heterocyclo-5-hydroxymethylcyclopentanols having strong antiviral activity against Herpes simplex virus 2, strain G is disclosed in U.S. Pat. No. 4,605,659 of Verheyden, et al., patented Aug. 12, 1986.

Another group of antiviral nucleoside compounds is typified by the phosphonomethoxyadenine derivatives typified by (S)-HPMPA which has the following formula (See, Holy, et al., *Nucleic Acids Research*, Symposium Series No. 14, 1984, pages 277–278, and UK specification 2,134,907, published Aug. 22, 1984; DeClercq, et al., *Nature*, (1986), 323 464):

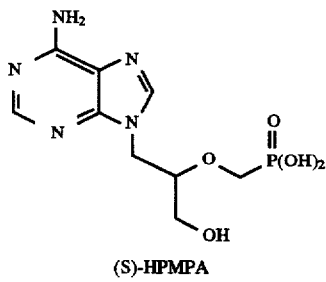

(S)-HPMPA

DETAILED DESCRIPTION OF THE INVENTION

This invention refers to compounds of Formulae (I) and (II), to methods for their synthesis, to the method of treating infections of viral or microbial origin in animals or plants by the administration of these compounds to the host organism, and to compositions useful for the latter purpose.

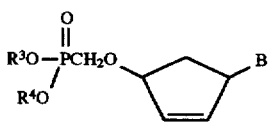

(I)

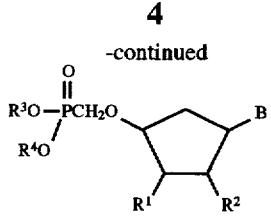

(II)

In Formulae (I) and (II), the symbols B, $R^1$, $R^2$, $R^3$, and $R^4$, have the following meanings: $R^1$ and $R^2$ are, independently, hydrogen, hydroxy, chlorine, fluorine, bromine, amino, or an organic substituent having 1 to 5 carbon atoms and selected from acyloxy, alkoxy, alkylthio, alkylamino, and dialkylamino.

$R^3$ and $R^4$ are, independently, hydrogen, or an organic substituent having 1 to 12 carbon atoms and selected from alkyl, alkenyl, aryl, and aralkyl.

B is a heterocyclic group having at least one nitrogen heteroatom and up to three additional heteroatoms selected from nitrogen, oxygen and sulfur, said heterocyclic group being connected through a nitrogen heteroatom thereof, and the metal and amine salts of those compounds of Formulas (I) and (II) wherein at least one of $R^3$ and $R^4$ is hydrogen.

The preferred heterocyclic groups denoted by B in Formulae (I) and (II) are those purine or pyrimidine bases found in naturally-occurring nucleosides and synthetic analogs thereof. Encompassed by this term are, for example, pyrimidine, xanthine, a substituted xanthine, hypoxanthine, guanine, a substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, a substituted purine, for example, 2-aminopurine, 2,6-diaminopurine, cytosine, a substituted cytosine, for example, 5-ethylcytosine and 5-methylcytosine, thymine, uracil, a 5-substituted uracil, for example, 5-chlorouracil, 5-bromouracil, 5-ethyluracil, 5-iodouracil, 5-propyluracil and 5-vinyluracil, adenine and a substituted adenine, for example, 3-deazaadenine, or an analog of any of these bases wherein a ring nitrogen is replaced with carbon or one or more of the ring carbons is replaced with nitrogen, oxygen, or sulfur, provided that said base contains at least one ring nitrogen atom. Other preferred heterocyclic groups may include, for example, azapurine, triazine, deazapurine, and triazole, said heterocyclic group being substituted with from 1 to 3 substituents independently selected from oxo, hydroxy, amino, fluoro, chloro, bromo, iodo, $C_1$–$C_3$ alkyl, $C_2$–$C_3$ alkenyl, $C_2$–$C_3$ haloalkenyl, $C_1$–$C_3$ alkoxy, and $C_1$–$C_3$ alkylthiol.

Also encompassed by the invention are the racemic, (+)- and (−)-enantiomeric forms, and diastereomeric mixtures of the compounds of Formulae (I) and (II).

The salts alluded to are considered part of the present invention. Those salts which are pharmaceutically acceptable are of particular interest since they are useful in administering the foregoing compounds for medical purposes. Some salts which are not pharmaceutically acceptable are useful in manufacturing processes, for isolation and purification purposes, and in some instances, for use in separating stereoisomeric forms of the compounds of Formulae (I) and (II). The latter is particularly true of amine salts prepared from optically active amines.

Pharmaceutically acceptable metal and amine salts are those salts which are stable under ambient conditions, and wherein the cation does not contribute significantly to the toxicity or biological activity of the salt. Suitable metal salts include the sodium, potassium, calcium, barium, zinc, and aluminium salts. The sodium and potassium salts are preferred. Suitable amine salts are prepared from amines which have sufficient basicity to form a stable salt, and preferably include those amines which are frequently used in medicinal chemistry because of their low toxicity and acceptability for medical use. These include the use of ammonia (for preparing the ammonium salt) and the trialkylamines such as triethylamine, and others including procaine, dibenzylamine, N-benzyl-beta-phenethylamine, ephenamine, and N,N'-dibenzylethylenediamine, dehydroabietylamine, N-ethylpiperidine, benzylamine, and dicyclohexylamine.

Those compounds of Formulae (I) and (II) in which $R^1$ or $R^2$ is a basic function such as the amino, alkylamino, or dialkylamino group or, if such group is present as a substituent on B, $R^1$ or $R^2$ will form acid addition salts. Again, such salts are intended to be included in the present invention. As before, the pharmaceutically acceptable acid addition salts are preferred. They are the acid addition salts in which the anion does not contribute significantly to the toxicity of the salt, and which salts are compatible with the customary pharmaceutical vehicles and adapted for oral or parenteral administration to animals or for application to plants. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, and others.

DOSAGE AND ADMINISTRATION

The present substances have utility as antiviral, antimicrobial, and antitumor agents. Their antiviral properties can be measured and demonstrated by any of a variety of laboratory methods which are available for this purpose. Similarly, utility against plant pathogens and microbial infections caused by bacteria and other microorganisms can be demonstrated by methods which are well known to those skilled in the art. Their antitumor activity can be shown, by established techniques, in animals bearing experimental tumors or in vitro by using various animal and human tumors. The particular spectrum of viruses and microorganisms against which the present substances are active varies from compound to compound. The murine leukemia virus is an example of a retrovirus which is sensitive to the present compounds. A number of disease conditions including AIDS are caused by retroviruses. The test methods for determining anti-viral activity against a variety of viruses, including HIV, are described below.

Pharmaceutical compositions, both veterinary and human, containing the claimed compounds which are appropriate for antiviral use, are prepared by methods and contain excipients which are well known in the art. A generally recognized compendium of such methods and ingredients is *Remington's Pharmaceutical Sciences* by E. W. Martin, (Mark Publ. Co., 15th Ed., 1975).

The compounds of the invention may be administered parenterally (for example, by intravenous, subcutaneous, intraperitoneal, or intramuscular injection), orally, topically, intranasally, or rectally.

The compositions are administered orally or parenterally at dose levels of about 0.1 to 300 mg/kg of compound of Formula (I) or compound of Formula (II), preferably 1.0 to 30 mg/kg of body weight. Unit dosage forms, administered one to five times daily in the amount of 10 to 500 mg per unit dose, are contemplated for man.

For parenteral administration or for administration as drops, as for eye infections, the compounds may be presented in aqueous solution in a concentration of from about 0.1 to 10%, more preferably about 0.1 to 7%. The solution may contain antioxidants, buffers, and other suitable additives.

Alternatively for infections of the eye, or other external tissues, e.g. mouth and skin, the compositions are preferably applied to the infected part of the body of the patient topically as an ointment, cream, aerosol or powder, preferably as an ointment or cream. The compounds may be presented in an ointment, for instance with a water soluble ointment base, or in a cream, for instance with an oil in water cream base, in a concentration of from about 0.01 to 10%.

The compounds of the present invention or compositions containing them are also useful in treating non-human mammals, bird, e.g., chickens and turkeys, and cold-blooded animals, e.g., fish.

Fish which are in a confined area such as a pool, aquarium, or holding tank may also be treated for viral infections such as herpes-like viruses, e.g., channel catfish virus (CCV), herpes-virus salomones, Nerka virus and the like by adding the compound directly to the water of the pool, aquarium, or holding tank or by incorporating the compounds into the feed.

The exact regimen for administration of the compounds and compositions disclosed herein will necessarily be dependent upon the needs of the individual subject being treated, the type of treatment and, of course, the judgment of the attending physician.

PREPARATIVE METHODS

The phosphonic esters of Formula (I) wherein $R^3$ and $R^4$ are as defined, but other than hydrogen, are useful end products and also are key intermediates for the preparation of the other compounds of the present invention. Considering the cyclopentene ring as the central nucleus of these compounds they generally are prepared by either of two sequences. According to the preferred sequence the purine or pyrimidine base substituent B is first introduced to provide a cis-4-hydroxycyclopent-2-en-1-yl derivative of Formula (IV). The cyclopentenol of Formula (IV) is then etherified by treatment with a phosphonylmethylating agent of Formula (V) in which L is a leaving group:

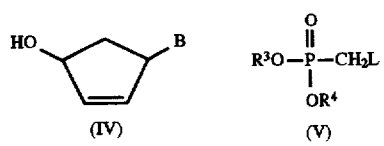

The preferred phosphonylmethylating agents are diethyl phosphonylmethyltrifluoromethane sulfonate or diethyl (p-toluenesulfonyloxymethyl)phosphonate (See, for example, D. P. Phillion et al., *Tetrahedron Letters* (1986), 26, 1477; A. Holy, et al., *Collect. Czech. Chem. Commun.*, (1982), 47, 3447; and Kluge, *Organic Synthesis* (1985), 64 80)).

When operating on a pyrimidine base, the use of protecting groups for the ring nitrogen atom in the 3 position or 4-amino substituent, when present, is sometimes desirable. Whether or not this expedient is required in a given instance is readily determined by the skilled chemist by carrying out trial reactions on a small scale.

Alternatively the phosphonylmethyl ester group may be introduced first to provide a 1,4-disubstituted cyclopent-2-ene of Formula (VI), where L is a leaving group in the trans-configuration. Where, however, L is —OAc, the L and the —OCH₂P(O)(OR³)(OR⁴) moiety of the Formula (VI) compound are in a cis-relationship.

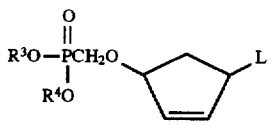

Again, the leaving group L is of a similar nature as with respect to Formula (V) and may include acetoxy, halogen, alkylsulfonate or arylsulfinate.

A useful method for producing the compounds of the present invention involves preparing a compound of Formula (VI), particularly cis-acetoxy-4-(diethylphosphonomethoxy)-cyclopent-2-ene (see Examples ZZ and AAA, below), followed by reacting this product with the desired purine or pyrimidine base. The preparation of the product of Example AAA is outlined below:

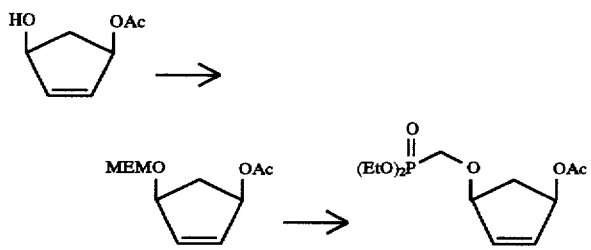

The method of Trost, et al., cited above, *J. Am. Chem. Soc.* (1988), 110, 621–622 involving reaction of adenine with 3,4-epoxycyclopent-2-ene under the control of palladium (0) has proven to be suitable for the preparation of the Formula (IV) intermediates for the preferred sequence outlined above. The reaction proceeds in good yield, and produces the desired 1β,4β-cyclopent-2-ene nucleoside analog regioselectively and stereoselectively. The intermediates of Formula (VI) required for the alternate route may be prepared from 3,4-epoxycyclopent-2-ene which, on reaction with thiophenol in the presence of triethylamine (D. A. Evans, et al., *J. Org. Chem.* (1976), 39, 3178), yields trans-1-hydroxy-2-phenylthiocyclopent-3-ene. This may be etherified with diethoxyphosphonylmethyl trifluoromethanesulfonate as described above. Oxidation of the phenyl sulfide to the sulfoxide and rearrangement and hydrolysis yields the monoetherified trans-cyclopent-2-ene-1,4-diol of Formula (VII):

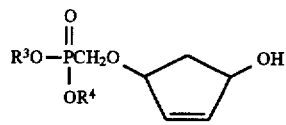

The leaving group L of Formula (VI) is conveniently an alkyl- or arylsulfinate obtained by reaction of the compound of Formula (VII) with phenylsulfinyl chloride (or other arylsulfinyl chloride) or an alkylsulfinyl chloride. The alkylsulfinates or arylsulfinates so produced are then converted to the compounds of Formula (I) by suitable displacement reactions. Those compounds of Formula (VI) wherein L is chlorine can be heated with the sodium salt form of the chosen heterocycle B in the presence of sodium bromide or sodium iodide to yield the desired cis-1,4-substituted products of Formula (I).

According to a further alternate method the monoetherified trans-diol of Formula (VII) may be converted directly to products of Formula (I) by means of a Mitsunobu reaction (O. Mitsunobu, *Synthesis* (1981), p. 1) in which the heterocyclic base B acts as the nucleophile.

The compound of Formula (I) is then transformed into a compound of Formula (II) according to any of a number of well established techniques in organic chemistry. For example, catalytic hydrogenation of a compound of Formula (I) yields a compound of Formula (II) in which $R^1$ and $R^2$ are hydrogen atoms. Another technique that may be used is hydroxylation. Hydroxylation with osmium tetroxide, for example, according to the procedure of Van Rheenan, et al., *Tetrahedron Letters*, 1976, 1973 yields the dihydroxy compound ($R^1$ and $R^2$ are each OH). Hydroboration yields a mixture of monohydroxy compounds which can be separated (one of $R^1$ and $R^2$ is OH and the other is H). Alternatively, the monohydroxy compound can be prepared by reacting a cyclic thiocarbonate ester as outlined in Scheme I:

SCHEME 1

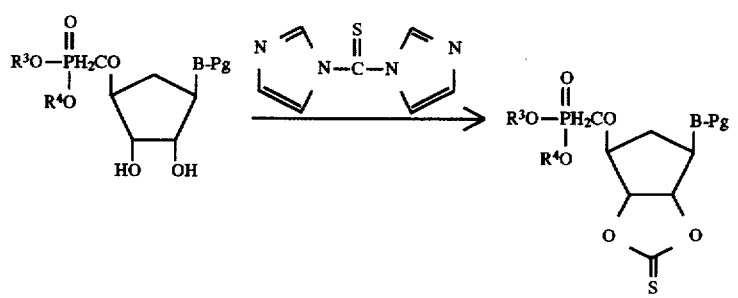

-continued
SCHEME 1

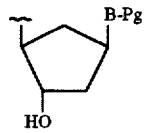

wherein B, R³, and R⁴ are as previously defined and Pg is an optional protecting group. The resulting hydroxy compounds can then be converted to various derivatives of the hydroxyl group such as the acyloxy, alkoxy, alkylthio, halogen, amino, alkylamino and dialkylamino groups by methods available in the art.

The di-esters of Formula (I) and Formula (II) may be hydrolyzed to the corresponding monoesters, wherein one of R³ and R⁴ is a hydrogen atom and the other is an organic phosphonic ester substituent as before. Hydrolysis may be carried out with aqueous sodium hydroxide solution at room temperature to yield the monoester. The dibasic acid of Formula (I) or Formula (II) is prepared by cleavage of the corresponding mono or diester with trimethylsilyl bromide. This reaction is carried out in the absence of water using dimethylformamide or acetonitrile as solvent. Room temperature and protection of the reaction mixture from the atmosphere are preferred conditions.

Of particular interest is the preparation of compounds in which R¹ is hydroxy or hydrogen and R² is fluorine. These compounds can be prepared as outlined in Scheme II:

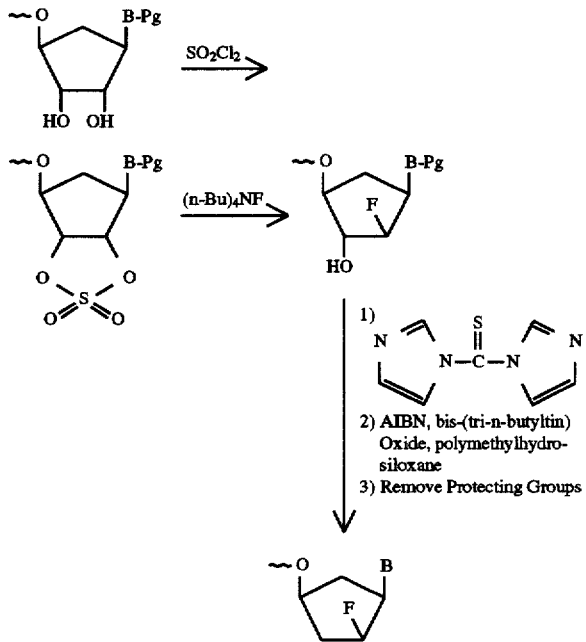

In this Scheme, B and Pg have the same meanings as defined earlier.

As noted earlier, an important starting material for the preparation of the "natural" enantiomeric forms of the Formulae (I) and (II) compounds is (+)-(1R,4S)-cis-1-acetoxy-4-hydroxy-cyclopent-2-ene (See Deardorff et al., *Tet. Lett.* (1986) 27 1255). This compound, or the 4-protected or 4-dialkyl phosphonomethoxy derivative, can be reacted with the desired base in the presence of a palladium (0) compound, such as tetrakis (triphenylphosphine)palladium (0) to prepare the desired intermediate carbonucleoside. This reaction is outlined in Scheme III:

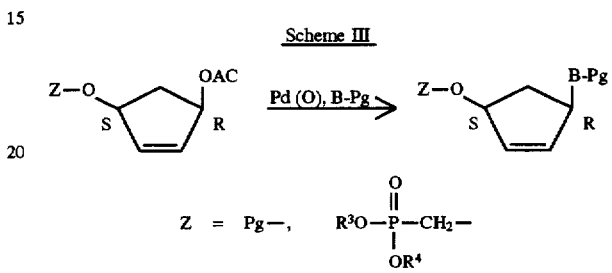

In Scheme III, Pg denotes either hydrogen or a protecting group and B, R³ and R⁴ have the previously described meanings.

Other methods for preparing the compounds of the invention may come to mind to those skilled in the art. These alternate methods are meant to be encompassed within the scope of the present invention. Thus, the following non-limiting examples are provided merely to further illustrate the invention.

DESCRIPTION OF SPECIFIC EMBODIMENTS

Abbreviations Used

THF tetrahydrofuran
SEM-Cl 2-(trimethylsilyl)ethoxymethyl chloride
HPLC high performance liquid chromatography
rt room temperature
HOAc acetic acid
mCPBA m-chloroperbenzoic acid
DMF dimethylformamide
IPA isopropyl alcohol
EtOAc ethyl acetate

EXAMPLE A (±)-9-(4-β-Hydroxycyclopent-2-ene-1-β-yl)adenine

A solution of 3,4-epoxycyclopentene (194 mg, 2.36 mmol) in DMF (1.5 mL) was added dropwise over two mins to a stirred mixture of adenine (319 mg, 2.36 mmol) and tetrakis(triphenylphosphine)palladium (0) (137 mg, 0.118 mmol) in DMF (5 mL) and THF (2 mL) at 22° C. under argon. There was a mild exotherm after which the reaction was stirred for 1 hr. at ambient temperatures and then for 2 hrs at an oil bath temperature of 80°–90° C. The mixture was then poured into warm water and filtered. After an additional filtration through a 0.45 μm nylon membrane filter the filtrate was pumped onto a Michel-Miller (310×25 mm) column which packed with Partisil Prep 40TM ODS-3. The column was eluted with 0.025M of pH 5 ammonium phosphate buffer containing 4–10% $CH_3CN$. The progress of elution was monitored with a refractive index detector and the appropriate fractions were combined. The pH of the combined eluates was adjusted to 7.06 with dilute NaOH. The resulting solution was concentrated and the residue was dissolved in $H_2O$ (20 mL). The solution was applied to the Michel-Miller column and the column eluted with $H_2O$ (200 mL) to remove the inorganic salts. Elution with $H_2O$-10% $CH_3CN$ afforded the title compound, which was isolated as a colorless powder (170 mg, 33%) after removal of the $CH_3CN$ followed by lyophilization of the resulting aqueous solution. Analysis; $C_{10}H_{11}N_5O \cdot 0.25H_2O$: (calc'd): C: 54.17, H: 5.02, N: 31.59, $H_2O$, 2.03; (found): C: 54.12, H: 5.27, N: 31.07, $H_2O$, 1.77. $^1H$ NMR (360 MHz, $D_2O$) δ 8.03 (s, 1H), 8.00 (s, 1H), 6.25 (m, 1H), 6.06 (m, 1H), 5.36 (m, 1H), 4.85 (m, 1H under HDO resonance), 3.01 (m, 1H), 1.71 (m, 1H).

EXAMPLE B (±)-1-(4-β-Hydroxycyclopent-2-ene-1-β-yl)thymine

A solution of 3,4-epoxycyclopentene (361 mg, 4.39 mmol) in DMF (1 mL) was rapidly added to a stirred, deoxygenated mixture of thymine (462 mg, 3.66 mmol) and tetrakis(triphenylphosphine)palladium (0) (212 mg, 0.183 mmol) in a mixture of DMF (5 mL) and THF (2 mL) at 22° C. under argon. The reaction mixture was then stirred at 90° C. for 1 hr. The mixture was cooled and filtered. The filtrate was diluted with $H_2O$ and concentrated to a volume of about 20 mL. The hazy solution was refiltered (0.45 μm membrane) and chromatographed and desalted on the Michel-Miller $C_{18}$ column as described in the previous example to provide an aqueous solution of the title compound. The solution was concentrated on a rotary evaporator to a volume of about 5 mL, whereupon colorless crystals (121 mg, 16%) of the analytical sample were formed. m.p. 197°–198° C.

Analysis: $C_{10}H_{12}N_2O_3$ (calc'd): C: 57.69, H: 5.81, N: 13.45; (found): C: 57.39, H: 5.90, N: 13.38. $^1H$ NMR (360 MHz, $D_2O$) δ 7.38 (s, 1H), 6.20 (m, 1H), 5.88 (m, 1H), 5.41 (m, 1H), 4.83 (m, 1H), 2.94 (m, 1H), 1.84 (s, 3H), 1.45 (m, 1H).

(±)-1-(4-β-Hydroxycyclopent-2-ene-1-β-yl)thymine was isolated in a comparable yield when the tetrakis (triphenylphosphine)palladium (0) catalyst was replaced with $Pd[P(i-OC_3H_7)_3]_4$ as the palladium (0) catalyst in the above experiment.

The isolated yield of (±)-1-(4-β-Hydroxy-2-cyclopenten-1-β-yl)thymine was 36% when a solution of 3,4-epoxycyclopentene (4.61 g, 56.1 mmol) in DMF (7 mL) was added dropwise over 40 minutes to a stirred, deoxygenated mixture of thymine (4.4 g, 34.6 mmol) and tetrakis (triphenylphosine)palladium (0) (2.0 g, 1.73 mmol) in DMF (60 mL) at an oil bath temperature of 90° C. Stirring was continued at 90° C. for 3.25 hrs and the title compound isolated and purified by chromatography on a Michel-Miller column (40×350 mm) as previously described.

EXAMPLE C (±)-1-(4-β-Hydroxycyclopent-2-ene-1-β-yl)cytosine

A solution of 3,4-epoxycyclopentene (272 mg, 3.31 mmol) in DMF (1 mL) was rapidly added to a stirred, deoxygenated mixture of cytosine (307 mg, 2.76 mmol) and tetrakis(triphenylphosphine)palladium (0) (160 mg, 0.138 mmol) in THF (2 mL) and DMF (5 mL) at 22° C. An immediate mild exothermic reaction ensued. The reaction mixture was stirred for 72 hrs at ambient temperature. The mixture was filtered and the filtrate was diluted with $H_2O$. The hazy filtrate was refiltered (0.45 mm nylon membrane) and the clarified solution pumped onto the Michel-Miller (310×25 mm) $C_{18}$ column. The column was eluted with 0.025 M of pH 4.8 ammonium phosphate buffer containing 5% $CH_3CN$, and the progress of elution monitored by differential refractometry. The pH of the appropriately combined eluates was adjusted to 7.2 with dilute $NH_4OH$. The volume of the combined eluates was reduced to about 4 mL on a rotary evaporator. The solution was applied to the Michel-Miller $C_{18}$ column. The column was eluted with $H_2O$ to remove the inorganic material and then with $H_2O$-10% $CH_3CN$ to elute the title compound as a colorless solid (54 mg, 10.1%) which was isolated by lyophilization. Analysis: $C_9H_{11}N_3O_2$ (calc'd): C: 55.98, H: 5.74, N: 21.75; (found): C: 55.25, H: 5.87, N: 21.48. $^1H$ NMR (360 MHz, $D_2O$) δ 7.53 (d, 1H), 6.20 (m, 1H), 6.00 (d,1H), 5.90 (m, 1H), 5.41 (m, 1H), 4.79 (m, 1H under HDO resonance), 2.96 (m, 1H), 1.41 (m, 1H).

In an improved procedure, (±)-1-(4-β-hydroxycyclopent-2-ene-1-β-yl)cytosine was isolated in a lyophilized yield of 54% when a solution of 3,4-epoxycyclopentene (790 mg, 9.62 mmol) in DMF (1.5 mL) was added dropwise over 1.25 hrs to a stirred, deoxygenated mixture of cytosine (754 mg, 6.78mmol), tetrakis(triphenylphosphine)palladium (0) (413 mg, 0.357 mmol) and triphenylphosphine (187 mg, 0.714 mmol) in DMF (15 mL) at 22° C. The mixture was then stirred at 22° C. for 0.66 hrs, 50° C. for 0.6 hrs and then at 80° C. for 0.25 hrs, the title compound was isolated as described above.

EXAMPLE D (±)-1-(4-β-Hydroxycyclopent-2-ene-1-β-yl)-$N^3$-(2-(trimethylsilyl)ethoxymethyl)thymine Method 1

A mineral oil dispersion of 50% NaH (18 mg, 0.378 mmol) was added to a stirred mixture of (±)-1-(4-β-hydroxycyclopent-2-ene-1-β-yl)thymine (75 mg, 0.36 mmol) in DMF (0.5 mL) at 22° C. After the rapid evolution of hydrogen subsided, the mixture was stirred at 60° C. for 5 mins to complete salt formation. The mixture was cooled in a $IPA/CO_2$ bath to −40° C. to −30° C., a solution of 2-(trimethylsilyl)ethoxymethyl chloride ("SEM-Cl") (61 mg, 0.36 mmol) in DMF (0.5 mL) was then added dropwise over 8 mins. Stirring was continued with cooling for 0.25 hrs and then at 22° C. for 0.66 hrs. The mixture was concentrated and the residue partitioned between EtOAc and $H_2O$. The EtOAc layer was washed ($H_2O$, brine), dried ($Na_2SO_4$) and concentrated. The residue was chromatographed on $SiO_2$ (10 g) with $CH_2Cl_2$-acetone (20:3) to afford the title compound (65 mg, 53% yield) as a viscous oil with an estimated purity of 93.4% by HPLC. HPLC: retention time, 5.88 mins (Waters $C_{18}$ radial pak cartridge) flow rate 2 mL/min of 45% pump A (90% $H_2O$-10% $CH_3CN$), 55% pump B (20% $H_2O$-80% $CH_3CN$). Detection at 254 nm. $^1H$ NMR (200 MHz, $CDCl_3$) δ 7.16 (s, 1H), 6.20 (m, 1H), 5.82 (m, 1H), 5.52 (m, 1H), 5.41 (s, 2H), 4.86 (m, 1H), 3.69 (m, 2H), 2.90 (m, 1H), 2.70 (br s, 1H), 1.92 (s, 3H), 1.61 (m, 1H), 0.98 (m, 2H), 0.02 (s, 9H).

Method 2

A solution of (±)-1-(4-β-acetoxycyclopent-2-en-1-β-yl)-$N^3$-(2-(trimethylsilyl)ethoxymethyl)thymine (Example E, 2.26 g, 5.94 mmol) in $CH_3OH$ (75 mL) was saturated with $NH_3$ at 10° C. The solution was allowed to stand for 20 hrs at ambient temperatures and then was concentrated. The residue was partitioned between Et$_2$O and H$_2$O. The ethereal layer was washed with H$_2$O, followed by brine and then dried over Na$_2$SO$_4$. Removal of the ether afforded the title compound (2.0 g, 99.5%) which was identical to that prepared in Method 1.

EXAMPLE E (±)-1-(4-β-Acetoxycyclopent-2-ene-1-β-yl)-N$^3$-(2-(trimethylsilyl)ethoxymethyl)thymine and (±)-1-(4-β-Hydroxycyclopent-2-ene-1-β-yl)-N$^3$-(2-(trimethylsilyl)ethoxymethyl)thymine A mineral oil dispersion of 50% NaH (0.608 g, 12.7 mmol) was added to a cooled (ice/H$_2$O bath), stirred mixture of (±)-1-(4-β-hydroxycyclopent-2-ene-1-β-yl)thymine (2.51 g, 12.1 mmol) in DMF (17 mL) under argon. The cooling bath was removed after the vigorous evolution of hydrogen subsided and stirring was continued at ambient temperatures for 0.25 hrs, and then for an additional 0.25 hrs at 50° C. on a steam bath. The stirred mixture was cooled in a IPA/CO$_2$ bath which was maintained at −40° C. A solution of SEM-Cl (2.01 g, 12.1 mmol) in DMF (17 mL) was added dropwise during 5 mins. Stirring was continued with cooling for 0.25 hrs at −40° C. and then 0.5 hrs at ambient temperatures. The mixture was concentrated and the residue partitioned between EtOAc and H$_2$O. The EtOAc layer was washed (H$_2$O, brine), dried (Na$_2$SO$_4$) and concentrated. The residue was flash chromatographed on SiO$_2$ (150 g) with CH$_2$Cl$_2$-acetone (100:15) to provide (±)-1-(4-β-hydroxycyclopent-2-ene-1-β-yl)-N$^3$-(2-(trimethylsilyl)ethoxymethyl)thymine (790 mg, 19% yield) as a viscous oil and (±)-1-(4-β-acetoxycyclopen-2-ene-1-β-yl)-N$^3$-(2-(trimethylsilyl)ethoxymethyl)thymine (3.1 g, 68%). Recrystallization of the latter compound from hexane afforded colorless crystals of the analytical sample. m.p. 65°–66° C.

Analysis C$_{18}$H$_{28}$N$_2$O$_5$Si (calc'd): C: 56.82, H: 7.42, N: 7.37; (found): C: 56.59, H: 7.42, N; 7.29.

$^1$H NMR (200 MHz, CDCl$_3$) δ 7.00 (s, 1H), 6.23 (m, 1H) 5.93 (m, 1H), 5.70 (m, 2H), 5.38 (s, 2H), 3.70 (m, 2H), 3.00 m, 1H), 2.09 (s, 3H), 1.94 (s, 3H), 1.65 (m, 1H), 0.99 (m, 2H), 0.01 (s, 9H).

EXAMPLE F (±)-1-(4-β-Diethylphosphonylmethoxycyclopent-2-ene-1-β-yl)-N$^3$-(2-(trimethylsilyl)ethoxymethyl) thymine Method 1

A mineral oil dispersion of 50% NaH (10.4 mg, 0.217 mmol) was added to a stirred solution of (±)-1-(4-β-hydroxycyclopent-2-ene-1-β-yl)-N$^3$-(2-(trimethylsilyl) ethoxymethyl)thymine (70 mg, 0.207 mmol) in DMF (0.5 mL) at 22° C. Stirring was continued for 0.5 hrs at 22° C. and then for 0.25 hrs at 60° C. The solution was cooled in an IPA/CO$_2$ bath maintained at −40° C. when a solution of diethyl phosphonomethyltrifluoromethane sulfonate (68.3 mg, 0.23 mmol) in DMF (0.5 mL) was added dropwise over 4 mins. Stirring was continued with cooling for 0.25 hrs and then at ambient temperature for 0.66 hrs. The mixture was concentrated and the residue partitioned between EtOAc and H$_2$O. The ethyl acetate layer was washed (H$_2$O, brine), dried (Na$_2$SO$_4$) and concentrated to leave a brown oil. The oil was chromatographed on SiO$_2$ (10 g) with CH$_2$Cl$_2$-acetone (200:25) to afford the title compound (25 mg, 25%) as a viscous oil, with an estimated purity of 92% (HPLC). HPLC: retention time, 10.47 minutes (Waters C$_{18}$ radial pak cartridge) flow rate 2 mL/min; 45% pump A (90% H$_2$O-10% CH$_3$CN), 55% pump B (20% H$_2$O-80% CH$_3$CN). Detection at 254 nm.

$^1$H NMR (200 MHz, CDCl$_3$) δ 7.19 (s, 1H), 6.19 (m, 1H), 5.95 (m, 1H), 5.76 (m, 1H), 5.48 (s, 2H), 4.65 (m, 1H), 4.23 (m, 4H), 3.92 (m, 2H), 3.76 (m, 2H), 2.92 (m, 1H), 1.99 (s, 3H), 1.74 (m, 1H), 1.45 (m, 6H), 1.07 (m, 2H), 0.06 (s, 9H).

Method 2

A solution of 2.5M n-BuLi in hexane (2.7 mL, 6.75 mmol) was added dropwise to a cooled (CO$_2$/acetone bath) stirred solution of (±)-1-(4-β-hydroxycyclopent-2-ene-1-β-yl)-N$^3$-(2-(trimethylsilyl)ethoxymethyl)thymine (1.9 g, 5.61 mmol) in THF (15 mL) under argon. A solution of diethyl phosphonylmethyltrifluoromethane sulfonate (2.53 g, 8.41 mmol) in THF (2 mL) was added dropwise over 1 min. The reaction was stirred at approximately −70° C. for 0.25 hrs and then the solution was allowed to warm to 22° C. The solution was cooled in an ice/salt bath mixture and stirred for a further 0.25 hrs. Saturated aqueous NH$_4$Cl was added and the THF removed in vacuo. The aqueous mixture was extracted with EtOAc and the organic layer sequentially washed (dilute aqueous NaHCO$_3$, H$_2$O, brine) and dried (Na$_2$SO$_4$). Removal of the EtOAc left a brown oil (3 g) which was flash chromatographed on SiO$_2$ (120 g) with CH$_2$Cl$_2$-acetone (10:1) to afford an initial fraction (877 mg) containing the title compound with an estimated purity of 88% by HPLC and an additional fraction of 494 mg containing the title compound with an estimated purity of 73% by HPLC. The major contaminant was the starting alcohol.

EXAMPLE G (±)-1-(4-β-Phosphonylmethoxycyclopent-2-ene-1-β-yl)-N$^3$-(2-(trimethylsilyl)ethoxymethyl)thymine Bromotrimethylsilane (1.3 mL, 9.67 mmol) was added dropwise over 1 min to a stirred solution of (±)-1-(4-β-diethylphosphonylinethoxycyclopent-2-ene-1-β-yl)-N$^3$-(2-(trimethylsilyl)ethoxyethyl)thymine (315 mg, 0.645 mmol) in DMF (5 mL) at 22° C. and under argon. The solution was stirred at ambient temperature for 4 hrs and then was concentrated to dryness in vacuo. The residual brown oil was dissolved in DMF (5 mL) and the solution reconcentrated. A solution of the residue in H$_2$O was applied to the Michel-Miller C$_{18}$ column. The column was eluted with H$_2$O containing from 10 to 40% of CH$_3$CN. The appropriate eluates were combined and concentrated to leave the title compound (144 mg, 74%) as a viscous glass. $^1$H NMR (200 MHz, CDCl$_3$) δ 7.20 (s, 1H), 6.23 (m, 1H), 5.93 (m, 1H), 5.66 (m, 1H), 5.41 (s, 2H), 4.59 (m, 1H), 3.85 (m, 2H),3.73 (m, 2H), 2.80 (m, 1H), 1.93 (s, 3H), 1.78 (m, 1H), 1.00 (m, 2H), 0.02 (s, 9H).

EXAMPLE H (±)-1-(4-β-Phosphonylmethoxycyclopent-2-ene-1-β-yl)thymine and (±)-1-(4-β-phosphonylmethoxycyclopent-2-ene-1-β-yl)-N$^3$-(hydroxymethyl)thymine Bromotrimethylsilane (2.0 mL) was added dropwise to a stirred solution of (±)-1-(4-β-diethylphosphonomethoxycyclopent-2-ene-1-β-yl)-N$^3$-(2-(trimethylsilyl)ethoxymethyl)thymine (494 mg, estimated purity of 73%) in DMF (5 mL) at 22° C. and under argon. The solution was stirred for 0.25 hrs and then was concentrated to dryness. The residue was dissolved in a mixture of EtOH (18 mL) and 1N HCl (18 mL). The mixture was stirred at an oil bath temperature of 55° C. for 0.75 hrs and then was heated to reflux for 1 hr. The solution was concentrated and the residue dissolved in H$_2$O. The aqueous solution was washed with ether and concentrated. The concentrate was applied to the Michel-Miller $C_{18}$ column. The column was eluted with $H_2O$ containing 3% $CH_3CN$. Two groups of eluates were combined and the $CH_3CN$ removed by concentration in vacuo. Removal of the $H_2O$ from each group by lyophilization provided (±)-1-(4-β-phosphonomethoxycyclopent-2-ene-1-β-yl)thymine as a colorless solid (25 mg) [HPLC: retention time, 6.93 mins (Waters $C_{18}$ radial pak cartridge) flow rate 2 mL/min 95% pump A (0.05M of pH 4.3 ammonium phosphate buffer), 5% pump B (20% $H_2O$-80% $CH_3CN$). Detection at 254 nm.

$^1H$ NMR (360 MHz, DMSO-$d_6$) δ 11.25 (s, 1H), 7.20 (s,1H), 6.32 (m,1H), 5.94 (m, 1H),5.42 (m, 1H), 4.51 (m, 1H), 3.59 (m, 1H), 2.66 (m, 1H), 1.74 (s, 3H), 1.58 (m, 1H)]; and, a mixture of the foregoing and (±)-1-(4-β-phosphonylmethoxycyclopent-2-ene-1-β-yl)-$N^3$-(hydroxymethyl)thymine (25.8 mg). HPLC: retention time 11.06 min containing 33% of the fully deprotected thymine derivative. The pH of an aqueous solution of this latter mixture was raised to 12, which removed the $N^3$-hydroxymethyl group.

EXAMPLE I (±)-1-(4-β-phosphonomethoxycyclopent-2-ene-1-β-yl)thymine

Bromotrimethylsilane (3.6 mL) was added dropwise to a stirred solution of (±)-1-(4-β-diethylphosphonomethoxycyclopent-2-ene-1-β-yl)-$N^3$-2-(trimethylsilyl)ethoxymethylthymine (860 mg) in DMF (10 mL) at 22° C. and under argon. The solution was stirred for 2.5 hrs and concentrated. The residue was diluted with DMF and reconcentrated. A mixture of the residue in EtOH (25 mL) and 1N HCl (25 mL) was heated to reflux for 1.5 hrs. The mixture was concentrated to dryness and the residue dissolved in $H_2O$ (5 mL). The pH of the solution was raised to 12.8 by the addition of 1N NaOH. After several minutes the pH was lowered to 2.2 by the addition of 85% $H_3PO_4$. The solution was applied to the Michel-Miller $C_{18}$ column. The column was eluted with a mixture of $H_2O$—$CH_3CN$—HOAc (1000:40:3). The appropriate fractions were combined as determined by HPLC and concentrated to dryness. The residue was dissolved in $H_2O$ and the aqueous solution concentrated by lyophilization to afford the title compound as a colorless lyophilate. This lyophilate was combined with several others from previous small scale experiments and the combination recrystallized from $H_2O$ (1 mL) to afford colorless crystals of the title compound (56 mg). m.p. 116°–118° C.

Analysis: $C_{11}H_{15}N_2O_6P.H_2O$ (calc'd): C: 41.26, H: 5.35, N: 8.74; (found): C: 41.36, H: 5.03, N: 8.85.

EXAMPLE J (+)-1-(4-β-Hydroxycyclopent-2-ene-1-β-yl)-$N^4$-(dimethylaminomethylidene)cytosine N,N-Dimethylformamide dimethyl acetal (361 μL, 2.72 mmol) was added to a stirred mixture of (±)-1-(4-β-hydroxycyclopent-2-ene-1-β-yl)cytosine (500 mg, 2.59 mmol) in DMF (10 mL). The reaction was then heated for 1.5 hrs at an oil bath temperature of 70°–80° C., during which time solution occurred. The solution was concentrated and the residual solid crystallized from $CH_2Cl_2$ with the addition of ether to provide peach crystals of the title compound (580 mg, 90%). m.p. 180°–181° C. Analysis: $C_{12}H_{16}N_4O_2$ (calc'd): C: 58.06, H: 6.50, N: 22.57; (found): C: 57.62, H: 6.47, N: 22.18. $^1H$ NMR (200 MHz, DMSO-$d_6$) δ 8.63 (s, 1H), 7.63 (d, 1H), 6.15 (m, 1H), 6.00 (d, 1H), 5.80 (m, 1H), 5.50 (m, 1H), 5.25(m, 1H, exchangeable), 4.69 (m, 1H), 3.19 (s, 3H), 3.03 (s, 3H), 2.96 (m, 1H), 1.35 (m, 1H).

EXAMPLE K (+)-1-(4-β-Diethylphosphonomethoxycyclopent-2-ene-1-β-yl)-$N^4$-(dimethylaminomethylidene)cytosine A solution of 2.5M n-BuLi in hexane (0.8 mL, 2.01 mmol) was added dropwise to a stirred mixture of (±)-1-(4-β-hydroxycyclopent-2-ene-1-β-yl)-$N^4$-(dimethylaminomethylidene)cytosine (500 mg, 2.01 mmol) in HMPT (3 mL) and THF (4 mL) which was cooled in a IPA/$CO_2$ bath maintained at −40° C. to −30° C. Stirring was continued at −40° C. to −20° C. for 0.5 hrs. The solution was then cooled to −40° C. when a solution of diethylphosphonomethyltrifluoromethane sulfonate (755 mg, 2.52 mmol) in THF (2 mL) was added dropwise. The solution was allowed to warm to 22° C. during 1.5 hrs and was quenched by the addition of saturated aqueous $NH_4Cl$ (1 mL). The mixture was concentrated and the concentrate, which contained residual HMPT, was flash column chromatographed. The column was sequentially eluted with $CH_2Cl_2$ (200 mL) and then with $CH_2Cl_2$ containing 10% MeOH to afford the title compound (1.1 g) as a gum, with an estimated purity of 90.6% by HPLC. HPLC: retention time 4.87 mins (Waters $C_{18}$ radial pak cartridge); flow rate 2 mL/min. of 75% pump A (0.05M of pH 5 ammonium phosphate buffer), 25% pump B (20% $H_2O$-80% $CH_3CN$).

EXAMPLE L (±)-1-(4-β-Phosphonomethoxycyclopent-2-ene-1-β-yl)cytosine

Bromotrimethylsilane (1.7 mL, 12.6 mmol) was added to a stirred solution of (±)-1-(4-β-diethylphosphonomethoxycyclopent-2-ene-1-β-yl)-$N^4$-(dimethylaminomethylidene)cytosine (1 g, 2.51 mmol) in DMF (5 mL) at 22° C. The reaction was stirred for two hours and then concentrated to dryness. A solution of residue in $H_2O$ was applied to the Michel-Miller $C_{18}$ column. The column was eluted with 0.025 M of pH 5 ammonium phosphate buffer containing 2% $CH_3CN$. The appropriate eluates were combined and the $CH_3CN$ removed in vacuo. The aqueous solution was lyophilized and the residual solid was dissolved in water and the solution applied to the Michel-Miller $C_{18}$ column. The column was eluted with $H_2O$ to remove the inorganic salts. Elution with $H_2O$ containing 20% $CH_3CN$ provided the title compound (166 mg, 23%) as a colorless lyophilate with an estimated purity of >99% by HPLC. HPLC: retention time, 5.49 mins (Waters $C_{18}$ radial pak cartridge); flow rate 2 mL/min of 98% pump A (0.05M of pH 5 ammonium phosphate buffer), 2% pump B (20% $H_2O$-80% $CH_3CN$). Detection at 254 nm. Crystallization from $H_2O$-EtOH provided the analytical sample. m.p. 238°–240° C. (decomp). Analysis $C_{10}H_{14}N_3O_5P$ (calc'd): C: 41.83, H: 4.92, N: 14.64; (found): C: 41.19, H: 4.95, N: 14.52.

$^1H$ NMR (360 MHz, DMSO-$d_6$) δ 7.35 (d, 1H), 6.27 (d, 1H), 5.91 (d, 1H), 5.69 (d, 1H), 5.50 (m, 1H), 4.52 (m, 1H), 3.56 (d, 2H), 2.67 (m, 1H), 1.44 (m, 1H).

EXAMPLE M (±)-1-(4-β-Phosphonomethoxycyclopentane-1-β-yl)cytosine

A mixture of (±)-1-(4-β-phosphonomethoxycyclopent-2-ene-1-β-yl)cytosine (20 mg) and 10% palladium on carbon (15 mg) in H$_2$O (50 mL) was shaken with hydrogen at 50 p.s.i. for 0.25 hrs. The solution was filtered and the filtrate concentrated by lyophilization to afford the title compound as a colorless solid with an estimated purity of 94% by HPLC. HPLC: retention time, 12.22 mins (Waters C$_{18}$ radial pak cartridge); flow rate 1 mL/min. of 98% pump A (0.05M of pH 5 ammonium phosphate buffer), 2% pump B (80% CH$_3$CN-20% H$_2$O).

$^1$H NMR (360 MHz, D$_2$O) δ 8.03 (d, 1H), 6.09 (d, 1H), 5.02 (m, 1H), 4.08 (m, 1H), 3.56 (m, 2H), 2.32 (m, 1H), 2.15 (m, 1H), 2.00 (m, 1H), 1.75 (s, 3H).

EXAMPLE N

Trans-cyclopent-2-ene-1,4-diol

Trans-2-phenylthio-3-cyclopenten-1-ol(1.21 g, 6.3 mmol) was dissolved in CH$_2$Cl$_2$ (8 mL) and cooled to 0° C. in an ice bath under nitrogen. meta-Chloro-perbenzoic acid (1 g, 5.9 mmol) was added in small batches. An exothermic reaction occurred. The reaction mixture was left to stir at room temperature for 3 hrs, and then filtered and concentrated to give the sulfoxide trans-2-phenylsulfinyl-3-cyclopenten-1-ol as a pale yellow solid. The sulphoxide was used directly without further purification. The sulphoxide was dissolved in methanol (5 mL) and trimethyl phosphite (1.17 g, 9.4 mmol) and the reaction mixture heated to reflux overnight under nitrogen. The reaction mixture was concentrated and then flash chromatographed to give the trans diol as a colorless oil. (240 mg, 40% overall). $^1$H NMR (360 MHz, CDCl$_3$) δ 6.05 (m, 2H, CH=CH), 5.0 (m, 2H, CHO), 2.1 (m, 2H, CH$_2$). $^{13}$C NMR (50 MHz, CDCl$_3$) 137.20 (CH=CH), 76.99 (CHOH), 44.28 (CH$_2$).

EXAMPLE O

Trans-1-diethylphosphonomethoxy-2-(phenylthio)-cyclopent-3-ene

Sodium hydride (60%) (460 mg; 11.5 mmol) was added to a dry three neck 100 ml round bottom flask equipped with a nitrogen inlet and magnetic stirrer. The hydride was washed with hexane (2×25 mL) and ether (2×25 mL), and the solvent removed by syringe after each washing. After the last wash the last traces of ether were removed on the pump. THF (10 mL) was added to the sodium hydride and the suspension was cooled in a ice-salt bath under a nitrogen atmosphere. Trans-2-phenylthiocyclopent-3-en-1-ol (2 g, 10.5 mmol) in THF (5 mL) was then added dropwise over 5 mins; hydrogen evolution was observed. Once all the alcohol had been added, the reaction mixture was left to stir at 0° C. for 1 hr. and at ambient temperature for 1 hr. The reaction mixture became very dark in color during this time. The reaction mixture was then cooled in a ice-salt bath again and a solution of trifluoromethanesulphonyloxymethyldiethylphosphonate (3.43 g, 11.4 mmol) in THF (10 mL) was slowly added dropwise. After addition, the reaction mixture was stirred at 0° C. for 1 hr. A further 0.5 equivalents of triflate in THF were added and the reaction mixture then allowed to stir at ambient temperature for 0.5 hr. Methanol (3 mL) was added followed by ethyl acetate (50 mL). The organic phase was washed with brine, dil. sodium bicarbonate, water, brine and then dried over MgSO$_4$. The dried solution was filtered and concentrated to leave a clear dark brown oil. The product was purified by flash column chromatography with 2% MeOH/98% CH$_2$Cl$_2$ as eluent to leave a colorless oil (2.33 g; 66%). $^1$H NMR (360 MHz, CDCl$_3$) δ 7.81–7.43 (m, 5H), 5.78 (br s, 1H), 5.69 (q, 1H), 4.02–4.15 (m, 4H), 3.51–3.65 (m, 2H), 2.61–2.67 (m, 1H), 2.37 (d, 1H), 1.24–1.32 (m, 6H). $^{13}$C NMR (50 MHz, CDCl$_3$) δ 131.97, 129.64, 128.93, 127.16, 126.78, 87.39 (d, J=12 Hz), 62.97 (d, J=168 Hz), 62.44 (d, J=6.5 Hz), 58.07, 38.17, and 16.48 (d, J=6 Hz).

EXAMPLE P

Trans-1-diethylphosphonomethoxy-2-(phenylsulfinyl)-cyclopent-3-ene

The sulfide (2.1 g; 6.1 mmol), prepared as in Example O, was dissolved in CH$_2$Cl$_2$ (30 mL), under nitrogen, and cooled to 0° C. A solution of mCPBA (1.2 g; 7 mmol) in CH$_2$Cl$_2$ (10 mL) was then added dropwise. The reaction mixture was then stirred at 0° C. for 1.5 hrs. The reaction mixture was concentrated and flash chromatographed using 5% MeOH/95% CH$_2$Cl$_2$ as eluent. The product was a white solid (2.1 g; 95%). cl EXAMPLE Q

Trans-1-diethylphosphonomethoxycyclopent-2-en-4-ol

The sulphoxide (1 g, 2.7 mmol), prepared as in Example P, was dissolved in MeOH (3 mL) and trimethylphosphite (0.7 g, 5.6 mmol) added under a nitrogen atmosphere. The reaction mixture was heated to reflux for 4 hrs and then allowed to cool. A saturated solution of NaHCO$_3$ (3 mL) was added and the mixture stirred for ten minutes. The reaction mixture was then extracted with ethyl acetate (3×25 mL) and the organic washings dried (MgSO$_4$). The dried solution was filtered and concentrated to give a pale yellow oil. The desired product was obtained as a colorless oil (220 mg, 32%) after flash chromatography of the yellow oil with 5% MeOH/95% CH$_2$Cl$_2$ eluent mixture. $^1$H NMR (360 MHz, CDCl$_3$) δ 6.05–6.15 (m, 1H), 5.85–5.95 (m, 1H), 4.93–4.96 (m, 1H), 4.77–4.80 (m, 1H), 4.05–4.14 (septet, 4H), 3.66–3.69 (dd, 2H), 2.10–2.17 (m, 1H), 1.89–1.96 (m, 1H) and 1.25–1.29 (b, 6H). $^{13}$C NMR (50 MHz, CDCl$_3$) δ 139.37, 133.11, 85.81 (d, J=7 Hz), 75.71, 62.45, 62.35 (d, J=168 Hz), 40.29 and 16.41 (d, J=5 Hz).

EXAMPLE R cis-1-Diethylphosphonomethoxy-4-chlorocyclopent-2-ene

Trans-1-Diethylphosphonomethoxycyclopent-2-en-4-ol (380 mg, 1.52 mmol) was dissolved in CH$_2$Cl$_2$ (5 mL) and the solution was cooled in an ice bath under nitrogen. Triethylamine (168 mg, 1.68 mmol) was added by syringe followed by dropwise addition of a solution of toluenesulphonyl chloride (320 mg, 1.68 mmol) in CH$_2$Cl$_2$ (1 mL). A catalytic amount of DMAP was also added and then the reaction mixture left to stir overnight. The mixture was concentrated to leave a pale yellow oil which was purified by flash column chromatography. The chloride was isolated as a colorless oil (88 mg, 21%) along with a substantial amount of starting material (220 mg, 58%). $^1$H NMR (360 MHz, CDCl$_3$) δ 6.00–6.08 (m, 2H), 4.75–4.78 (m, 1H), 4.66–4.69 (m, 1H), 4.08–4.17 (m, 4H), 3.69–3.76 (m, 2H), 2.79–2.88 (quintet, 1H), 2.02–2.08 (d, 1H), 1.29–1.39 (d, 6H).

EXAMPLE S cis-1-Diethylphosphonomethoxy-4-chlorocyclopent-2-ene

Trans-1-diethylphosphonomethoxycyclopent-2-en-4-ol (220 mg, 0.88 mmol) was dissolved in CH$_2$Cl$_2$ (2 mL) and cooled to 0° C. under nitrogen. Triethylamine (192 mg, 1.92 mmol) was added followed by methanesulphonyl chloride (220 mg, 1.92 mmol) and the reaction mixture left to stir for 0.5 hrs at 0° C. The reaction mixture was allowed to warm to room temperature and MeOH was added. The aqueous solution was diluted with $CH_2Cl_2$ (10 mL) and washed with water, saturated $NaHCO_3$ and brine. The solution was dried ($MgSO_4$), filtered, concentrated and then purified by flash column chromatography with 5% MeOH/95% $CH_2Cl_2$ (144 mg, 62%).

EXAMPLE T (±)-9-(4-β-Diethylphosphonomethoxycyclopent-2-en-1-β-yl)adenine

Adenine (235 mg, 1.74 mmol) was added to a suspension of sodium hydride (0.045 g, 1.88 mmol) in DMF (15 mL) under a nitrogen atmosphere. The reaction mixture was warmed to 60° C. for 1 hr. to form a thick, viscous white suspension. The reaction was then allowed to cool to room temperature and a suspension of sodium bromide (0.18 g, 1.74 mmol) and cis-1-diethylphosphonomethoxy-4-chlorocyclopent-2-ene (0.45 g, 1.68 mmol) added. The reactants were warmed to 60° C. under a nitrogen atmosphere for 2 hours. The reaction mixture was allowed to cool and then concentrated in vacuo. The residue was dissolved in ethyl acetate (50 mL) and then washed with water and dilute hydrochloride acid (10%). The organic phase was then dried ($Na_2SO_4$). The solution was filtered and concentrated to leave a thick oil (300 mg). The product contained both the alpha and beta anomers from the condensation reaction in a 1:1 ratio determined by $^1H$ NMR. These two anomers were separated on an IBM instruments $C_{18}$ semi-preparative column using 35% methanol:65% ammonium acetate as eluent (adjusted to pH 7). The undesired product (±)-9-(4-β-diethylphosphonomethoxycyclopent-2-ene-1-β-yl) adenine elutes first as a white solid. Analysis: $C_{15}H_{22}N_5O_4P.0.5\ H_2O$ (calc'd): C: 47.86, H: 5.90, N: 18.64; (found): C: 48.23, H 5.99, N, 18.64. $^1H$ NMR (200 MHz, $CDCl_3$) δ 8.4 (s, 1H); 7.65 (s,1H); 7.25 (s, 1H), 6.4–6.5 (m, 1H), 6.2–6.25 (m, 1H), 5.8–5.9 (m, 1H), 5.0–5.1 (m, 1H), 4.15–4.25 (m, 4H), 3.75–3.85 (m, 2H), 2.55–2.7 (m, 1H), 2.25–2.4 (m, 1H) and 1.25–1.4 (t, 6H). $^{13}C$ NMR (90 MHz, $CDCl_3$) δ 155.49, 152.90, 149.75, 138.10, 136.54, 133.61, 119.88, 85.53 (d, J=12 Hz), 61.96 (d, J=170 Hz), 62.42 (d, J=7 Hz), 38.94, 36.41 and 16.33 (d, J=5 Hz).

(±) -9-(4-β-diethylphosphonomethoxycyclopent-2-ene-1-β-yl)adenine elutes off the column second m.p. 85°–87° C. $^1H$ NMR (200 MHz, $CDCl_3$) δ 8.37 (s, 1H), 6.39 (m, 1H), 6.15 (m, 1H), 5.65 (m, 1H), 4.2 (m, 4H), 3.85 (d, 2H), 2.95 (m, 1H), 2.00 (m, 1H) and 1.35 (m, 6H).

EXAMPLE U

Trans-1-Diethylphosphonomethoxy-4-phenylsulfinylcyclopent-2-ene

Trans-1-diethylphosphonomethoxycyclopent-2-en-4-ol (0.4 g; 1.6 mmol) was dissolved in $CH_2Cl_2$ (6 mL) and cooled to 0° C. in an ice bath under a nitrogen atmosphere. Triethylamine (0.3 g; 2.9 mmol) was then added followed by a solution of toluenesulfinyl chloride (0.4 g, 2.9 mmol) in $CH_2Cl_2$ (2 mL). The reaction mixture was stirred at 0° C. for 1 hr. The ice bath was removed and the reaction mixture concentrated in vacuo. The residual oil was purified by flash column chromotography with 2% methanol/98% dichloromethane as eluent. The product (0.54 g; 87%) was isolated as a colorless oil.

Analysis: $C_{17}H_{25}O_6PS.0.5H_2O$ (calc'd): C: 51.37, H: 6.35; (found): C: 51.66, H: 6.54.

Both the $^1H$ NMR and $^{13}C$ NMR show two diastereomers. $^1H$ NMR (360 MHz, $CDCl_3$) δ 7.55–7.59 (m, 2×2H); 7.30–7.34 (m, 2×2H), 6.09–6.15 (m, 1×2H and 1×1H), 5.70–5.73 (m, 1×1H), 5.39–5.43 (1m, 2×1H), 4.80–4.82 (m, 1×1H)), 4.75–4.77 (m, 1×1H)), 4.06–4.21 (m, 2×4H), 3.65–3.75 (m, 2×2H), 2.41 (s, 2×3H), 2.17–2.31 (m, 1×2H), 1.89–2.16 (m, 1×2H), 1.27–1.33 (m, 2×6H). $^{13}C$ NMR (50 MHz, $CDCl_3$) δ 136.5, 136.19, 135.77, 135.12, 129.67, 125.04, 85.32 (d, J=13 Hz) with 85.24 (d, J=13 Hz) (2×1C), 80.79 with 80.67 (2×1C), 62.81 (d, J=166 Hz) with 62.75 (d, J=167 Hz) (2×1C), 62.49 with 62.38 (2×1C), 38.68 with 38.12 (2×1C), 21.53, 16.50 with 16.39 (2×1C).

EXAMPLE V (±)-9-(4-Diethylphosphonomethoxycyclopent-2-en-1-β-yl)adenine

Adenine (0.22 g, 1.6 mmol) was added to a suspension of sodium hydride (0.045g; 1.8 mmol) in DMF (5 mL) under nitrogen and the reaction warmed to 60° C. for 1 hr. The reaction was allowed to cool to room temperature and a solution of trans-1-diethylphosphonomethoxy-4-phenylsulfinylcyclopent-1-ene (0.6 g; 1.55 mmol) in DMF (2 mL) was then added by syringe. The reaction mixture was warmed to 70° C. overnight. The reaction was allowed to cool, filtered to remove any solids; and then concentrated in vacuo. The residue was purified by flash column chromatography using 5% methanol:95% dichloromethane as eluent. The product was isolated as a white solid, m.p. 80°–91° C.

EXAMPLE W (±)-9-(4-β-Diethylphosphonomethoxycyclopent-2-en-1-β-yl)adenine

Trans-1-diethyl phosphonomethoxycyclopent-2-en-4-ol (0.02 g; 0.08 mmol) was dissolved in N-methylpyrrolidinone (1.5 mL) under a nitrogen atmosphere. To this triphenylphosphine (0.023 g, 0.09 mmol), diethyldiazodicarboxylate (0.016 g, 0.09 mmol) and adenine (0.011 g, 0.08 mmol) were added in order and the reaction mixture left overnight. HPLC analysis shows product to be present. The reaction mixture was concentrated and then purified by flash column chromotography to give the product. This was identical to the product prepared by the method of Example V.

EXAMPLE X (±)-9-(4-β-Hydroxycyclopent-2-en-1-β-yl)adenine

A solution of 3,4-epoxycyclopentene (1.325 g, 15.8 mmol) in DMF (5 mL) was added dropwise to a suspension of adenine (1.74 g; 12.88 mmol) and tetrakis (triphenylphosphine)palladium (0) (0.74 g, 0.6 mmol) in DMF (25 mL) and THF (5 mL) mixture under a nitrogen atmosphere. The reaction mixture was stirred at ambient temperature for 1 hr. and then warmed to 80°–90° C. for a further 1 hr. The reaction mixture was poured into water and then filtered. The filtrate was concentrated to leave a dark oil. The oil was purified by flash column chromatography using a methanol/dichloromethane mixture as eluent (3% MeOH/$CH_2Cl_2$ increasing to 5% MeOH/$CH_2Cl_2$). The product was isolated as a white solid, m.p. 164°–167° C. $^1$H NMR (360 MHz, CDCl$_3$) δ 8.26 (s, 1H), 7.83 (s, 1H), 6.33 (q, 1H), 5.80 (m, 1H), 5.26 (m, 1H), 4.84 (d, 1H), 2.97 (m, 1H), 2.23 (d, 1H).

$^{13}$C NMR (50 MHz, DMSO-d$_6$) 156.02, 152.13, 143.62, 139.27, 139.24, 130.64, 119.03, 73.75, 57.12 and 41.08. MS [M+H]=218.

EXAMPLE Y (±)-9-(4-β-Diethylphosphonomethoxycyclopent-2-en-1-β-yl)adenine (±)-9-(4-β-Hydroxycyclopent-2-en-1-β-yl)adenine (3.1 g, 14 mmol) in dry THF (30 mL) was added dropwise over 0.5 hrs to a stirred suspension of sodium hydride (97%, 0.376 g, 15.7 mmol) in THF (10 mL) under nitrogen. Once the addition had been completed the reaction mixture was heated to reflux for 1 hr. The solution was allowed to cool to ambient temperature and then cooled to −70° C. with a dry ice/acetone bath. A solution of trifluoromethanesulfonyloxymethyldiethyl phosphonate (4.8 g, 16.0 mmol) in THF (30 mL) was then added dropwise over 0.25 hrs. The reaction mixture was stirred at −78° C. for 2 hrs and then allowed to warm to room temperature overnight. The solution was concentrated in vacuo to leave a thick oil. This oil was purified by flash column chromatography with methanol/dichloromethane as eluent (5% MeOH/CH$_2$Cl$_2$ increasing to a 10% MeOH/CH$_2$Cl$_2$ mixture) to give the desired product as a beige colored solid (2.0 g, 40%). m.p. 88°–90° C. Analysis: C$_{15}$H$_{22}$N$_5$O$_4$P (calc'd): C: 49.05, H: 6.04, N: 19.07; (found): C: 49.19, H: 5.96, N: 19.35. $^1$H NMR (360 MHz, CDCl$_3$) δ 8.35 (s, 1H), 7.94 (s, 1H), 6.37 (m, 1H), 6.10 (m, 1H), 5.63 (m, 1H), 4.69 (m, 1H), 4.16 (quintet, 4H), 3.85 (m, 2H), 2.9 (m, 1H), 1.97 (dt, 1H), 1.33 (m, 4H).

$^{13}$C NMR (50 MHz, CDCl$_3$) δ 155.73, 152.89, 149.83, 139.58, 136.11, 134.02, 119.80, 84.82 (d, J=12Hz), 64.58 (d, J=167 Hz), 62.90 (d, J=2.5 Hz), 62.77 (d, J=2.5 Hz), 36.84, 33.76 and 16.76 (d, J=5 Hz).

EXAMPLE Z (±)-9-(4-β-Monoethylphosphonomethoxycyclopent-2-en-1-β-yl)adenine (±)-9-(4-β-Diethylphosphonomethoxycyclopent-2-en-1-β-yl)adenine (0.5g; 1.35 mmol) was dissolved in a solution of 1N sodium hydroxide (13 mL) and the reaction mixture stirred at room temperature for 2 hrs. The solution was acidified with 10% aqueous hydrochloric acid and then concentrated. Residual salts were removed by reverse phase column chromatography (C$_{18}$ adsorbent, elution with water) to give the product as a white solid (180 mg). m.p. 192°–205° C. Analysis: C$_{13}$H$_{18}$N$_5$O$_4$P.0.5H$_2$O (calc'd): C: 44.83, H: 5.50, N: 20.11; (found): C: 45.31, H:5.37, N: 20.17.

$^1$H NMR (300 MHz, DMSO-d$_6$) δ 8.19 (s, 1H), 8.04 (s, 1H), 7.57 (br s, 1H), 6.30 (d, 1H), 6.18 (d, 1H), 5.50 (br s, 1H), 4.67 (br s, 1H), 3.95 (m, 2H), 3.74(m,2H), 2.87 (m, 1H), 1.90 (m, 1H), 1.22 (s, 3H). $^{13}$C NMR (75 MHz, DMSO-d$_6$) δ 155.65, 151.92, 149.02, 138.78, 135.45, 133.33, 116.79, 83.73 (d, J=13 Hz), 63.29 (d, J=161 Hz), 60.68, 56.52, 37.76 and 16.35 (d, J=5 Hz).

EXAMPLE AA

: (±)-9-(4-β-Phosphonomethoxycyclopent-2-en-1-β-yl)adenine

Bromotrimethylsilane (2.1 g, 13.5 mmol) was added to a solution of (±)-9-(4-β-diethylphosphonomethoxycyclopent-2-en-1-β-yl)adenine (0.5 g, 1.35 mmol) in dry DMF (5 mL) at room temperature under a nitrogen atmosphere. The reaction vessel was covered with foil. The reaction mixture was left to stir at room temperature for 4 hrs. The volatiles were then removed in vacuo to leave a thick oil. The residue was treated with water (2–3 mL) followed by acetone (2–3 mL). After standing for a few minutes a brown precipitate falls out. The precipitate was collected and crystallized from water/acetone (80 mg). m.p. 218°–220° C. (dec).

Analysis: C$_{11}$H$_{14}$N$_5$O$_4$P.0.5H$_2$O (calc'd): C: 41.26, H: 4.42, N: 21.87; (found): C: 41.53, H: 4.49, N: 21.57.

$^1$H NMR (360 MHz, DMSO-d$_6$) δ 8.16 (s, 1H), 8.03 (s, 1H), 7.38 (s, 1H), 6.36 (d, 1H), 6.16 (d, 1H), 5.49 (br s, 1H), 4.66 (br s, 1H), 3.64 (d, 2H), 2.87 (m, 1H), 1.90 (d, 1H).

$^{13}$C NMR (75 MHz, DMSO-d$_6$) δ 155.62, 151.93, 149.05, 138.80, 135.54, 133.13, 118.85, 83.62 (d, J=5 Hz), 64.87 (d, J=169 Hz), 56.46 and 37.61.

EXAMPLE BB (±)-9-(4-β-Diethylphosphonomethoxycyclopentan-1-β-yl)adenine (±)-9-(4-β-Diethylphosphonomethoxy-2-cyclopentane-1-β-yl)adenine (0.4 g, 1.1 mmol) was dissolved in ethanol (10 mL) and PtO$_2$ catalyst (20 mg) added. The reaction was stirred under a hydrogen atmosphere for 18 hrs. The reaction mixture was filtered and purified by flash column chromatography to give the product as a colorless oil (378 mg).

Analysis: C$_{15}$H$_{24}$N$_5$O$_4$P.0.5 EtOH (calc'd): C: 48.96, H: 6.95, N: 17.84; (found): C: 48.93, H: 6.83, N: 17.48. $^1$H NMR (200 MHz, CDCl$_3$) δ 8.39 (s, 1H), 8.12 (d, 1H), 6.13 (br s, 1H), 5.18 (br s, 1H), 4.20–4.35 (m, 4H), 3.90 (m, 2H), 1.8–2.62 (set of m, 6H) and 1.37 (m, 6H). $^{13}$C NMR (50 MHz, CDCl$_3$) δ 155.80, 152.38, 149.48, 138.99, 110.95, 82.88 (d, J=13 Hz), 62.44 (d, J=168 Hz), 62.35 (d, J=27 Hz), 61.96, 52.21, 39.18, 31.63, 30.68 and 16.45 (d, J=5 Hz).

EXAMPLE CC (±)-9-4-β-Phosphonomethoxycyclopentan-1-β-yl)adenine

Bromotrimethylsilane (0.84 g, 5.5mmol) was added to a solution of (±)-9-4-β-diethylphosphonomethoxycyclopentan-1-β-yl)adenine (0.2 g; 0.55 mmol) in dry DMF (2 mL) at room temperature under a nitrogen atmosphere and the reaction mixture stirred for 12 hrs. The volatiles were removed in vacuo to leave a thick oil. Water was added and the oil went into solution. Acetone was then added and a precipitate fell out of solution. The precipitate was recrystallized from water/acetone. The product was a white solid, m.p. 255° C. (dec). Analysis: C$_{11}$H$_{16}$N$_5$O$_4$P.0.5H$_2$O (calc'd): C: 42.08, H: 5.15, N: 22.36; (found): C: 42.36, H: 5.15, N: 22.20. $^1$H NMR (200 MHz, DMSO-d$_6$) δ 8.25 (s, 1H), 8.19 (s,1H), 7.2 (br s, 2H), 5.0 (m, 1H), 4.18 (m, 1H), 3.33 (d, 2H), 1.6–2.4 (m, 6H).

EXAMPLE DD (±)-6-Q-Benzyl-9-(4-β-hydroxycyclopent-2-en-1-β-yl)guanine

A solution of 3,4-epoxycyclopentene (6.38 g, 77.7 mmol) in DMF (10 mL) was added dropwise over 0.66 hr. to a prewarmed (67° C.) solution of 6-O-benzylguanine (12.5 g, 52.6 mmol), tetrakis(triphenylphosphine)palladium (0) (3.0 g, 2.6 mmol) and triphenylphosphine (1.35 g, 5.51 mmol) in DMF (150 mL). Once all the epoxide had been added the reaction was left at 75° C. overnight. The reaction mixture was then allowed to cool to room temperature. The reaction was filtered and then concentrated to a yellowish oil. This oil was purified by flash column chromatography using a methanol/dichloromethane mixture as eluent (1% MeOH/ $CH_2Cl_2$ increasing to 10% MeOH/$CH_2Cl_2$) to give the product as a white solid (13.0 g, 77%). m.p.: 110°–115° C.

Analysis: $C_{17}H_{17}N_5O_2 \cdot 0.5H_2O$ (calc'd): C: 61.44 H: 5.46, N: 21.08, (found): 61.32, H: 5.43, N: 19.78. $^1$H NMR (360 MHz, DMSO-$d_6$+$D_2O$) δ 7.76 (s, 1H), 7.29–7.46 (m, 5H), 6.13 (m, 1H), 5.89 (m, 1H), 5.47 (s, 1H), 5.25 (br s, 1H), 4.66 (br s, 1H), 2.69–2.85 (m, 1H) and 1.55–1.61(m, 1H). $^{13}$C NMR (50 MHz, $CDCl_3$) δ 161.15, 158.29, 152.50, 139.49, 139.38, 136.18, 129.89, 128.30, 128.16, 127.95, 116.77, 75.04, 68.01, 9.53 and 39.37.

EXAMPLE EE (±)-$N^2$-monomethoxytrityl-6-O-Benzyl- 9-(4-β-hydroxycyclopent-2-en-1-β-yl)guanine (±)-6-O-Benzyl-9-(4-β-hydroxycyclopent- 2-en-1-β-yl) guanine (12.65 g, 39.12 mmol) was dissolved in DMF (200 mL) and anisylchlorodiphenylmethane (14.53 g, 46.94 mmol), triethylamine (9.8 g, 13.5 mL, 97.03 mmol) and dimethylaminopyridine (DMAP) (100 mg) were then added in turn. Once all the reactants had been added the reaction was stirred at room temperature overnight. The DMF was then removed in vacuo to leave a pale yellow oil which was purified by flash column chromatography with ethyl acetate/ hexane as eluent (10:1 EtOAc/Hexane). The desired product was isolated as a colorless oil which became a foam on drying (21.5 g, 92%). Analysis $C_{17}H_{33}N_5O_3 \cdot 1.0H_2O$: (calc'd): C: 72.43, H: 5.38, N: 11.41, (found): C: 72.43, H: 5.73, N: 12.06.

$^1$H NMR (360 MHz, $CDCl_3$) δ 7.99 (s, 1H), 7.36 (s, 1H), 7.14–7.29 (m, 17H), 6.73 (d, 2H), 6.23 (d, 1H), 5.77 (m, 1H), 5.10 (d, 1H), 4.76 (d, 1H), 4.70 (s, 2H), 3.79 (s, 3H), 2.79–2.80 (m, 1H), 2.06 (d, 1H).

EXAMPLE FF (±)-$N^2$-monomethoxytrityl-6-O-benzyl-9-(4-β-diethylphosphonylmethoxycyclopent-2-en-1-β-yl)guanine (±)-N2-monomethoxytrityl-6-O-benzyl-9-(4-β-hydroxy-cyclopent-2-en-1-β-yl)guanine (8.3 g, 13.93 mmol) was dissolved in DMF (90 mL) and stirred under argon. Sodium hydride (80%, 0.835 g, 27.9 mmol) was then added and the resulting slurry stirred at room temperature for 2.5 hr. during which time the reaction mixture became dark brown. Diethyl tosyloxymethylphosphonate (6.7 g, 20.90 mmol) was introduced into the suspension via a syringe. The reaction mixture was stirred at room temperature for 20 hr. during which time it became homogeneous. Ethanol (10 mL) was added and the reaction stirred for a further 0.3 hr. The solution was concentrated in vacuo and the residue flash chromatographed on silica with ethanol/ethyl acetate (2–10%) as eluent. The desired fractions were collected to afford the product (5.7 g, 57%) as an off-white foam after drying in vacuo. Analysis $C_{42}H_{44}N_5O_6P \cdot 0.5H_2O$: (calc'd): C: 66.84, H: 6.01, N: 9.28, (found): C: 67.09, H: 6.10, N: 9.01.

$^1$H NMR (300 MHz, DMSO-$d_6$) δ 7.56 (s, 1H), 7.45–7.13 (m, 17H), 6.81 (d, 2H), 6.26 (br s, 1H), 6.01 (br s, 1H), 5.03 (br m, 3H, H4' plus $CH_2$), 4.56 (br s, 1H), 4.05–3.95 (m, 4H), 3.85 (d, J=8 Hz, 2H), 3.68 (s, 3H), 2.60 (m, 1H), 1.70 (m, 1H), 1.18 (m, 6H).

EXAMPLE GG (±)-9-(4-β-Diethylphosphonylmethoxycyclopent-2-en-1-β-yl)guanine

The product from example FF (3.65 g, 2.68 mmol) was dissolved in glacial acetic acid (90 mL), and the resulting yellow solution was heated on a steam bath with occasional swirling for 3 hr. The acetic acid was removed in vacuo and residue flash chromatographed on silica using methanol/ dichloromethane (5–10%) as eluent. The desired product was obtained as a white solid (3.65 g, 68%).

Analysis $C_{15}H_{22}N_5O_5P$: (calc'd): C: 47.00, H: 5.79, N: 18.27, (found): C: 46.82, H: 6.00, N: 17.92. $^1$H NMR (360 MHz, DMSO-$d_6$) δ 7.31 (s, 1H), 6.27 (s, 2H), 6.16 (m, 1H), 5.96 (m, 1H), 5.05 (m, 1H), 4.43 (m, 1H), 3.85 (m, 4H), 3.72 (d, 2H), 2.59 (m, 1H), 1.64 (m, 1H), 1.05 (m, 6H). $^{13}$C NMR (50 MHz, DMSO-$d_6$) δ 156.73, 153.46, 150.53, 135.16, 134.93, 133.86, 116.54, 83.83 (d, J=13 Hz), 61.89 (d, J=163 Hz), 61.73, 61.61, 56.00, 37.60, 16.20 (d, J=6 Hz).

EXAMPLE HH (±)-9-(4-β-Dihydroxyphosphonomethoxycyclopent-2-en-1-β-yl)guanine (±)-9-(4-β-Diethylphosphonomethoxycyclopent-2-en-1-β-yl)guanine (1.15 g; 3.0 mmol) was placed in dry DMF (20 mL) to give a white slurry. Bromotrimethylsilane (3.9 mL) was added by syringe and the reaction mixture which immediately became homogeneous was stirred at ambient temperature for 20 hr. under argon. The yellow solution was concentrated in vacuo to remove the solvent residue (1 g) and was dried under vacuum for 3 hr. The resultant foam was dissolved in $H_2O$ (5 mL) and stirred for 0.5 hr. Acetone was then added to the reaction mixture and a white precipitate came out of solution. The reaction was left stirring for 18 hr. The solution was filtered and the white precipitate collected. The solid was then recrystallized from water to afford the product as a white crystalline solid (860 mg, 88%)

Analysis $C_{11}H_{14}N_5O_5P \cdot 1.0H_2O$: (calc'd): C: 38.27, H: 4.68, N: 20.29, (found): C: 38.10, H: 4.76, N: 20.24.

$^1$H NMR (360 MHz, DMSO-$d_6$) δ 7.58 (s, 1H), 6.45 (s, 2H), 6.29 (m, 1H), 6.06 (m, 1H), 5.21 (br s, 1H), 4.60 (m, 1H), 3.62 (m, 2H), 2.77 (m, 1H), 1.78 (m, 1H). $^{13}$C NMR (75 MHz, DMSO-$d_6$) δ 156.57, 153.36, 150.45, 135.41, 133.26, 116.23, 83.57, 6418 (d, J=161 Hz), 56.07, 37.64.

EXAMPLE II (±)-$N^2$-Monomethoxytrityl-6-O-benzyl-9-[4-β-(diethylphosphonomethoxy)- 2,3-α,α-(dihydroxy)cyclopentan-1-β-yl]guanine A solution of (±)-$N^2$-monomethoxytrityl-6-O-benzyl-9-[4-β-(diethylphosphonomethoxy)cyclopent-2-en-1-β-yl]guanine (11.7 g, 15.7 mmol), Example FF, in anhydrous pyridine (50 mL) was treated with a solution of osmium tetroxide (4.0 g, 15.7 mmol) in pyridine (20 mL) at room temperature under argon. After 2.5 hr., additional osmium tetroxide (0.25 g, 0.99 mmol) in pyridine (2 mL) was added and the reaction mixture was stirred further for 4 hr. The black solution was then treated with pyridine (50 mL) and a solution of sodium bisulfite (8.0 g) in water (60 mL). The resulting mixture was; stirred at room temperature for 0.5 hr. and poured into a separatory funnel containing $CH_2Cl_2$ (1 L) and $H_2O$ (300 mL). The mixture was vigorously shaken, the layers were separated, and the aqueous phase was extracted with $CH_2Cl_2$ (300 mL). The combined organic layers were washed with $H_2O$ (150 mL), dried over anhydrous $Na_2SO_4$, filtered, and concentrated. The residue was concentrated from toluene (3×150 mL) to give 12.8 g (105% crude yield) of the product as a crisp, pale-yellow foam which could be used in subsequent reactions without purification. On a separate run (0.73 g of starting olefin, 0.98 mmol), the reaction mixture was purified by column chromatography on silica gel (20:1, elution with 5% MeOH/$CH_2Cl_2$) to provide 0.71 g (93%) of the desired product as a clear, colorless glass.

Analysis: $C_{42}H_{46}N_5O_8P\cdot0.25\ H_2O$: (calc'd): C: 64.32, H: 5.98, N: 8.93. (found): C: 64.26, H: 5.94, N: 8.93. $^1$H NMR (300 MHz, DMSO-$d_6$): 7.84 (br s, 1H, H-8), 7.12–7.40 (m, 18H, NH and ArH), 6.80 (d, 2H, ArH, J=9 Hz), 4.90–5.10 (m, 4H, 2×-OH and O$\underline{CH_2}$Ph), 4.23–4.38 (m, 1H, H-1'), 3.97–4.18 (m, 5H, H-2' and PO$\underline{CH_2}$×2), 3.70–3.85 (m, 3H, H-4' and O$\underline{CH_2}$P), 3.66–3.70 (m, 1H, H-3'), 3.68 (s, 3H, O$\underline{CH_3}$), 2.15–2.30 (m, 1H, H-5'a), 1.65–1.78 (m, 1H, H-5'b), and 1.22 (t, 6H, POCH$_2\underline{CH_3}$×2, J=7 Hz). $^{13}$C NMR (75 MHz, DMSO-$d_6$): 158.98 (C-6), 157.56 (C-2), 157.02 (C-4), 145.99, 145.84, 139.72 (ArC), 137.83 (C-8), 136.58, 130.04, 128.64, 128.47, 128.29, 128.08, 127.50, 126.16 (ArC), 114.81 (C-5), 112.83 (ArC), 84.58 (d, C-4', J=13 Hz), 73.23 (C-2' and C-3'), 69.70 (C$\underline{Ar_3}$), 66.86 (O$\underline{CH_2}$Ph), 62.63 (d, O$\underline{CH_2}$P, J=165 Hz), 61.85 (d, PO$\underline{CH_2}$, J=7 Hz), 58.04 (C-1'), 55.03 (O$\underline{CH_3}$), and 16.41 (d, POCH$_2\underline{CH_3}$, J=5 Hz).

EXAMPLE JJ (±)-9-[4-β-(Diethylphosphonomethoxy)-2,3-α,α-(dihydroxy)cyclopentan-1-β-yl]guanine (±)-N$^2$-Monomethoxytrityl-6-β-benzyl-9-[4-β-(diethylphosphonomethoxy)-2,3-α,α-(dihydroxy)cyclopentan-1-β-yl]guanine (3.0 g, 3.85 mmol), Example II, was treated with 75% aqueous acetic acid (75 mL) and the mixture was heated on a steam bath for 3 hr. with occasional swirling. The clear, yellow solution was concentrated in vacuo and the resulting viscous residue was concentrated from absolute ethanol (2×75 mL) to give 3 g of a yellow oil. Purification by column chromatography on silica gel (10:1, elution with 10% to 15% to 20% MeOH/$CH_2Cl_2$) provided 1.32 g (82%) of the product as a white gum. m.p. 163°–166° C.

Analysis: $C_{15}H_{24}N_5O_7P\cdot0.25\ H_2O$: (calc'd): C: 42.71, H: 5.86, N: 16.61. (found): C: 42.79, H: 5.68, N: 16.44.

$^1$H NMR (300 MHz, DMSO-$d_6$): 10.52 (s, 1H, NH), 7.70 (s, 1H, H-8), 6.39 (br s, 2H, —NH$_2$), 5.08 (d, 1H, —OH, J=6 Hz), 5.00 (d, 1H, —OH, J=4 Hz), 4.48 (dd, 1H, H-1', J=9,17 Hz), 4.22–4.32 (m, 1H, H-2'), 3.98–4.10 (m, 4H, POC$\underline{H}_{2×2}$), 3.80–3.90 (m, 3H, H-3' and O$\underline{CH_2}$P), 3.74–3.79 (m, 1H, H-4'), 2.43–2.55 (m, 1H, H-5'a), 1.75–1.85 (m, 1H, H-5'b), and 1.23 (t, 6H, POCH$_2\underline{CH}_{3×2}$, J=7 Hz). $^{13}$C NMR (75 MHz, DMSO-$d_6$): 156.92 (C-6), 153.35 (C-2), 151.55 (C-4), 136.01 (C-8), 116.89 (C-5), 84.21 (d, C-4', J=12 Hz), 74.91 (C-2'), 73.65 (C-3'), 62.50 (d, O$\underline{CH_2}$P, J=165 Hz), 61.91 (d, PO$\underline{CH_2}$, J=8 Hz), 57.11 (C-1'), 33.45 (C-5'), and 16.40 (d, POCH$_2\underline{CH_3}$, J=5 Hz).

EXAMPLE KK (±)-9-[4-β-(Dihydroxyphosphonomethoxy)-2,3-α,α-(dihydroxy)cyclopentan-1-β-yl]guanine Bromotrimethylsilane (1.84 g, 12.0 mmol) was added dropwise to a slurry of (±)-9-[4-β-diethylphosphonomethoxy)-2,3-α,α-(dihydroxy)cyclopentan-1-β-yl]guanine (0.50 g, 1.2 mmol), Example JJ, in anhydrous DMF (10 mL) at room temperature under argon. The resulting clear, yellow solution was stirred for 18 hr. and then concentrated in vacuo. The residue was coevaporated with DMF (2×30 mL), placed under high vacuum for 3 hr., and treated with water (5 mL). After stirring at room temperature for 0.5 hr., the aqueous solution was treated with ethanol (40 mL). The resulting precipitate was collected by filtration, washed with absolute ethanol, dissolved in water, and then lyophilized to give 0.14 g (32%) of the product as a fluffy white solid. Concentration of the filtrate gave a residue which was dissolved in ethanol (10 mL) and treated with ethyl acetate (75 mL). The solid that formed was collected by filtration, dissolved in water, and lyophilized to provide an additional 0.27 g (62%) of the product. The total yield of the reaction was 94%. m.p.: softens ~185° C., decomp. >250° C. Analysis: $C_{11}H_{16}N_5O_7P\cdot0.5\ H_2O$. (calc'd): C: 35.69, H: 4.63, N: 18.92. (found): C: 35.81, H: 4.84, N: 19.10. $^1$H NMR (300 MHz, DMSO-$d_6$): 10.66 (br s, 1H, NH), 7.95 (s, 1H, H-8), 6.53 (br s, 2H, NH$_2$), 4.46–4.57 (m, 1H, H-1'), 4.32–4.37 (m, 1H, H-2'), 3.85–3.91 (m, 1H, H-4'), 3.70–3.76 (m, 1H, H-3'), 3.58 (d, 2H, O$\underline{CH_2}$P, J=10 Hz), 2.43–2.54 (m, 1H, H-5'a), and 1.79–1.90 (m, 1H, H-5'b). $^{13}$C NMR (75 MHz, DMSO-$d_6$): 156.36 (C-6), 153.62 (C-2), 151.33 (C-4), 136.27 (C-8), 115.45 (C-5), 83.90 (d, C-4', J=13 Hz), 74.89 (C-2'), 73.59 (C-3'), 64.72 (d, O$\underline{CH_2}$P, J=162 Hz), 57.54 (C-1'), and 33.30 (C-5').

EXAMPLE LL 2,3-Cyclic sulfate ester of (±)-N$^2$-Monomethoxytrityl-6-O-benzyl-9-[4-β-(diethylphosphonomethoxy)- 2,3-α,α-(dihydroxy)cyclopentan-1-β-yl]guanine A solution of (±)-N$^2$-monomethoxytrityl-6-O-benzyl-9-[4-β-(diethylphosphonomethoxy)-2,3-α,α-(dihydroxy)cyclopentan-1-β-yl]guanine (9.50 g, 12.2 mmol), Example II, in anhydrous $CH_2Cl_2$ (60 mL) was treated with triethylamine (6.16 g, 60.9 mmol) at room temperature under argon. The mixture was cooled to 0° C. and sulfuryl chloride (18.3 mL, 1M in $CH_2Cl_2$, 18.3 mmol) was added dropwise via addition funnel over 40 min. After 2 hr. at 0° C., the reaction mixture was allowed to warm to room temperature, stirred further for 4 hr., and then quenched by addition of $CH_2Cl_2$ (200 mL) and water (80 mL). The biphasic mixture was stirred for 15 min and then poured into a separatory funnel containing $CH_2Cl_2$ (200 mL) and water (40 mL). The layers were agitated and separated, and the organic phase was washed with water (80 mL) and saturated NaCl solution (100 mL), dried over anhydrous $Na_2SO_4$, filtered, and concentrated to give 11 g of a white foam. Purification by column chromatography on silica gel (30:1, gradient elution with 1% to 10% EtOH/EtOAc) gave 9.45 g (92%) of the product as a white foam.

Analysis: $C_{42}H_{44}N_5O_{10}PS$: (calc'd): C: 59.93, H: 5.27, N: 8.32. (found): C: 59.85, H: 5.42, N: 8.31. $^1$H NMR (300 MHz, DMSO-$d_6$): 7.90 (s, 1H, H-8), 7.81 (s, 1H, NH), 7.13–7.37 (m, 17H, ArH), 6.82 (d, 2H, ArH, J=9 Hz), 5.35–5.54 (br m, 4H, OCH$_2$Ph, H-2' and H-3'), 4.90–5.01 (m, 1H, H-1'), 4.22–4.33 (m, 1H, H-4'), 4.02–4.14 (m, 4H, POCH$_2$×2), 3.95 (d, 2H, OCH$_2$P, J=9 Hz), 3.68 (s, 3H, OCH$_3$), 2.37–2.50 (m, 1H, H-5'a), 1.93–2.13 (m, 1H, H-5'b), and 1.25 (t, 6H, POCH$_2$CH$_3$×2, J=7 Hz). $^{13}$C NMR (75 MHz, DMSO-d$_6$): 161.12 (C-6), 159.29 (C-2), 158.87 (C-4), 147.41, 147.02, 141.32 (ArC), 139.10 (C-8), 138.14, 131.72, 130.41, 130.28, 130.15, 129.88, 129.30, 129.23,127.95 (ArC), 116.61 (C-5), 114.53 (ArC), 87.43 (C-2' and C-3'), 83.24 (d, C-4', J=12 Hz), 71.44 (CAr$_3$), 68.79 (OCH$_2$Ph), 65.05 (d, OCH$_2$P, J=164 Hz), 63.70 (d, POCH$_2$, J=6 Hz), 57.55 (C-1'), 56.62 (OCH$_3$), 33.18 (C-5'), and 18.04 (d, POCH$_2$CH$_3$, J=6 Hz).

EXAMPLE MM (±)-9-[4-β-(Diethylphosphonomethoxy)-2-β-fluoro-3-α-hydroxycyclopentan-1-β-yl]guanine The 2,3-cyclic sulfate ester of (±)-N$^2$-monomethoxytrityl-6-O-benzyl-9-[4- β-(diethylphosphonomethoxy)-2,3-α,α-(dihydroxy)cyclopentan-1-β-yl]guanine (6.00 g, 7.13 mmol), Example LL, was dissolved inn acetone (50 mL) under argon and the solution was cooled to 0° C. Anhydrous tetrabutylammonium fluoride (2.80 g, 10.7 mmol) was added in one portion and the resulting brown solution was stirred at 0° C. for 3 hr., allowed to warm to room temperature, and stirred for 18 hr. The mixture was treated with additional Bu$_4$NF (0.57 g, 2.2 mmol), stirred further for 18 hr., and then concentrated in vacuo. The residue was partitioned between CH$_2$Cl$_2$ (500 mL) and water (150 mL), and the organic layer was washed with saturated NaHCO$_3$ solution (125 mL) and saturated NaCl solution (125 mL). The organic phase was then dried over anhydrous Na$_2$SO$_4$, filtered, and concentrated to give 8.0 g of a yellow foam. Purification by column chromatography on silica gel (50:1, gradient elution with 4% to 20% MeOH/EtOAc) afforded 3.41 g of a product with R$_f$=0.32 and 1.66 g of a product with R$_f$=0.19 (TLC solvent system: 20% EtOH/EtOAc).

The higher R$_f$ product (3.35 g) was treated with 1N HCl solution (40 mL) and heated at 80° C. for 18 hr. The mixture was allowed to cool to room temperature and poured into a separatory funnel containing CH$_2$Cl$_2$ (200 mL) and water (200 mL). The layers were agitated and separated, and the aqueous phase was washed with CH$_2$Cl$_2$ (50 mL) and concentrated in vacuo. The residue was concentrated from water (2×75 mL), placed under high vacuum for 18 hr., and purified by reversed-phase column chromatography on C18 adsorbent (2.2 g crude, 30:1, gradient elution with 0% to 40% MeOH/H$_2$O) to give 1.16 g of the product as a white glass (39% overall yield from the cyclic sulfate ester). Analysis: C$_{15}$H$_{23}$N$_5$O$_6$PF.0.75 H$_2$O: (calc'd): C: 41.63, H: 5.71, N: 16.18. (found): C: 41.43, H: 5.67, N: 16.16. $^1$H NMR (300 MHz, DMSO-d$_6$): 10.62 (br s, 1H, NH), 7.76 (d, 1H, H-8, J=2 Hz), 6.49 (br s, 2H, NH$_2$), 5.81 (d, 1H, —OH, J=4 Hz), 4.67–4.84 (m, 2H, H-1' and H-2'), 4.00–4.11 (m, 5H, H-3' and POCH$_2$×2), 3.83–3.93 (m, 3H, H-4' and OCH$_2$P), 2.57–2.68 (m, 1H, H-5'a), 2.24– 2.36 (m, 1H, H-5'b), and 1.24 (t, 6H, POCH$_2$CH$_3$×2, J=7 Hz). $^{13}$C NMR (75 MHz, DMSO-d$_6$): 156.75 (C-6), 153.53 (C-2), 151.25 (C-4), 136.54 (C-8), 116.02 (C-5), 95.93 (d, C-2', J=185 Hz), 85.13 (d, C-4', J=13 Hz), 78.11 (d, C-3', J=25 Hz), 62.80 (d, OCH$_2$P, J=165 Hz), 62.06 (d, POCH$_2$, J=6 Hz), 52.18 (d, C-1', J=18 Hz), 32.22 (C-5'), and 16.34 (d, POCH$_2$CH$_3$, J=5 Hz).

EXAMPLE NN (±)-9-[4-β-(Dihydroxyphosphonomethoxy)-2-β-fluoro-3-α-hydroxycyclopentan-1-β-yl]guanine A solution of (±)-9-[4-diethylphosphonomethoxy-2-β-fluoro-3-α-hydroxycyclo-pentan-1-β-yl]guanine (0.21 g, 0.50 mmol), Example MM, in anhydrous DMF (5 mL) was treated dropwise via syringe with bromotrimethylsilane (0.62 g, 4.0 mmol) at room temperature under argon. The resulting clear, yellow solution was stirred for 20 hr. and then concentrated in vacuo. The residue was concentrated from DMF (2×15 mL), placed under high vacuum at 40° C. for 72 hr., and then dissolved in water (2 mL). Purification by reversed-phase column chromatography on C$_{18}$ adsorbent (0.50 g crude, 50:1, elution with H$_2$O) afforded 0.09 g (50%) of the product as a white solid.

m.p.: darkened ~230° C., red 230°–250° C. Analysis: C$_{11}$H$_{15}$N$_5$O$_6$PF.1.75 H$_2$O: (calc'd): C: 33.47, H: 4.73, N: 17.75. (found): C: 33.52, H: 4.77, N: 17.55. $^1$H NMR (300 MHz, D$_2$O): 7.86 (d, 1H, H-8, J=2 Hz), 4.73–4.95 (m, 2H, H-1' and H-2'), 4.24 (d, 1H, H-3', J=23 Hz), 3.80–3.88 (m, 1H, H-4'), 3.45–3.59 (m, 2H, OCH$_2$P), 2.68–2.80 (m, 1H, H-5'a), and 2.17–2.30 (m, 1H, H-5'b). $^{13}$C NMR (75 MHz, DMSO-d$_6$): 156.77 (C-6), 153.67 (C-2), 151.20 (C-4), 136.36 (C-8), 116.17 (C-5), 96.14 (d, C-2', J=185 Hz), 85.19 (d, C-4', J=12 Hz), 78.39 (d, C-3', J=25 Hz), 65.39 (d, OCH$_2$P, J=162 Hz), 52.05 (d, C-1', J=19 Hz), and 32.34 (C-5').

EXAMPLE OO (±)-N$^2$-Acetyl-9-[4-β-(diethylphosphonomethoxy)-2-β-fluorocyclopentan-1-β-yl]guanine 1,1'-Thiocarbonyldiimidazole (0.31 g, 1.7 mmol) was added in one portion to a solution of (±)-9-[4-β-(diethylphosphonomethoxy)-2-β-fluoro-3-α-hydroxycyclopentan-1-β-yl]guanine (0.60 g, 1.43 mmol), Example MM, in anhydrous DMF (7 mL). The resulting orange slurry was heated at 80° C. for 2 hr. and then additional imidazole reagent (0.076 g, 0.43 mmol) was added. The mixture was stirred at 80° C. for 2.5 hr. and at room temperature for 15 hr., and then concentrated in vacuo.

The residue was dissolved in anhydrous 1,4-dioxane (30 mL) and treated with AIBN (3 mg), bis(tri-n-butyltin)oxide (3.4 g, 2.9 mL, 5.7 mmol), and polymethylhydrosiloxane (2.9 mL). The mixture was heated at reflux for 12 hr. and then concentrated in vacuo. A solution of the viscous residue in MeOH (100 mL) was washed with hexane (3×40 mL) and concentrated in vacuo to give 1.2 g of a semi-solid residue. Purification by column chromatography on silica gel (30:1, elution with 5% to 20% MeOH/CH$_2$Cl$_2$) gave 0.30 g of a mixture of (±)-9-[4-β-(diethylphosphonomethoxy)-2-β-fluorocyclopentan-1-β-yl]guanine and (±)-9-[4-β-(diethylphosphonomethoxy)-2-β-fluoro-3-α-hydroxycyclopentan-1-β-yl]guanine.

The mixture of compounds was slurried in pyridine (12 mL) and treated with 4-(dimethylamino)pyridine (2 mg) and acetic anhydride (0.75 g, 7.3 mmol). The reaction mixture was heated at 80° C. for 8 hr., allowed to cool to room temperature, and then concentrated in vacuo. Purification by column chromatography on silica gel (30:1, elution with 5% to 20% MeOH/EtOAc) afforded 0.16 g of pure product (25% yield from (±)-9-[4-β-diethylphosphonomethoxy)-2-β-fluoro-3-α-hydroxycyclopentan-1-β-yl]guanine).

$^1$H NMR (DMSO-d$_6$): 11.88 (br s, 1H, NH), 8.07 (d, J=1.6 Hz, 1H, H-8), 5.13 (dm, J=54 Hz, 1H, H-2'), 4.57–4.72 (m, 1H, H-1'), 4.19–4.26 (m, 1H, H-4'), 4.05 (apparent quintet, J=7 Hz, 4H, 2×POCH$_2$), 3.82 (d, J=9 Hz, 2H, OCH$_2$P), 2.66 (ddd, J=6,6,12 Hz, 1H, H-5'a), 2.26–2.49 (m, 2H, H-5'b and H-3'a), 2.16 (s, 3H, CH$_3$C=O), 1.97–2.13 (m, 1H, H-3'b), and 1.24 (t, J=7 Hz, 6H, 2×POCH$_2$CH$_3$). $^{13}$C NMR (DMSO-d$_6$): 173.54 (C=O), 154.95, 148.76, 147.82, 138.78 (C-8), 119.88 (C-5), 92.43 (d, J=182 Hz, C-2'), 77.94 (d, J=14 Hz, C-4'), 62.40 (d, J=164 Hz, OCH$_2$P), 61.85 (d, J=6 Hz, POCH$_2$), 55.22 (d, J=18 Hz, C-1'), 36.90 (d, J=19 Hz, C-3'), 33.81 (C-5'), 22.84 (CH$_3$—C=O), and 16.35 (d, J=5 Hz, POCH$_2$CH$_3$). MS (FAB): 446 [MH$^+$].

EXAMPLE PP

(±)-9-[4-β-(Dihydroxyphosphonomethoxy)-2-β-fluorocyclopentan-1-β-yl]guanine

Bromotrimethylsilane (0.41 g, 2.7 mmol) was added dropwise to a solution of (±)-N$^2$-acetyl-9-[4-β-(diethylphosphonomethoxy)-2-β-fluorocyclopentan-1-β-yl]guanine (0.15 g, 0.34 mmol) in anhydrous DMF (3 mL) at room temperature under argon and the mixture was stirred for 18 hr. Concentration in vacuo gave a residue which was concentrated once from water (10 mL) and then dissolved in conc. NH$_4$OH (8 mL). After 18 hr. at room temperature, the clear solution was concentrated in vacuo and the residue was dissolved in water (50 mL). The aqueous solution was extracted with CH$_2$Cl$_2$ (20 mL) and the residue obtained upon removal of the water in vacuo was purified by column chromatography on C$_{18}$ adsorbent (20:1, elution with water). Fractions containing the product were pooled and concentrated to give a white solid. The solid was dissolved in water (2 mL) and treated with acetone (20 mL). The resulting slurry was stirred for 4 hr., and then the solid was collected by filtration to provide 0.10 g (82%) of the desired product as a white solid.

Analysis: C$_{11}$H$_{15}$N$_5$O$_5$PF.NH$_3$.H$_2$O: (calc'd): C: 34.57, H: 5.28, N: 21.99. (found): C: 34.56, H: 5.20, N: 21.05.

$^1$H NMR (D$_2$O): 8.07 (br s, 1H, H-8), 5.09 (dm, J=54 Hz, 1H, H-2'), 4.58–4.80 (m, 2H, H-1' and H-4'), 4.28 (d, J=8 Hz, 2H, OCH$_2$P), 2.70 (ddd, J=7,7,14 Hz, 1H, H-5'a), and 2.09–2.48 (m, 3H, H-5'b, H-3'a, and H-3'b).

$^{13}$C NMR (D$_2$O): 161.02, 156.61, 142.00 (C-8), 117.05 (C-5), 96.15 (d, J=180 Hz, C-2'), 81.05 (d, J=12 Hz, C-4'), 67.86 (d, J=157 Hz, OCH$_2$P), 58.13 (d, J=18 Hz, C-1'), 39.54 (d, J=20 Hz, C-3'), and 37.02 (C-5'). MS (FAB): 348 (MH$^+$).

EXAMPLE QQ

(±)-N$^6$-Monomethoxytrityl-9-(4-β-hydroxycyclopent-2-en-1-β-yl)adenine

A slurry of (±)-9-(4-β-hydroxycyclopent-2-en-1-β-yl)adenine (2.0 g, 9.2 mmol), Example X, in anhydrous pyridine (20 mL) was treated with (dimethylamino)pyridine (0.05 g) and monomethoxytrityl chloride (3.4 g, 11 mmol) at room temperature under argon. The reaction mixture was stirred for 20 hr. and then poured into a separatory funnel containing EtOAc (200 mL) and water (75 mL). The layers were agitated and separated, and the organic phase was washed with saturated NaNCO$_3$ solution (75 mL) and saturated NaCl solution (75 mL), dried over NaSO$_4$, filtered, and concentrated to give 5.2 g of a yellow foam. The residue was purified by column chromatography on silica gel (25:1, gradient elution with 1% to 5% MeOH/CH$_2$Cl$_2$) to provide 1.31 g (29%) of the product as a white foam. In addition to the desired product (R$_f$=0.61), 2.15 g (31%) of the N$^6$,O$^{4'}$-bistrityl product (R$_f$=0.84) and 1.25 g (28%) of the O$^{4'}$-monotrityl product (R$_f$=0.25) were obtained (TLC solvent system: 5% MeOH/CH$_2$Cl$_2$).

$^1$H NMR (300 MHz, DMSO-d$_6$): 8.14 (s, 1H, H-2), 7.91 (s, 1H, H-8), 7.15–7.37 (m, 13H, ArH and NH), 6.82 (d, 2H, ArH, J=9 Hz), 6.15 (m, 1H, H-3'), 5.95 (dd, 1H, H-2', J=1.5 Hz), 5.48 (d, 1H, —OH, J=7 Hz), 5.42 (m, 1H, H-1'), 4.69 (m, 1H, H-4'), 3.69 (s, 3H, OCH$_3$), 2.85 (ddd, 1H, H-5'a, J=6,6,14 Hz), and 1.72 (ddd, 1H, H-5'b, J=4,4,14 Hz). $^{13}$C NMR (75 MHz, DMSO-d$_6$): 157.80 (C-6), 153.63 (C-2), 151.03 (C-4), 148.18, 145.25 (ArC), 140.00 (C-3'), 139.56 (C-8), 137.19 (ArC), 130.72 (C-2'), 129.94, 128.58, 127.77, 126.60 (ArC), 120.76 (C-5), 113.07 (ArC), 73.83 (C-4'), 70.00 (CAr$_3$), 57.32 (C-1'), 55.06 (OCH$_3$), and 41.29 (C-5').

Mass spectrum (FAB/NOBA/LRP), m/e (rel intensity): 490 (MH$^+$ +1, 10), 273 (40).

EXAMPLE RR

(±)-N$^6$-Monomethoxytrityl-9-[4-β-(diethylphosphonomethoxy)cyclopent-2-en-1-β-yl]adenine Sodium hydride (0.12 g, 80% dispersion in oil, 4.0 mmol) was added in one portion to a solution of (±)-N$^6$-monomethoxytrityl-9-(4-β-hydroxycyclopent-2-en-1-β-yl)adenine (1.0 g, 2.0 mmol), Example QQ, and diethyl (p-toluenesulfonyloxymethyl)phosphonate (0.99 g, 3.1 mmol) cooled to −20° C. in anhydrous DMF (15 mL) under argon. The reaction mixture was stirred at −20° C. for 1 hr. and then allowed to warm to room temperature. After 4 hr., the mixture was poured into a separatory funnel containing EtOAc (80 mL) and water (20 mL). The layers were agitated and separated, and the organic phase was washed with saturated NaHCO$_3$ solution (20 mL) and saturated NaCl solution (20 mL), dried over anhydrous Na$_2$SO$_4$, filtered, and concentrated to afford 1.4 g of a brown oil. Purification by column chromatography on silica gel (25:1, elution with 5% to 10% EtOH/EtOAc) furnished 0.32 g (32%) of recovered starting material and 0.68 g (52%) of the desired product.

$^1$H NMR (300 MHz, DMSO-d$_6$): 8.04 (s, 1H, H-8), 7.90 (s, 1H, H-2), 7.15–7.31 (m, 13H, ArH and NH), 6.83 (d, 2H, ArH, J=9 Hz), 6.33–6.38 (m, 1H, H-3'), 6.18 (dd, 1H, H-2', J=2,6 Hz), 5.43–5.49 (m, 1H, H-1'), 4.61–4.67 (m, 1H, H-4'), 3.95–4.07 (m, 4H, POCH$_{2\times 2}$), 3.82–3.92 (m, 2H, OCH$_2$P), 3.70 (s, 3H, OCH$_3$), 2.77–2.87 (m, 1H, H-5'a), 1.90 (ddd, 1H, H-5'b, J=4,4,14 Hz), and 1.14–1.22 (m, 6H, POCH$_2$CH$_3$×2). $^{13}$C NMR (75 MHz, DMSO-d$_6$): 159.43 (C-6), 155.22 (C-2), 152.84 (C-4), 150.02, 146.90 (ArC), 141.19 (C-8), 138.85 (ArC), 137.19 (C-3'), 135.43 (C-2'), 131.58, 130.21, 129.42, 128.24 (ArC), 122.25 (C-5), 114.72 (ArC), 85.70 (d, C-4', J=13 Hz), 71.61 (CAr$_3$), 63.67 (d, OCH$_2$P, J=164 Hz), 63.47 (d, POCH$_2$, J=5 Hz), 58.45 (C-1'), 56.72 (OCH$_3$), 39.43 (C-5'), and 18.03 (d, POCH$_2$CH$_3$, J=5

Hz). Mass spectrum (FAB/NOBA), m/e (rel intensity): 640 (MH$^+$ +1, 45), 273 (100).

EXAMPLE SS (±)-N$^6$-Monomethoxytrityl-9-[4-β-(diethylphosphonomethoxy)-2,3-α,α-(dihydroxy)-cyclopentan-1-β-yl]adenine A solution of osmium tetroxide (0.25 g, 0.98 mmol) in anhydrous pyridine (3 mL) was added to a solution of (±)-N$^6$-monomethoxytrityl-9-[4-β-(diethylphosphonomethoxy)cyclopent-2-en-1-β-yl]adenine (0.63 g, 0.98 mmol), Example RR, in pyridine (4 mL) at room temperature under argon. After 3 hr., pyridine (5 mL) and a solution of sodium bisulfite (0.50 g) in water (8 mL) were added to the black reaction mixture. The resulting mixture was stirred for 0.5 hr., and then poured into a separatory funnel containing $CH_2Cl_2$ (80 mL) and water (20 mL). The layers were agitated and separated, and the aqueous phase was extracted with $CH_2Cl_2$ (20 mL). The combined organic layers were washed with water (10 mL) and concentrated in vacuo to give a yellow oil. The residue was concentrated from toluene (3×40 mL) to give 0.61 g (93% crude yield) of a yellow oil which could be used in subsequent reactions without purification.

$^1$H NMR (300 MHz, DMSO-d$_6$): 8.24 (s, 1H, H-2), 7.88 (s, 1H, H-8), 7.10–7.31 (m, 13H, ArH and NH), 6.84 (d, 2H, ArH, J=9 Hz), 5.12 (br s, 2H, —OH×2), 4.61–4.71 (m, 1H, H-1'), 4.42 (dd, 1H, H-2', J=5.9 Hz), 3.99–4.09 (m, 4H, POCH$_2$×2), 3.88–3.91 (m, 1H, H-3'), 3.83–3.88 (m, 2H, OCH$_2$P), 3.77–3.83 (m, 1H, H-4'), 3.70 (s, 3H, OCH$_3$), 2.47–2.59 (m, 1H, H-5'a), 1.98–2.07 (m, 1H, H-5'b), and 1.22 (t, 6H, POCH$_2$CH$_3$×2, J=7 Hz). $^{13}$C NMR (75 MHz, DMSO-d$_6$): 157.82 (C-6), 153.57 (C-2), 150.97 (C-4), 148.97, 145.29 (ArC), 140.85 (C-8), 137.22, 129.96, 129.02, 128.33, 126.64 (ArC), 120.91 (C-5), 113.12 (ArC), 84.24 (d, C-4'J=13 Hz), 74.54 (C-2'), 73.39 (C-3'), 69.96 (CAr$_3$), 62.59 (d, OCH$_2$P, J=165 Hz), 61.95 (d, POCH$_2$, J=6 Hz), 58.26 (C-1'), 55.10 (OCH$_3$), 32.98 (C-5'), and 16.45 (d, POCH$_2$CH$_3$, J=6 Hz). Mass spectrum (FAB/NOBA/LRP), m/e (rel intensity): 674 (MH$^+$ +1, 15), 273 (100).

EXAMPLE TT (±)-9-[4-β-(Diethylphosphonomethoxy)-2,3-α,α-(dihydroxy)cyclopentan-1-β-yl]adenine (±)-N$^6$-Monomethoxytrityl-9-[4-β-(diethylphosphonomethoxy)-2,3-α,α-(dihydroxy)cyclopentan-1-β-yl]adenine (0.50 g, 0.74 mmol), Example SS, was dissolved in 80% aqueous acetic acid (15 mL) and the resulting clear, yellow solution was heated on a steam bath for 15 min. The mixture was allowed to cool to room temperature and concentrated in vacuo. Concentration of the residue from water (2×25 mL) and ethanol (2×25 mL), followed by drying under high vacuum provided 0.50 g of a clear, brown oil. Purification by column chromatography on silica gel (10:1, gradient elution with 5% to 15% MeOH/CH$_2$Cl$_2$) gave 0.27 g (89%) of the desired product.

Analysis: C$_{15}$H$_{24}$N$_5$O$_6$P.0.5 H$_2$O: (calc'd): C: 43.91, H: 6.15, N: 17.07. (found): C: 43.96, H: 6.22, N: 17.19.

$^1$H NMR (300 MHz, DMSO-d$_6$): 8.13 (s, 1H, H-2), 8.10 (s, 1H, H-8), 7.21 (br s, 2H, NH$_2$), 5.14 (d, 1H, —OH, J=7 Hz), 5.10 (d, 1H, —OH, J=4 Hz), 4.60–4.71 (m, 1H, H-1'), 4.36–4.45 (m, 1H, H-2'), 3.99–4.10 (m, 4H, POCH$_2$×2), 3.89–3.94 (m, 1H, H-3'), 3.88 (d, 2H, OCH$_2$P, J=9 Hz), 3.78–3.83 (m, 1H, H-4'), 2.50–2.61 (m, 1H, H-5'a), 1.97–2.07 (m, 1H, H-5'b), and 1.23 (t, 6H, POCH$_2$CH$_3$×2, J=7 Hz). $^{13}$C NMR (75 MHz, DMSO-d$_6$): 156.09 (C-6), 152.24 (C-2), 149.81 (C-4), 140.03 (C-8), 119.28 (C-5), 84.28 (d, C-4', J=12 Hz), 74.64 (C-2'), 73.48 (C-3'), 62.56 (d, OCH$_2$P, J=164 Hz), 61.93 (d, POCH$_2$, J=6 Hz), 57.99 (C-1'), 33.04 (C-5') and 16.42 (d, POCH$_2$CH$_3$, J=6 Hz).

EXAMPLE UU (±)-9-[4-β-(Dihydroxyphosphonomethoxy)-2,3-α,α-(dihydroxy)cyclopentan-1-β-yl]adenine Bromotrimethylsilane (0.75 g, 4.9 mmol) was added dropwise to a slurry of (±)-9-[4-β-(diethylphosphonomethoxy)-2,3-α,α-(dihydroxy)cyclopentan-1-β-yl]adenine (0.19 g, 0.49 mmol), Example TT, in anhydrous acetonitrile (4 mL) at room temperature under argon. After 18 hr., the mixture was concentrated in vacuo and the solid residue was concentrated from acetonitrile (12 mL) and water (5 mL). Purification by reversed-phase column chromatography on C$_{18}$ adsorbent (0.2 g crude, 40:1, elution with water) and lyophilization gave 0.15 g (86%) of the product as a fluffy, white solid.

Analysis: C$_{11}$H$_{16}$N$_5$O$_6$P.0.75 H$_2$O. (calc'd): C: 36.83, H: 4.92, N: 19.53. (found): C: 36.75, H: 4.97, N: 19.52.

$^1$H NMR (300 MHz, DMSO-d$_6$): 8.19 (s, 1H, H-2), 8.13 (s, 1H, H-8), 7.36 (br s, 2H, NH$_2$), 5.18 (br s, 2H, OH×2) 4.61–4.72 (m, 1H, H-1'), 4.41 (dd, 1H, H-2', J=5,8 Hz), 3.92 (br d, 1H, H-4', J=4 Hz), 3.76–3.80 (m, 1H, H-3'), 3.54–3.67 (m, 2H, OCH$_2$P), 2.48–2.61 (m, 1H, H-5'a), and 1.93–2.05 (m, 1H, H-5'b). $^{13}$C NMR (75 MHz, DMSO-d$_6$): 155.72 (C-6), 151.79 (C-2), 149.78 (C-4), 140.23 (C-8), 119.14 (C-5), 84.13 (d, H-4', J=12 Hz), 74.86 (C-2'), 73.42 (C-3'), 65.05 (d, OCH$_2$P, J=162 Hz), 57.91 (C-1'), and 33.29 (C-5').

EXAMPLE VV (±)-N$^6$-Benzoyl-9-[4-β-(diethylphosphono-methoxy)-2,3-α,α-(dihydroxy)cyclopentan-1-β-yl]adenine (±)-N$^6$-Benzoyl-9-[4-β-(diethylphosphono-methoxy)cyclopent-2-en-1-β-yl]adenine (1.70 g, 3.61 mmol), prepared from the product of Example Y, was concentrated from pyridine (2×30 mL), dissolved in pyridine (20 mL), and then treated with osmium tetroxide (1.00 g, 3.93 mmol) in one portion. The reaction mixture was stirred at room temperature for 1.5 hr. Pyridine (20 mL) was added next, followed by addition of a solution of sodium bisulfite (2.0 g) in water (32 mL). The resulting mixture was stirred for 1 hr., and then poured into a separatory funnel containing CH$_2$Cl$_2$ (300 mL) and water (75 mL). The layers were agitated and separated, and the organic layer was washed with water (50 mL), dried over anhydrous Na$_2$SO$_4$, filtered, and concentrated in vacuo. The residue was concentrated from toluene (2×70 mL) and CH$_2$Cl$_2$ (1×70 mL) to give 1.8 g of a white foam. Purification by column chromatography on silica gel (25:1, gradient elution with 2% to 10% MeOH/CH$_2$Cl$_2$) furnished 1.61 g (88%) of the product as a white foam.

Analysis: C$_{22}$H$_{28}$N$_5$O$_7$P.0.25 H$_2$O. (calc'd): C: 51.82, H: 5.64, N: 13.74. (found): C: 51.70, H: 5.72, N: 13.79.

$^1$H NMR (300 MHz, DMSO-d$_6$): 11.15 (br s, 1H, NH), 8.71 (s, 1H, H-8), 8.51 (s, 1H, H-2), 8.04 (d, 2H, ArH, J=8

Hz), 7.50–7.65 (m, 3H, ArH), 5.22 (d, 1H, OH, J=7 Hz), 5.16 (d, 1H, OH, J=4 Hz), 4.79–4.88 (m, 1H, H-1'), 4.45–4.53 (m, 1H, H-2'), 4.04–4.12 (m, 4H, POCH$_2$×2), 4.00–4.03 (m, 1H, H-3'), 3.90 (d, 2H, OCH$_2$P, J=9 Hz), 3.84–3.88 (m, 1H, H-4'), 2.48–2.70 (m, 1H, H-5'a), 2.04–2.16 (m, 1H, H-5'b), and 1.24 (t, 6H, POCH$_2$C H$_3$×2). $^{13}$C NMR (75 MHz, DMSO-d$_6$): 165.73 (C=O), 152.78 (C-151.30 (C-2), 150.28 (C-4), 143.94 (C-8), 133.56, 132.52, 128.58 (ArC), 126.06 (C-5), 84.26 (d, C-4', J=13 Hz), 74.75 (C-2'), 73.42 (C-3'), 62.66 (d, OCH$_2$P, J=164 Hz), 61.99 (d, POCH$_2$, J=6 Hz), 58.35 (C-1'), 32.98 (C-5'), and 16.48 (d, POCH$_2$CH$_3$, J=5 Hz).

EXAMPLE WW 2,3-Cyclic sulfate ester of (±)-N$^6$-Benzoyl-9-[4-β-(diethylphosphonomethoxy)-2,3-α,α-(dihydroxy) cyclopentan-1-β-yl]adenine Sulfuryl chloride (5.9 mL, 1M solution in CH$_2$Cl$_2$, 5.9 mmol) was added dropwise to a solution of (±)-N$^6$-benzoyl-9-[4-β-(diethylphosphonomethoxy)-2,3-α,α-(dihydroxy) cyclopentan-1-β-yl]adenine (2.0 g, 4.0 mmol), Example VV, in CH$_2$Cl$_2$ (25 mL) cooled to 0° C. under argon. After 4.5 hr., water (50 mL) and CH$_2$Cl$_2$ (30 mL) were added, and the mixture was transferred into a separatory funnel containing CH$_2$Cl$_2$ (50 mL). The layers were agitated and separated, and the organic phase was washed with water (30 mL) and saturated NaCl solution (60 mL), dried over anhydrous Na$_2$SO$_4$, filtered, and concentrated to give 2.5 g of a white foam. The residue was purified by column chromatography on silica gel (40:1, elution with 2% to 12% EtOH/EtOAc) to afford 1.85 g (82%) of the product as a white foam.

Analysis: C$_{22}$H$_{26}$N$_5$O$_9$SP: (calc'd): C: 46.57, H: 4.62, N: 12.35. (found): C: 46.59, H: 4.39, N: 12.00. $^1$H NMR (300 MHz, DMSO-d$_6$): 11.24 (s, 1H, NH), 8.78 (s, 1H, H-8), 8.66 (s, 1H, H-2), 8.04 (d, 2H, ArH, J=8 Hz), 7.51–7.66 (m, 3H, ArH), 6.00 (dd, 1H, H-2', J=6,8 Hz), 5.65 (dd, 1H, H-3', J=5,8 Hz), 5.42 (ddd, 1H, H-1', J=8,8,11 Hz), 4.57 (ddd, 1H, H-4', J=6,6,8 Hz), 3.98–4.12 (m, 6H, OCH$_2$P and POC H$_2$×2), 2.86 (ddd, 1H, H-5'a, J=7,7, 13 Hz), 2.60 (br dd, 1H, H-5'b, J=12, 22 Hz), and 1.24 (t, 6H, POCH$_2$CH$_3$×2, J=7 Hz). $^{13}$C NMR (75 MHz, DMSO-d$_6$): 165.68 (C=O), 152.33 (C-6), 151.78 (C-2), 150.53 (C-4), 143.12 (C-8), 133.39, 132.55, 128.55 (ArC), 125.54 (C-5), 86.17 (C-2'), 85.31 (C-3'), 81.92 (d, C-4', J=13 Hz), 63.13 (d, OCH$_2$P, J=165 Hz), 62.04 (d, POCH$_2$, J=5 Hz), 55.85 (C-1'), 31.99 (C-5'), and 16.37 (d, POCH$_2$CH$_3$, J=5 Hz).

EXAMPLE XX (±)-9-[4-β-(Diethylphosphonomethoxy)-2-β-fluoro-3-α-hydroxycyclopentan-1-β-yl]adenine Anhydrous tetrabutylammonium fluoride (0.28 g, 1.1 mmol) was added in one portion to a 0° C. solution of the 2,3-cyclic sulfate ester of (±)-N$^6$-benzoyl-9-[4-β-(diethylphosphonomethoxy)-2,3-α,α-(dihydroxy) cyclocyclopentan-1-β-yl]adenine (0.40 g, 0.70 mmol), Example WW, in acetone (6 mL) under argon. The reaction mixture was stirred at 0° C. for 2 hr., then allowed to warm to room temperature, and stirred further for 20 hr. The solvent was removed in vacuo and the residue was partitioned between CH$_2$Cl$_2$ (75 mL) and water (25 mL). The organic layer was washed with saturated NaHCO$_3$ solution (25 mL) and saturated NaCl solution (25 mL), dried over anhydrous Na$_2$SO$_4$, filtered, and concentrated to afford 0.66 g of a viscous, clear oil. Purification by column chromatography on silica gel (50:1, gradient elution with 1% to 10% MeOH/CH$_2$Cl$_2$) gave 430 mg of material contaminated with tetrabutylammonium fluoride.

The partially-purified material (350 mg) was dissolved in 1N HCl solution (10 mL) and heated at 80° C. for 24 hr. The mixture was allowed to cool to room temperature and then concentrated in vacuo. The residue was concentrated from water (2×30 mL) and purified by column chromatography on silica gel (50:1, gradient elution with 2% to 15% MeOH/ CH$_2$Cl$_2$) to provide 0.12 g of the product (50% overall yield from the cyclic sulfate).

Analysis: C$_{15}$H$_{23}$N$_5$O$_5$FP.0.25 H$_2$O. (calc'd): C: 44.18, H: 5.81, N: 17.18. (found): C: 44.14, H: 6.02, N: 17.32. $^1$H NMR (300 MHz, DMSO-d$_6$): 8.25 (s, 1H, H-8), 8.16 (s, 1H, H-2), 7.30 (br s, 2H, NH$_2$), 5.84 (d, 1H, OH, J=5 Hz), 4.91–5.07 (m, 1H, H-1'), 4.89 (dm, 1H, H-2', J=52 Hz), 4.16–4.20 (m, 1H, H-3'), 4.02–4.14 (m, 4H, POCH$_2$×2), 3.89–3.98 (m, 3H, OCH$_2$P and H-4'), 2.67–2.78 (m, 1H, H-5'a), 2.40–2.52 (m, 1H, H-5'b), and 1.27 (t, 6H, POCH$_2$C H$_3$×2, J=7 Hz). $^{13}$C NMR (75 MHz, DMSO-d$_6$): 156.09 (C-6), 152.58 (C-2), 149.66 (C-4), 139.96 (C-8), 118.60 (C-5), 96.00 (d, C-2', J=185 Hz), 85.15 (d, C-4', J=10 Hz), 78.41 (d, C-3', J=25 Hz), 62.93 (d, OCH$_2$P, J=165 Hz), 61.94 (d, POCH$_2$, J=6 Hz), 52.39 (d, C-1', J=19 Hz), 32.15 (C-5'), and 16.39 (d, POCH$_2$CH$_3$, J=6 Hz).

EXAMPLE YY (±)-9-[4-β-(Dihydroxyphosphonomethoxy)-2-β-fluoro-3-α-hydroxycyclopentan-1-β-yl]adenine Bromotrimethylsilane (0.64 g, 4.2 mmol) was added dropwise to a slurry of (±)-9-[4-β-(diethylphosphonomethoxy)-2-β-fluoro-3-α-hydroxycyclopentan-1-β-yl]adenine (0.21 g, 0.52 mmol), Example XX, in anhydrous acetonitrile (5 mL) under argon. Anhydrous DMF (0.7 mL) was added, and the slurry was stirred at room temperature for 20 hr. Concentration of the reaction mixture in vacuo provided a yellow oil. The residue was concentrated from acetonitrile (2×20 mL), placed under high vacuum for 3 hr., and then treated with water (3 mL). The resulting white slurry was stirred at room temperature for 1 hr. and then acetone (15 mL) was added. The precipitate was collected by filtration and dried under high vacuum for 18 hr. to furnish 0.15 g (83%) of the product as a white solid.

Analysis: C$_{11}$H$_{15}$N$_5$O$_5$FP.1.5 H$_2$O. (calc'd): C: 35.31, H: 4.85, N: 18.72. (found): C: 35.17, H: 4.75, N: 18.37. $^1$H NMR (300 MHz, D$_2$O): 8.40 (d, 1H, H-8, J=2 Hz), 8.08 (s, 1H, H-2), 4.88–5.07 (m, 1H, H-1'), 4.86 (dm, 1H, H-2', J=33 Hz), 4.27 (ddd, 1H, H-3', J=3,3,22 Hz), 3.84–3.93 (m, 1H, H-4'), 3.50–3.62 (m, 2H, OCH$_2$P), 2.77–2.88 (m, 1H, H-5'a), and 2.19–2.38 (m, 1H, H-5'b). $^{13}$C NMR (75 MHz, D$_2$O): 158.17 (C-6), 155.15 (C-2), 151.80 (C-4), 144.56 (C-8), 120.86 (C-5), 100.12 (d, C-2', J=186 Hz), 88.87 (d, C-4', J=4 Hz), 82.51 (d, C-3', J=23 Hz), 70.88 (d, OCH$_2$P, J=150 Hz), 56.10 (d, C-1', J=18 Hz), and 35.22 (C-5').

EXAMPLE ZZ

(+)-(1R,4S)-cis-1-Acetoxy- 4-(methoxyethoxymethoxy)cyclopent-2-ene

A solution of (+)-(1R,4S)-cis-1-acetoxy-4-hydroxycyclopent-2-ene (see Deardorff, D. R.; Matthews, A. J.; McMeekin, D. S.; Craney, C. L. *Tetrahedron Lett.* (1986), 27, 1255) (7.62 g, 53.6 mmol) in anhydrous $CH_2Cl_2$ (100 mL) under argon was cooled to 0° C. and treated in one portion with methoxyethoxymethyl chloride (10.0 g, 80.4 mmol). The cooled solution was treated dropwise over 5 min with diisopropylethylamine (13.9 g, 107 mmol) and then allowed to warm to room temperature. After 14 hr., additional methoxyethoxymethyl chloride (3.3 g, 26.8 mmol) was added. The mixture was stirred at room temperature for 4 hr. and then poured into a separatory funnel containing water (100 mL). The layers were agitated and separated, and the aqueous layer was extracted with $CH_2Cl_2$ (100 mL). The combined organic layers were washed with saturated $NaHCO_3$ solution (75 mL) and saturated NaCl solution (75 mL), dried over anhydrous $MgSO_4$, filtered, and concentrated to provide 13.5 g of a clear, yellow oil. Purification by column chromatography on silica gel (20:1, gradient elution with 10% to 40% EtOAc/hexanes) provided 11.5 g (93%) of the product as a clear, colorless oil.

Analysis: $C_{11}H_{18}O_5$: (calc'd): C: 57.38, H: 7.88. (found): C: 57.33, H: 8.09. $^1H$ NMR (300 MHz, $CDCl_3$): 6.10–6.13 (m, 1H, H-2'), 5.96–5.99 (m, 1H, H-3'), 5.46–5.50 (m, 1H, H-1'), 4.78 (s, 2H, $OCH_2O$), 4.57–4.61 (m, 1H, H-4'), 3.63–3.77 (m, 2H, $OCH_2$), 3.55 (t, J=5 Hz, 2H, $OCH_2$), 3.38 (s, 2H, $OCH_3$), 2.77 (ddd, J=7, 7, 15 Hz, 1H, H-5'a), and 1.70 (ddd, J=4, 4, 14 Hz, 1H, H-5'b). $^{13}C$ NMR (75 MHz, $CDCl_3$): 170.70 (C=O), 136.53 and 132.72 (C-2' and C-3'), 94.81 ($OCH_2O$), 79.89 (C-4'), 76.61 (C-1'), 71.59 and 66.83 ($OCH_2CH_2O$), 58.89 ($CH_3O$), 37.84 ($CH_3C$=O), and 21.03 (C-5'). MS (DCl-isobutane): 231 ($MH^+$) 125 (100%). $[\alpha]^{20}_D$: +37.5 (c=0.79, $CHCl_3$).

EXAMPLE AAA

(+)-(1R,4S)-cis-1- Acetoxy-4-(diethylphosphonomethoxy)cyclopent-2-ene

Dimethylboron bromide (16.4 g, 136 mmol) was added dropwise over 10 min to a solution of (+)-(1R,1S)-cis-1-acetoxy-4-(methoxyethoxymethoxy)cyclopent-2-ene (10.1 g, 43.9 mmol), Example ZZ, in anhydrous $CH_2Cl_2$ (75 mL) at −78° C. under argon. The reaction mixture was stirred at −78° C. for 1.5 hr., then triethyl phosphite (32.8 g, 197 mmol) was added dropwise over 10 min, and the solution was allowed to warm to room temperature over 2 hr. After 3 hr., the reaction mixture was diluted with $CH_2Cl_2$ (150 mL), washed with water (75 mL) and saturated NaCl solution (75 mL), dried over anhydrous $MgSO_4$, filtered, and concentrated in vacuo. The residue was kept under high vacuum for 24 hr. to give 28.5 g of a yellow oil. Purification by column chromatography on silica gel (20:1, elution with 70% to 90% to 100% EtOAc/hexanes) provided 5.91 g (46%) of pure product, along with 4.58 g of slightly impure material. Repurification of the impure fractions provided an additional 3.88 g (30%) of pure product. The total yield of the desired product was 76%.

Analysis: $C_{12}H_{21}O_6P$: (calc'd): C: 49.32, H: 7.25. (found): C: 49.13, H: 7.15. $^1H$ NMR (300 MHz, $CDCl_3$): 6.08–6.11 (m, 1H, H-2'), 5.99–6.02 (m, 1H, H-3'), 5.44–5.48 (m, 1H, H-1'), 4.56–4.59 (m, 1H, H-4'), 4.12 (apparent quintet, J=7 Hz, 4H, 2×$POCH_2$), 3.75 (d, J=9 Hz, 2H, $OCH_2P$), 2.73 (ddd, J=7, 7, 14 Hz, 1H, H-5'a), 2.01 (s, 3H, $CH_3C$=O), 1.69 (ddd, J=4,4,14 Hz, 1H, H-5'b), and 1.31 (t, J=7 Hz, 6H, 2×$POCH_2CH_3$). $^{13}C$ NMR (75 MHz, $CDCl_3$): 170.57 (C=O), 135.05 and 133.88 (C-2' and C-3'), 83.61 (d, J=12 Hz, C-4'), 76.35 (C-1'), 62.36 (d, J=4 Hz, $POCH_2$), 61.84 (d, J=170 Hz, $OCH_2P$), 36.42 ($CH_3C$=O), 20.94 (C-5'), and 16.32 (d, J=6 Hz, $POCH_2CH_3$). MS (DCl-isobutane): 293 ($MH^+$), 233 (100%, $MH^+$−HOAc), $[\alpha]^{20}_D$: +3.25 (c=0.80, $CHCl_3$).

EXAMPLE BBB

(−)-4-O-Methyl-1-[(1R,4S)-4-β-(diethylphosphonomethoxy)cyclopent- 2-en-1-β-yl]thymine A slurry of 4-O-methylthymine (1.05 g, 7.50 mmol) in anhydrous DMF (30 mL) was treated under argon with NaH (0.23 g, 80% dispersion in oil, 7.50 mmol) in one portion. Within 1 hr., the consistency of the reaction mixture changed from freely-moving to very thick. Treatment of the slurry with triphenylphosphine (0.18 g, 0.75 mmol) was followed by rapid addition of a solution of (+)-(1R,4S)-cis-1-acetoxy-4-(diethylphosphonomethoxy)cyclopent-2-ene (2.00 g, 6.80 mmol), Example AAA, in DMF (95 mL). Finally, tetrakis(triphenylphosphine)palladium (0) (0.40 g, 0.35 mmol) was added in one portion, and the reaction vessel was immediately placed in an oil bath preheated to 55° C. After 45 min, the reaction mixture was allowed to cool to room temperature and insoluble material was removed by filtration. Concentration of the filtrate provided 3.0 g of a brown, viscous residue which was purified by column chromatography on silica gel (20:1, elution with 1% to 2% to 3% MeOH/$CH_2Cl_2$) to afford 1.48 g (58%) of the product as a viscous oil.

Analysis: $C_{16}H_{25}N_2O_6P \cdot 0.66 H_2O$: (calc'd): C: 50.02, H: 6.91, N: 7.29. (found): C: 50.21, H: 7.13, N: 6.82. $^1H$ NMR (300 MHz, DMSO-$d_6$): 7.44 (s, 1H, H-6), 6.33–6.36 (m, 1H, H-2'), 5.99–6.01 (m, 1H, H-3'), 5.48–5.51 (m, 1H, H-1'), 4.54–4.56 (m, 1H, H-4'), 3.94–4.07 (m, 4H, 2×$POCH_2$), 3.83–3.90 (m, 2H, $OCH_2P$), 2.73 (ddd, J=8, 8, 16 Hz, 1H, H-5'a), 1.86 (s, 3H, $CH_3$), 1.52 (ddd, J=4, 4, 15 Hz, 1H, H-5'b), and 1.18–1.24 (m, 6H, 2×$POCH_2CH_3$). $^{13}$NMR (75 MHz, DMSO-$d_6$): 169.59 (C-4), 155.22 (C-2), 141.94 (C-6), 135.96 (C-3'), 134.19 (C-2'), 103.29 (C-5), 83.96 (d, J=14 Hz, C-4'), 62.08 (d, J=165 Hz, $OCH_2P$), 61.75 (d, J=6 Hz, $POCH_2$), 59.04 (C-1'), 54.00 ($OCH_3$), 37.18 (C-5'), 16.31 (d, J=5 Hz, $POCH_2CH_3$), and 11.74 ($CH_3$). MS (DCl-isobutane): 373 ($MH^+$). $[\alpha]^{20}_D$: −20.73 (c=1.64, MeOH).

EXAMPLE CCC

(+)-1-[(1R,4S)-4-β- Diethylphosphonomethoxy) cyclopent-2-en-1-β-yl]thymine (−)-4'-O-Methyl-1-[(1R,4S)-4-β- (diethylphosphonomethoxy) cyclopent-2-en-1-β-yl]thymine (1.40 g, 3.76 mmol), Example BBB, was dissolved in 2:1 EtOH/$H_2O$ (30 mL) and treated with concentrated HCl (0.2 mL). The solution was stirred at room temperature for 18 hr., at 50° C. for 2 hr., and then allowed to cool to room temperature. Concentration in vacuo gave a yellow residue which was further concentrated from $H_2O$ (2×15 mL) to afford 1.33 g of a viscous semi-solid. Column chromatography on silica gel (20:1, elution with 2% to 3% to 5% EtOH/EtOAc) provided 1.00 g (74%) of the product as an off-white solid.

Analysis:: $C_{15}H_{23}N_2O_6P$: (calc'd): C: 50.28, H: 6.47, N, 7.82. (found): C: 50.20, H: 6.52, N: 7.66. $^1H$ NMR (300 MHz, DMSO-$d_6$): 11.27 (s, 1H, NH), 7.14 (d, J=1 Hz, 1H, H-6), 6.32–6.35 (m, 1H, H-2'), 5.96–5.98 (m, 1H, H-3'), 5.39–5.42 (m, 1H, H-1'), 4.51–4.53 (m, 1H, H-4'), 3.97–4.07 (m, 4H, 2×PO$CH_2$), 3.85–3.92 (m, 2H, O$CH_2$P), 2.67 (ddd, J=8, 8, 16 Hz, 1H, H-5'a), 1.73 (s, 3H, $CH_3$), 1.55 (ddd, J=3, 3, 15 Hz, 1H, H-5'b), and 1.18–1.24 (m, 6H, 2×POC$H_2$C$H_3$). $^{13}C$ NMR (75 MHz, DMSO-$d_6$): 163.83 (C-4), 150.82 (C-2), 136.97 (C-6), 135.93 (C-3'), 134.04 (C-2'), 109.50 (C-5), 83.91 (d, J=14 Hz, C-4'), 62.10 (d, J=165 Hz, O$CH_2$P), 61.75 (d, J=6 Hz, PO$CH_2$), 57.58 (C-1'), 36.50 (C-5'), 16.33 (d, J=5 Hz, POCH$_2$$CH_3$), and 12.19 ($CH_3$). MS (FAB/NOBA/LRP): 359 (MH$^+$), 3.91, 169. $[\alpha]^{20}_D$: +27.54 (c=1.14, $CH_3OH$).

EXAMPLE DDD (+) -1-[(1R,4S) -4-β)-Dihydroxyphosphonomethoxy)cyclopent-2-en-1-β-yl]thymine Bromotrimethylsilane (2.25 g, 14.7 mmol) was added dropwise over 5 min to a solution of (+)-1-[(1R,4 S)-4-β-(diethylphosphonomethoxy)cyclopent-2-en-1- β-yl] thymine (0.526 g, 1.47 mmol), Example CCC, in anhydrous DMF (10 mL) at room temperature under argon. The resulting yellow solution was stirred for 16 hr. and then concentrated in vacuo. The residue was placed under high vacuum for 8 hr. and then concentrated from $H_2O$ (10 mL). The residue was dissolved in $H_2O$ (10 mL), treated with conc. $NH_4OH$ (2 mL), and concentrated in vacuo to provide 0.70 g of a pale yellow solid. Purification by column chromatography on $C_{18}$ adsorbent (40:1, elution with $H_2O$) gave 0.47 g (98%) of the product as a glass.

Analysis: $C_{11}H_{15}O_6P.NH_3.0.33$ $H_2O$: (calc'd): C: 40.62, H: 5.78, N: 12.92. (found): C: 40.54, H: 5.91, N: 13.15. $^1H$ NMR (300 MHz, $D_2O$): 7.36 (d, J=1 Hz, 1H, H-6), 6.26–6.29 (m, 1H, H-2'), 5.86–5.89 (m, 1H, H-3'), 5.37–5.41 (m, 1H, H-1'), 4.60–4.63 (m, 1H, H-4'), 3.53–3.66 (m, 2H, O$CH_2$P), 2.83 (ddd, J=8, 8, 16 Hz, 1H, H-5'a), 1.77 (s, 3H, $CH_3$), and 1.57 (ddd, J=5.5,15 Hz, 1H, H-5'b). $^{13}C$ NMR (75 MHz, $D_2O$), 169.41 (C-4), 155.01 (C-2), 142.21 (C-6), 139.38 (C-3'), 135.38 (C-2'), 114.07 (C-5), 86.95 (d, J=12 Hz, C-4'), 67.73 (d, J=155 Hz, O$CH_2$P), 61.81 (C-1'), 39.21 (C-5'), and 14.07 ($CH_3$). MS (FAB/GLY): 320 (MH$^+$ for ammonium salt), 303 (MH+). $[\alpha]^{20}_D$: +4.15 (c=1.47, $H_2O$).

EXAMPLE EEE (+)-6-O-Benzyl-9-[(1R,4 S)-4-β-hydroxycyclopent-2-en-1-β-yl]guanine Sodium hydride (0.058 g, 80% dispersion in oil, 1.94 mmol) was added in one portion to a solution of 6- O-benzylguanine (0.467 g, 1.94 mmol) in anhydrous DMF (3 mL) at room temperature under argon, and the solution was stirred for 0.5 hr. Meanwhile, a mixture of triphenylphosphine (0.046 g, 0.17 mmol) and (+)-(1R,4 S)-cis-1-acetoxy-4-hydroxycyclopent-2-ene (see Deardorff, D. R.; Matthews, A. J.; McMeekin, D. S.; Craney, C. L. *Tetrahedron Lett.* (1986) 27, 1255) (0.250 g, 1.76 mmol) in anhydrous DMF (5 mL) was degassed by placing the mixture under high vacuum for 30 sec, followed by introduction of argon. This procedure was repeated 3 times, and then tetrakis(triphenylphosphine)palladium (0) (0.101 g, 0.087 mmol) was added. The reaction mixture was placed in an oil bath preheated to 65° C. and the solution of the sodium salt of 6-O-benzylguanine was added dropwise via cannula over 3 min. The reaction mixture was stirred at 65° C. for 1 hr., then allowed to cool to room temperature, and treated with MeOH (5 mL). Evaporation of the solvent in vacuo gave 1.1 g of a brown, semi-solid residue. Purification by column chromatography on silica gel (20:1, elution with 3% MeOH/$CH_2Cl_2$) provided 0.460 g (81%) of the product as a white solid. The NMR data is the same as that for the product of Example DD. $[\alpha]^{20}_D$: +50.1 (c=0.63, MeOH).

EXAMPLE FFF $N^2$-Monomethoxytrityl-6-O-benzyl-9-[(1R,4 S)-4-β-(hydroxycyclopent-2-en-1-β-yl)]guanine The product is prepared by reacting the product of Example EEE according to the procedure described in Example EE.

EXAMPLE GGG (−)-$N^2$-Monomethoxytrityl-6-O-benzyl-9-[(1R,4 S)-4-β-diethylphosphonylmethoxycyclopent-2-en-1- β-yl]guanine The product is prepared by reacting the product of Example FFF according to the procedure described in Example FF.

EXAMPLE HHH (−)-6-O-Benzyl-9-[(1R,4 S)-4-β-(diethylphosphonomethoxy)cyclopent-2-en-1- β-yl]guanine A solution of 6-O-benzylguanine (6.84 g, 28.4 mmol) in anhydrous DMF (100 mL) under argon was treated in one portion with NaH (0.85 g, 80% dispersion in oil, 28.4 mmol). The reaction mixture was stirred at room temperature for 1 hr., then triphenylphosphine (0.68 g, 2.60 mmol) was added, followed by rapid addition of a solution of (+)-(1 R,4 S)-cis-1-acetoxy-4-(diethylphosphonomethoxy)cyclopent-2-ene (7.54 g, 25.8 mmol), Example AAA, in DMF (10 mL). Finally, tetrakis(triphenylphosphine)palladium (0) (1.49 g, 1.30 mmol) was added in a single portion, and the reaction vessel was immediately placed in an oil bath pre-heated to 65° C. After 1 hr., the reaction mixture was allowed to cool to room temperature and insoluble material was removed by filtration. The filtrate was concentrated in vacuo and the residue was dissolved in MeOH (20 mL). Additional insoluble material was removed by filtration. Concentration of the filtrate provided 17 g of a dark brown oil. Purification by column chromatography on silica gel (20:1, elution with 2.5% to 3% MeC, H/$CH_2Cl_2$) gave 7.26 g (60%) of the product.

Analysis: $C_{22}H_{28}N_5O_5P.0.5$ $H_2O$: (calc'd): C: 54.76, H: 6.06, N: 14.52. (found): C: 54.61, H: 5.70, N: 14.61.

¹H NMR (300 MHz, DMSO-d₆): 7.67 (s, 1H, H-8), 7.30–7.50 (m, 5H, ArH), 6.45 (br s, 2H, NH₂), 6.33–6.35 (m, 1H, H-2'), 6.15 (dd, J=2, 6 Hz, 1H, H-3'), 5.48 (s, 2H, OCH₂Ph), 5.31–5.34 (m, 1H, H-1'), 4.62–4.64 (m, 1H, H-4'), 3.97–4.07 (m, 4H, 2×POCH₂), 3.84–3.96 (m, 2H, OCH₂P), 2.78 (ddd, J=7,7,14 Hz, 1H, H-5'a) 1.83 (ddd, J=4,4,14 Hz, 1H, H-5'b), 1.18 (t, J=7 Hz, 3H, POCH₂CH₃), and 1.16 (t, J=7 Hz, 3H, POCH₂CH₃). ¹³C NMR (75 MHz, DMSO-d₆): 161.79, 161.38, 155.67, 139.34, 138.43, 137.03, 135.70, 130.17, 130.13, 129.76, 115.56 (C-5), 85.64 (d, J=13 Hz, C-4'), 68.56 (OCH₂Ph), 63.57 (d, J=165 Hz, OCH₂P), 63.48 (d, J=6 Hz, POCH₂), 57.93 (C-1'), 39.17 (C-5'), and 18.01 (d, J=5 Hz, POCH₂CH₃). MS (DCI-isobutane): 474 (MH⁺). $[\alpha]^{20}_D$: −15.71 (c=1.03, MeOH).

EXAMPLE III (−)-9-[(1R,4S)-4-β-(Diethylphosphonomethoxy)cyclopent-2-en-1-β-yl]guanine A solution of (−)-6-O-benzyl-9-[(1R,4S)-4-β-(diethylphosphonomethoxy)cyclopent-2-en-1-β-yl]guanine, Example HHH, (0.51 g, 1.1 mmol) in 80% aqueous acetic acid (15 mL) was heated on a steam bath for 4 hr. and then concentrated in vacuo. The yellow residue was concentrated from water (1×10 mL) and then purified by column chromatography on silica gel (20:1, elution with 10% to 13% MeOH/CH₂Cl₂) to provide 0.32 g (78%) of the desired product. Analysis: C₁₅H₂₂N₅O₅P: (calc'd): C: 47.00, H: 5.79, N: 18.27. (found): C: 46.86, H: 5.74, N: 18.25. ¹H and ¹³C NMR are the same as that for the product of Example GG. $[\alpha]^{20}_D$: −2.37 (c=0.88, MeOH).

EXAMPLE JJJ (−)-9-[(1R,4S)-4-β-Dihydroxyphosphonomethoxycyclopent-2-en-2-β-yl]guanine The product is prepared by reacting the product of Example III according to the procedure described in Example HH.

EXAMPLE KKK (−)-N²-Pivaloyl-6-O-benzyl-9-[(1R,4S)-4-β-(diethylphosphonomethoxy)cyclopent- 2-en-1-β-yl]guanine A solution of (−)-6-O-benzyl-9-[(1R,4S)-4-β-(diethylphosphonomethoxy)cyclopent-2-en-1-β-yl]guanine (0.95 g, 2.0 mmol), Example HHH, in anhydrous pyridine (10 mL) at room temperature under argon was treated with 4-(dimethylamino)pyridine (0.02 g) and pivaloyl chloride (0.36 g, 3.0 mmol). After 1 hr., additional pivaloyl chloride (0.12 g, 1.0 mmol) was added, and the slurry was stirred for 1 hr. further. The reaction mixture was treated with methanol (10 mL) and then concentrated in vacuo to give 1.8 g of a semi-solid residue. Purification by column chromatography on silica gel (20:1, elution with 2% to 3% to 4% MeOH/CH₂Cl₂) gave 1.1 g (98%) of the product.

Analysis: C₂₇H₃₆N₅O₆P.0.25 H₂O: (calc'd): C: 57.69, H: 6.55, N: 12.46. (found): C: 57.71, H: 6.47, N: 12.28.

¹H NMR (300 MHz, DMSO-d₆): 9.89 (s, 1H, NH), 8.03 (s, 1H, H-8), 7.52–7.57 (m, 2H, ArH), 7.31–7.41 (m, 3H, ArH), 6.39–6.42 (m, 1H, H-2'), 6.20–6.22 (m, 1H, H-3'), 5.62 (s, 2H, OCH₂Ph), 5.48–5.51 (m, 1H, H-1'), 4.63–4.66 (m, 1H, H-4'), 3.96–4.07 (m, 4H, 2×POCH₂), 3.87–3.94 (m, 2H, OCH₂P), 2.82 (ddd, J=7, 7, 14 Hz, 1H, H-5'a), 1.90 (ddd, J=3, 3, 15 Hz, 1H, H-5'b), 1.24 (s, 9H, t Bu), and 1.17–1.23 (m, 6H, 2×POCH₂CH₃). ¹³C NMR (75 MHz, DMSO-d₆): 175.74 (C=O), 159.63, 152.66, 152.18, 140.90, 136.34, 135.78 (C-3'), 133.86 (C-2'), 128.93, 128.47, 128.29, 117.36 (C-5), 83.91 (d, J=13 Hz, C-4'), 67.83 (OCH₂Ph), 61.98 (d, J=165 Hz, OCH₂P), 61.76 (d, J=6 Hz, POCH₂), 56.57 (C-1'), 37.64 (C-5'), 26.97 (t Bu), and 16.32 (d, J=5 Hz, POCH₂CH₃). MS (FAB/NOBA): 558 (MH⁺), 390, 326. $[\alpha]^{20}_D$: −26.29 (c=1.23, MeOH).

EXAMPLE LLL (−)-N²-Pivaloyl-6-O-benzyl-9-[1R,4S)-4-β-(diethylphosphonomethoxy)-2,3-α,α-(dihydroxy)cyclopentan-1-β-yl]guanine (−)-N²-Pivaloyl-6-O-benzyl-9-[(1R,4S)-4-β-(diethylphosphonomethoxy)cyclopent-2-en-1-β-yl]guanine (1.0 g, 1.8 mmol), Example KKK, was dissolved in anhydrous pyridine (8 mL) and treated with a solution of osmium tetroxide (0.45 g, 1.8 mmol) in pyridine (2 mL) at room temperature under argon. After 3 hr., pyridine (5 mL) was added, followed by addition of a solution of sodium bisulfite (0.70 g) in water (5 mL). The mixture was stirred for 2 hr., diluted with water (50 mL) and extracted with CH₂Cl₂ (2×100 mL). The organic phase was washed with brine, dried over MgSO₄, and concentrated in vacuo to provide 1.2 g of a brown oil. The crude material was purified by column chromatography on silica gel (20:1, elution with 2% to 3% to 4% MeOH/CH₂Cl₂) to afford 0.89 g (84%) of the product as a white solid.

Analysis: C₂₇H₃₈N₅O₈P.0.33 H₂O: (calc'd): C: 54.26, H: 6.52, N: 11.72. (found): C: 54.17, H: 6.71, N: 11.72.

¹H NMR (300 MHz, DMSO-d₆): 9.85 (s, 1H, NH), 8.29 (s, 1H, H-8), 7.53–7.57 (m, 2H, ArH), 7.31–7.41 (m, 3H, ArH), 5.62 (s, 2H, OCH₂Ph), 5.33 (d, J=6 Hz, 1H, 2'-OH), 5.10 (d, J=4 Hz, 1H, 3'-OH), 4.68–4.77 (m, 1H, H-1'), 4.33–4.40 (m, 1H, H-2'), 4.03 (apparent quintet, J=7 Hz, 4H, 2×POCH₂), 3.90–3.96 (m, 1H, H-3'), 3.88 (d, J=9 Hz, 2H, OCH₂P), 3.80–3.84 (m, 1H, H-4'), 2.56–2.65 (m, 1H, H-5'a), 1.91–1.99 (m, 1H, H-5'b), 1.24 (s, 9H, t Bu), and 1.22 (t, J=7 Hz, 6H, 2×POCH₂CH₃).

¹³C NMR (75 MHz, DMSO-d₆): 175.80 (C=O), 159.62, 153.44, 151.92, 141.67, 136.38, 128.89, 128.4, 128.28, 1.17.52 (C-5), 84.11 (d, J=12 Hz, C-4'), 75.30 (C-2'), 73.48 (C-3'), 67.79 (OCH₂Ph), 62.35 (d, J=165 Hz, OCH₂P), 61.88 (d, J=6 Hz, POCH₂), 57.80 (C-1'), 33.37 (C-5'), 26.95 (t Bu), and 16.35 (d, J=6 Hz, POCH₂CH₃). MS (FAB/NOBA): 592 (MH⁺) $[\alpha]^{20}_D$: −0.43 (c=0.94, MeOH).

EXAMPLE MMM 2,3-Cyclic thiocarbonate ester of (−)-N²-Pivaloyl-6-O-benzyl-9-[(1R,4S)-4-β-(diethylphosphonomethoxy)-2,3-α,α-(dihydroxy)cyclopentan-1-β-yl]guanine To a solution of (−)-N²-pivaloyl-6-O-benzyl-9-[(1R,4S)-4-β-(diethylphosphonomethoxy)-2,3-α,α-(dihydroxy)- cyclopentan-1-β-yl]guanine (0.74 g, 1.3 mmol), Example LLL, in anhydrous $CH_2Cl_2$ (10 mL) at room temperature under argon was added 1,1'-thiocarbonyldiimidazole (0.33 g, 1.9 mmol) in one portion. After 3 hr., the reaction mixture was treated with additional 1,1'-thiocarbonyldiimidazole (0.11 g, 0.63 mmol) and stirred at room temperature for 14 hr. further. Concentration in vacuo gave 1.2 g of a bright yellow residue. Purification by column chromatography on silica gel (20:1, elution with 2% to 3% $MeOH/CH_2Cl_2$) gave 0.72 g (91%) of the desired product as a clear, colorless glass.

Analysis: $C_{28}H_{36}N_5O_8PS.0.33\ H_2O$: (calc'd): C: 52.57, H: 5.78, N: 10.95. (found): C: 52.56, H: 5.78, N: 11.07.

$^1H$ NMR (300 MHz, DMSO-$d_6$): 9.89 (s, 1H, NH), 8.37 (s, 1H, H-8), 7.54–7.57 (m, 2H, ArH), 7.32–7.42 (m, 3H, ArH), 5.93–5.97 (dd, J=4, 8 Hz, 1H, H-2'), 5.70–5.74 (dd, J=3, 8 Hz, 1H, H-3'), 5.63 (s, 2H, $OCH_2Ph$), 5.23–5.30 (m, 1H, H-1'), 4.39–4.45 (m, 1H, H-4'), 3.92–4.05 (m, 6H, 2×$POCH_2$ and $OCH_2P$), 2.61–2.70 (m, 1H, H-5'a), 2.37–2.47 (m, 1H, H-5'b), 1.25 (s, 9H, t Bu), and 1.17–1.23 (m, 6H, 2×$POCH_2CH_3$). $^{13}C$ NMR (75 MHz, DMSO-$d_6$): 190.35 (C=S), 175.75 (C=O), 159.74, 152.83, 152.16, 141.82, 136.28, 128.90, 128.49, 128.32, 117.31 (C-5), 88.13 (C-2' and C-3'), 83.62 (d, J=14 Hz, C-4'), 67.89 ($OCH_2$ Ph), 62.94 (d, J=160 Hz, $OCH_2P$), 61.94 (d, J=6 Hz, $POCH_2$), 57.17 (C-1'), 34.06 (C-5'), 26.95 (t Bu), and 16.30 (d, J=6 Hz, $POCH_2CH_3$). MS (FAB/NOBA): 634 (MH$^+$) $[\alpha]^{20}_D$: +14.59 (c=1.04, MeOH).

EXAMPLE NNN (−)-$N^2$-Pivaloyl-6-O-benzyl-9-[(1R,4S)-4-β-(diethylphosphonomethoxy)-3-α-(hydroxy) cyclopentan-1-β-yl]guanine The 2,3-cyclic thiocarbonate ester of (−)-$N^2$-pivaloyl-6-O-benzyl-9-[(1R,4S)-4-β-(diethylphosphonomethoxy)-2,3-α,α-(dihydroxy) cyclopentan-1-β-yl]guanine (0.60 g, 0.94 mmol) of Example MMM was concentrated once from toluene (10 mL) and then dissolved in toluene (10 mL) with slight warming. The solution was heated to 80° C. and treated with AIBN (0.50 g), bis(tri-n-butyl-stannyl)oxide (1.1 g, 1.9 mmol), and polymethylhydrosiloxane (1.0 mL). After 3 hr., additional stannane (0.55 g, 0.95 mmol) and siloxane (0.5 mL) were added, and the reaction mixture was stirred at 80° C. for 14 hr. further. The mixture was allowed to cool to room temperature and the solvent was removed by concentration in vacuo. The residue was dissolved in MeOH (100 mL) and washed with hexane (2×50 mL). The methanolic solution was concentrated in vacuo to provide 1.8 g of a colorless, viscous residue. Purification by column chromatography on silica gel (20:1, elution with 2% to 3% to 4% $MeOH/CH_2Cl_2$) gave 0.13 g (24%) of the desired product as a white, waxy solid.

Analysis: $C_{27}H_{38}N_5O_7P.0.33\ H_2O$: (calc'd): C: 55.76, H: 6.70, N: 12.04. (found): C: 55.73, H: 6.72, N: 11.96.

$^1H$ NMR (300 MHz, DMSO-$d_6$): 9.83 (s, 1H, NH), 8.27 (s, 1H, H-8), 7.55 (dd, J=2, 8 Hz, 2H, ArH), 7.31–7.41 (m, 3H, ArH), 5.61 (s, 2H, $OCH_2Ph$), 5.16 (d, J=4 Hz, 1H, OH), 5.07–5.16 (m, 1H, H-1'), 4.20–4.29 (m, 1H, H-3'), 4.04 (apparent quintet, J=7 Hz, 4H, 2×$POCH_2$), 3.84–3.90 (m, 3H, $OCH_2P$ and H-4'), 2.55–2.64 (m, 1H, H-5'a), 2.15–2.19 (m, 2H, H-3'a and H-3'b) 1.92–2.00 (m, 1H, H-5'b), and 1.20–1.29 (m, 15H, t Bu and 2×$POCH_2CH_3$). $^{13}C$ NMR (75 MHz, DMSO-$d_6$): 176.26 (C=O), 160.10, 152.52, 152.42, 141.75, 136.79, 129.40, 128.85, 1.28.66, 117.95 (C-5'), 87.29 (d, J=12 Hz, C-4'), 73.73 (C-3'), 67.96 ($OCH_2Ph$), 62.51 (d, J=165 Hz, $OCH_2P$), 61.95 (d, J=6 Hz, $POCH_2$), 51.35 (C-1'), 40.09 C-2'), 36.76 (C-5'), 26.99 (t Bu), and 16.32 (d, J=6 Hz, $POCH_2CH_3$) MS (FAB/NOBA): 576 (MH$^+$) $[\alpha]^{20}_D$: −2.67 (c=0.60, $CH_3OH$).

EXAMPLE OOO (+)-$N^2$-Pivaloyl-9-[(1R,4S)-4-β-(diethylphosphonomethoxy) -3-β-hydroxycyclopentan-1-β-yl]guanine A solution of (+)-$N^2$-pivaloyl-6-O-benzyl-9-[(1R,4S)-4-β-(diethylphosphonomethoxy)-3-β-hydroxycyclopentan-1-β-yl]guanine (0.28 g, 0.49 mmol), Example NNN, in 80% aqueous acetic acid (12 mL) was heated on a steam bath for 1.5 hr. The solvent was removed in vacuo, and the residue was concentrated from water (2×20 mL). Purification by column chromatography on silica gel (25:1, elution with 2% to 3% to 4% $MeOH/CH_2Cl_2$) gave 0.17 g (72%) of the product as a glass. $^1H$ NMR (300 MHz, DMSO-$d_6$): 12.17 (br s, 1H, NH), 11.08 (br s, 1H, NH), 8.03 (s, 1H, H-8), 5.13 (d, J=3 Hz, 1H, OH), 5.01–5.07 (m, 1H, H-1'), 4.18–4.26 (m, 1H, H-3'), 4.05 (apparent quintet, J=7 Hz, 4H, 2×$POCH_2$), 3.89 (d, J=9 Hz, 2H, $OCH_2P$), 3.79–3.88 (m, 1H, H-4'), 2.49–2.62 (m, 1H, H-5'a), 2.09–2.13 (m, 2H, 2×H-3'), 1.85–1.93 (m, 1H, H-5'b), and 1.21–1.26 (m, 15H, t Bu and 2×$POCH_2CH_3$). $^{13}C$ NMR (75 MHz, DMSO-$d_6$): 181.31 (C=O), 155.09 (C-6), 148.61 (C-2), 148.28 (C-4), 137.71 (C-8), 119.86 (C-5), 86.94 (d, J=12 Hz, C-4'), 73.48 (C-3'), 62.34 (d, J=165 Hz, O $CH_2P$), 61.82 (d, J=6 Hz, $POCH_2$), 51.13 (C-1'), 36.93 (C-5'), 26.37 (t Bu), and 16.36 (d, J=5 Hz, $POCH_2CH_3$). MS (FAB/NOBA): 486 (MH$^+$).

EXAMPLE PPP (+)-9-[(1R,4S)-4-β-(Dihydroxyphosphonomethoxy)-3-α-hydroxycyclopentan-1-β-yl]guanine (+)-$N^2$-Pivaloyl-9-[(1R,4S)-4-β-(diethylphosphonomethoxy)-3-α-hydroxycyclopentan-1-β-yl]guanine (0.16 g, 0.33 mmol), Example OOO, was dissolved in anhydrous DMF (3 mL) and treated with bromotrimethylsilane (0.50 g, 3.3 mmol). The reaction mixture was stirred at room temperature under argon for 14 hr. and then concentrated in vacuo. The residue was concentrated once from DMF (10 mL) and once from water (10 mL), and then dissolved in water (10 mL) and treated with conc. $NH_4OH$ solution (5 mL). The mixture was stirred at room temperature for 48 hr., then diluted with water (30 mL), and extracted with $CH_2Cl_2$ (2×30 mL). The aqueous phase was concentrated and the residue (0.16 g) was purified by column chromatography on $C_{18}$ adsorbent (50:1, elution with $H_2O$). Fractions containing the product were pooled and concentrated to 0.5 mL volume. The product was precipitated by addition of acetone (10 mL), and the product was collected by filtration to give 0.60 g (50%) of the product as a white solid.

Analysis:: $C_{11}H_{16}N_5O_6P.NH_3.0.75\ H_2O$. (calc'd): C: 35.15, H: 5.50; N: 22.36. (found): C: 35.42, H: 5.19, N:

21.84. $^1$H NMR (300 MHz, D$_2$O): 8.03 (s, 1H, H-8), 4.74–4.91 (m, 1H, H-1'), 4.36–4.46 (m, 1H, H-3'), 3.85–3.97 (m, 1H, H-4'), 3.63 (d, J=9 Hz, 2H, OCH$_2$P), 2.66 (ddd, J=6,9,15 Hz, 1H, H-5'a), 2.21–2.32 (m, 2H, H-5'b and H-2'), and 1.97 (ddd, J=5,5,14 Hz, 1H, H-2'). $^{13}$C NMR (75 MHz, D$_2$O): 165.29, 160.52, 145.05 (C-8), 121.99 (C-5), 93.65 (d, J=12 Hz, C-4'), 81.23 (C-3'), 72.34 (d, J=158 Hz, OCH$_2$P), 58.24 (C-1'), 45.01 (C-2'), and 42.63 (C-5'). MS (FAB): 346 (MH$^+$). $[\alpha]^{20}{}_D$: +11.7 (c=0.18, H$_2$O).

EXAMPLE QQQ (–)-N$^2$-Monomethoxytrityl-6-O-benzyl-9-[(1R,4S)-4-β-(diethylphosphonomethoxy)cyclopent- 2-en-1-β-yl]guanine Procedure A The procedure described in Example FF is followed except that the starting material is (–)-N$^2$-monomethoxytrityl-6-O-benzyl-9-[(1R,4S)-4-β-hydroxyclopent-2-en-1-β-yl]guanine, Example FFF. The $^1$H and $^{13}$C NMR are the same as the product of Example FF; $[\alpha]_D^{20}$: –36.9° (c=0.47 MeOH)

Procedure B

Triethylamine (3.77 g, 37.2 mmol) was added dropwise over 5 min to a solution of (–)-6-O-benzyl-9-[(1R,4S)-4-β-(diethylphosphonomethoxy)cyclopent-2-en-1-β-yl] guanine (7.05 g, 14.9 mmol), prepared as in Example HHH, monomethoxytrityl chloride (6.44 g, 20.8 mmol) and dimethylaminopyridine (0.15 g) in anhydrous DMF (50 mL) at room temperature under argon. The reaction mixture was stirred for 2 hr. and then concentrated in vacuo. The residue was partitioned between ethyl acetate (400 mL) and water (200 mL), and the organic layer was washed with saturated NaHCO$_3$ solution (200 mL) and saturated NaCl solution (200 mL), dried over anhydrous MgSO$_4$, filtered, and concentrated to give 13 g of a viscous, yellow residue. Purification by column chromatography on silica gel (20:1, elution with 2% to 4% EtOH/EtOAc) afforded 10.4 g (94%) of the product as a crisp foam. The $^1$H and $^{13}$C NMR are the same as the product of Example FF; $[\alpha]_D^{20}$: –40.2° (c=0.60, MeOH).

EXAMPLE RRR (–)-N$^2$-Monomethoxytrityl-6-O-benzyl-9-[()1R,4S-4-β-(diethylphosphonomethoxy)-2,3-α,α -(dihydroxy)cyclopentan-1-β-yl]guanine The product is prepared using the procedure described in Example II but, substituting as the starting material, the product of Example QQQ.

EXAMPLE SSS (–)-9-[(1R,4S)-4-β-(Diethylphosphonomethoxy)-2,3-α,α-(dihydroxy)cyclopentan-1-β-yl]guanine The product is prepared using the procedure described in Example JJ, but substituting, as the starting material, the product of Example RRR.

EXAMPLE TTT

9-[(1R,4S)-4-β-(Dihydroxyphosphonomethoxy)-2,3-α,α-(dihydroxycyclopentan-1-β-yl]guanine The product is prepared according to the procedure described in Example KK except the product of Example SSS is substituted as the starting material.

EXAMPLE UUU 2,3-Cyclic sulfate ester of N$^2$-monomethoxytrityl-6-O-benzyl-9-[(1R,4S)-4-β-(diethylphosphonomethoxy)-2,3-α,α-(dihydroxy)cyclopentan-1-β-yl]guanine The product is prepared according to the procedure described in Example LL except the product of Example RRR is substituted as the starting material.

EXAMPLE VVV (+)-9-[(1R,4S)-4-β-diethylphosphonomethoxy)-2-β-fluoro-3-α-hydroxycyclopentan-1-β-yl]guanine The product is prepared according to the procedure described in Example MM except that the product of Example UUU is substituted as the starting material.

EXAMPLE WWW (+)-9-[(1R,4S)-4-β-dihydroxyphosphonomethoxy)-2-β-fluoro- 3-α-hydroxycyclopentan-1-β-yl]guanine The product is prepared according to the procedure described in Example NN except that the product of Example VVV is substituted as the starting material.

EXAMPLE XXX (+)-9-[(1R,4S)-4-β-(Diethylphosphonomethoxy)cyclopent-2-en-1-β-yl]adenine A slurry of adenine (0.46 g, 3.4 mmol) in anhydrous, degassed DMF (15 mL) was treated at room temperature under argon with NaH (0.10 g, 80% dispersion in oil, 3.4 mmol) in one portion. The mixture was heated at 50° C. for 16 hr., and then the resulting thick, pale-grey slurry was allowed to cool to room temperature. The slurry was treated sequentially with triphenylphosphine (0.090 g, 0.34 mmol), (+)-(1R,4S)-cis-1-acetoxy-4-(diethylphosphonomethoxy) cyclopent-2-ene (1.0 g, 3.4 mmol), Example AAA, and tetrakis(triphenylphosphine)palladium (0) (0.20 g, 0.17 mmol). The resulting slurry was immediately placed in an oil bath preheated to 65° C., heated for 3 hr., and then allowed to cool to room temperature. Following treatment of the mixture with MeOH (15 mL), insoluble material was removed by filtration, and the filtrate was concentrated in vacuo to give 2.5 g of a dark brown semi-solid. The crude material was purified by column chromatography on silica gel (20:1, elution with a gradient of 10% to 20% MeOH/EtOAc) to afford 0.96 g (77%) of the desired product. Analysis: C$_{15}$H$_{22}$N$_5$O$_4$P.0.25 H$_2$O: (calc'd): C: 48.46, N: 18.84. (found): C: 48.35, H: 6.10, N: 18.75.

$^1$H and $^{13}$C NMR were the same as that for the product of Example Y. $[\alpha]^{20}{}_D$: +30.5 (c=1.46, MeOH).

EXAMPLE YYY

9-[(1R,4S)-4-β-Phosphonomethoxycyclopent-2-en-1-β-yl] adenine

The product is prepared according to the procedure described in Example AA except that the starting material used is that described in Example XXX.

EXAMPLE ZZZ (+)-$N^6$-Pivaloyl-9-[(1R,4S)-4-β-(diethylphosphonomethoxy)cyclopent-2-en-1-β-yl]adenine A solution of (+)-9-[(1R,4S)-4β-(diethylphosphonomethoxy)cyclopent-2-en-1-β-yl]adenine (4.25 g, 11.6 mmol), Example XXX, in anhydrous pyridine (40 mL) was treated with 4-(dimethylamino)pyridine (0.02 g) and pivaloyl chloride (2.09 g, 17.4 mmol) at room temperature under argon. After 15 hr., MeOH (20 mL) was added and the mixture was concentrated in vacuo. The viscous residue (5.5 g) was purified by column chromatography on silica gel (20:1, gradient elution with 1% to 5% MeOH/$CH_2Cl_2$) to afford 4.89 g (94%) of the desired product.

Analysis: $C_{20}H_{30}N_5O_5P$: (calc'd): C: 53.21, H: 6.70, N: 15.51. (found): C: 53.30, H: 6.72, N: 15.34. $^1$H NMR (300 MHz., DMSO-$d_6$): 10.11 (s, 1H, NH), 8.67 (s, 1H, H-8), 8.26 (s, 1H, H-2), 6.39–6.43 (m, 1H, H-3'), 6.21–6.24 (m, 1H, H-2'), 5.57–5.63 (m, 1H, H-1'), 4.66–4.70 (m, 1H, H-4'), 3.96–4.07 (m, 4H, 2×POC$H_2$), 3.91 (dd, J=4, 9 Hz, 2H, OC$H_2$P), 2.89 (ddd, J=8, 8, 15 Hz, 1H, H-5'a), 1.89–1.97 (m, 1H, H-5'b), and 1.13–1.32 (m, 15H, t Bu and 2×POC$H_2$C$H_3$). $^{13}$C NMR (75 MHz, DMSO-$d_6$): 176.26 (C=O), 151.85, 151.31, 150.31, 142.52, 135.81 (C-3'), 133.47 (C-2'), 125.67 (C-5), 83.95 (d, J=13 Hz, C-4'), 61.98 (d, J=165 Hz, OC$H_2$P), 61.79 (d, J=7 Hz, POC$H_2$), 57.01 (C-1'), 37.64 (C-5'), 26.94 (t Bu), and 16.31 (d, J=5 Hz, POCH$_2$C$H_3$). MS (isobutane-DCI): 452 (MH$^+$). [α]$^{20}_D$=+37.0 (c=1.68 CHCl$_3$).

EXAMPLE AAAA (+)-$N^6$-Pivaloyl-9-[(1R,1S)-4-β-(diethyl-phosphonomethoxy)-2,3-α,α-(dihydroxy)cyclopentan-1-β-yl]adenine (+)-$N^6$-Pivaloyl-9-[(1R,1S)-4-β-(diethylphosphonomethoxy)cyclopent-2-en-1-β-yl]adenine (4.80 g, 10.6 mmol), Example ZZZ, was concentrated from pyridine (2×60 mL), and then dissolved in pyridine (40 mL) and treated with osmium tetroxide (3.00 g, 11.7 mmol) at room temperature under argon. After 1.5 hr., additional pyridine (20 mL) was added along with a solution of sodium bisulfite (5.0 g) in water (75 mL). The mixture was stirred for 1 hr. and then poured into a separatory funnel containing $CH_2Cl_2$ (650 mL) and water (150 mL). The layers were agitated and separated, and the organic layer was washed further with water (125 mL), dried over anhydrous $Na_2SO_4$, filtered, and concentrated in vacuo. The residue was concentrated from toluene (2×150 mL) to provide 4.8 g of a yellow foam. Purification by column chromatography on silica gel (25:1, gradient elution with 2% to 10% MeOH/$CH_2Cl_2$) gave 3.75 g (73%) of the product as an off-white foam.

Analysis: $C_{20}H_{32}N_5O_7P \cdot 0.25\ H_2O$. (calc'd): C: 49.03, H: 6.69, N: 14.30. (found): C: 49.09, H: 6.75, N: 14.28.

$^1$H NMR (300 MHz, DMSO-$d_6$): 10.10 (s, 1H, NH), 8.64 (s, 1H, H-8), 8.47 (s, 1H, H-2), 5.18 (d, J=7 Hz, 1H, OH), 5.13 (d, J-4 Hz, 1H, OH), 4.80 (dd, J=9, 18 Hz, 1H, H-1'), 4.76–4.84 (m, 1H, H-2'), 4.06 (apparent quintet, J=8 Hz, 4H, 2×POC$H_2$), 3.82–3.97 (m, 4H, H-3', H-4', and OC$H_2$P), 2.61 (ddd, J=8, 8, 16 Hz, 1H, H-5'a), 2.02–2.11 (m, 1H, H-5'b), and 1.22–1.26 (m, 15H, t Bu and 2×POC$H_2$C$H_3$). $^{13}$C NMR (75 MHz, DMSO-$d_6$): 176.29 (C=O), 152.52, 151.07, 150.27, 143.65 (C-8), 126.03 (C-5), 84.13 (d, J=12 Hz, C-4'), 74.58 (C-2'), 73.30 (C-3'), 62.54 (d, J=165 Hz, OC$H_2$P), 61.87 (d, J=6 Hz, POC$H_2$), 32.84 (C-5'), 26.96 (t Bu) and 16.38 (d, J=5 Hz, POC$H_2$C$H_3$) MS (FAB): 486 (MH$^+$) [α]$^{20}_D$: −8.10 (c=1.37, CHCl$_3$).

EXAMPLE BBBB 2,3-Cyclic sulfate ester of (+)-$N^6$-Pivaloyl-9-[(1R,1S)-4-β-(diethylphosphonomethoxy)-2,3-α,α-(dihydroxy)cyclopentan-1-β-yl]adenine A solution of (+)-$N^6$-pivaloyl-9-[(1R,1S)-4-β-(diethylphosphonomethoxy)-2,3-α,α-(dihydroxy)cyclopentan-1-β-yl]adenine (3.55 g, 7.31 mmol), Example AAAA, in anhydrous $CH_2Cl_2$ (35 mL) was cooled to 0° C. and treated with triethylamine (3.70 g, 36.6 mmol). Sulfuryl chloride (13.2 mL, 1M solution in $CH_2Cl_2$, 13.2 mmol) was added dropwise and the reaction mixture was allowed to gradually warm to room temperature. After 2 hr., additional sulfuryl chloride (2.0 mL, 1M solution in $CH_2Cl_2$, 2.0 mmol) was added. The mixture was stirred for 3 hr., then treated with $CH_2Cl_2$ (100 mL) and water (35 mL), and stirred vigorously for 0.5 hr. The layers were separated, and the organic layer was washed with water (50 mL), dried over anhydrous $Na_2SO_4$, filtered, and concentrated in vacuo to give 5.0 g of a yellow foam. The crude material was purified by column chromatography on silica gel (35:1, gradient elution with 2% to 10% MeOH/$CH_2Cl_2$) to afford 3.26 g (82%) of the product.

Analysis: $C_{20}H_{30}N_5O_9PS$: (calc'd): C: 43.88, H: 5.53, N: 12.80. (found): C: 43.54, H: 5.53, N: 12.57. $^1$H NMR (DMSO-$d_6$): 10.20 (s, 1H, NH), 8.71 (s, 1H, H-8), 8.62 (s, 1H, H-2), 5.96 (dd, J=6, 8 Hz, 1H, H-2'), 5.63 (dd, J=5, 8 Hz, 1H, H-3'), 5.34–5.42 (m, 1H, H-1'), 4.51–4.58 (m, 1H, H-4'), 3.99–4.11 (m, 6H, OC$H_2$P and 2×POC$H_2$), 2.83 (ddd, J=7, 7.14 Hz, 1H, H-5'a), 2.57 dd, J=12.22 Hz, 1H, H-5'b), and 1.21–1.26 (m, 15H, t Bu and 2×POC$H_2$C$H_3$). $^{13}$C NMR (DMSO-$d_6$): 176.31 (C=O), 152.12, 151.59, 150.56, 142.87 (C-8), 125.57 (C-5), 86.10 (C-2'), 85.23 (C-3'), 81.85 (d, J=13 Hz, C-4'), 63.10 (d., J=162 Hz, OC$H_2$P), 61.98 (d, J=6 Hz, POC$H_2$), 55.71 (C-1'), 31.92 (C-5'), 26.92 (t Bu) and 16.33 (d, Hz POC$H_2$C$H_3$). MS (FAB): 548 (MH$^+$) [α]$^{20}_D$: −15.9 (c=0.63, CHCl$_3$).

EXAMPLE CCCC (+)-9-[(1R,1S)-4-β-(Diethylphosphonomethoxy)-2-β-fluoro-3-α-hydroxycyclopentan-1-β-yl]adenine The 2,3-cyclic sulfate ester of (+)-$N^6$-pivaloyl-9-[(1R,1S)-4-β-(diethylphosphonomethoxy)-2,3-α,α-(dihydroxy)cyclopentan-1-β-yl]adenine (3.06 g, 5.59 mmol), Example BBBB, was treated with tetra-n-butylammonium fluoride (2.19 g, 8.38 mmol) in acetone (50 mL) and then with 1N HCl solution (75 mL) as in Example XX to afford 1.60 g of the desired product contaminated with a small amount of tetrabutylammonium fluoride (approx. yield =70%). NMR data was the same as that obtained for the product of Example XX.

EXAMPLE DDDD (+)-9-[(1R,1S)-4-β-(Dihydroxyphosphonomethoxy)-2-β-fluoro-3-α-hydroxycyclopentan-1-β-yl]adenine A solution of (+)-9-[(1R,1S)-4-β-(diethylphosphonomethoxy)-2-β-fluoro-3-α-hydroxycyclopentan-1-β-yl]adenine (0.30 g, 0.74 mmol), Example CCCC, in anhydrous DMF (6 mL) was treated with bromotrimethylsilane (1.14 g, 7.40 mmol) at room temperature under argon. After 14 hr., the reaction mixture was concentrated in vacuo. The residue was concentrated from DMF (20 mL) and $H_2O$ (20 mL), and then treated with $H_2O$ (10 mL) and conc. $NH_4OH$ (10 mL). The resulting solution was concentrated in vacuo to provide 0.50 g of an off-white solid. Purification by column chromatography on $C_{18}$ adsorbent (40:1, elution with $H_2O$) gave a white solid which was dissolved in $H_2O$ (1 mL) and then treated with acetone (50 mL). The resulting slurry was stirred at room temperature for 18 hr., and the precipitate was collected by filtration and dried in vacuo to give 0.18 g (65%) of the desired product. Analysis: $C_{11}H_{15}N_5O_5PF$: (calc'd): C: 35.78, H: 4.91, N: 20.86. (found): C: 35.71, H: 5.00, N: 21.05. NMR data observed was the same as that for the product of Example YY. $[\alpha]^{20}_D$: +72.0 (c=0.66, $H_2O$).

EXAMPLE EEEE (+)-9-[(1R,1S)-4-β-(Diethylphosphonomethoxy)-2-β-fluorocyclopentan-1-β-yl]adenine (+)-9-[(1R,1S)-4-β-(Diethylphosphonomethoxy)-2-β-fluoro-3-α-hydroxycyclopentan-1-β-yl]adenine (1.19 g, 2.95 mmol), Example CCCC, was dissolved in anhydrous DMF (20 mL) and treated with 1,1'-thiocarbonyldiimidazole (0.88 g, 90%, 4.43 mmol). The reaction mixture was stirred at 80° C. under argon for 2 hr., and then additional 1,1'-thiocarbonyldiimidazole (0.18 g, 90%, 0.91 mmol) was added. After 2 hr. further, the mixture was allowed to cool to room temperature and was concentrated in vacuo. The residue was dissolved in anhydrous 1,4-dioxane (50 mL) and treated with AIBN (0.005 g), bis(tributyltin)oxide (7.03 g, 7.0 mL, 11.8 mmol), and polymethylhydrosiloxane (7.0 mL). The resulting yellow solution was heated at reflux for 3 hr. and at room temperature for 15 hr., and then concentrated in vacuo. The residue was dissolved in methanol (100 mL) and washed with hexane (2×50 mL). Concentration of the methanolic solution gave 2.81 g of a semi-solid residue. Purification by column chromatography on silica gel (20:1, gradient elution with 10% to 18% MeOH/EtOAc) provided 0.526 g (46%) of the product as a pale yellow solid.

Analysis: $C_{15}H_{23}N_5O_4PF$: (calc'd): C: 46.51, H: 5.98, N: 18.08. (found): C: 46.47, H: 5.92, N: 17.92. $^1H$ NMR (300 MHz, DMSO-$d_6$): 8.21 (d, J=1.8 Hz, 1H, H-8), 8.13 (s, 1H, H-2), 7.25 (br s, 2H, $NH_2$), 5.14 (ddd, J=4,4,55 Hz, 1H, H-2'), 4.96 (dm, J=28 Hz, 1H, H-1'), 4.17–4.29 (m, 1H, H-4'), 4.06 (apparent quintet, J=7 Hz, 4H, 2×POCH$_2$), 3.83 (d, J=9 Hz, 2H, OCH$_2$P), 2.66 (ddd, J=7,7,14 Hz, 1H, H-5'a), 2.32–2.55 (m, 2H, H-5'b and H-3'), 2.03 (ddd, J=3,16,27 Hz, 1H, H-3'), and 1.24 (t, J=7 Hz, 6H, 2×POCH$_2$CH$_3$). $^{13}C$ NMR (75 MHz, DMSO-$d_6$): 156.52 (C-6), 156.94 (C-2), 150.09 (C-4), 140.30 (C-8), 118.8 (C-5), 92.94 (d, J=182 Hz, C-2'), 78.31 (d, J=14 Hz, C-4'), 62.55 (d, J=165 Hz, OCH$_2$P), 61.98 (d, J=5 Hz, POCH$_2$), 54.90 (d, J=18 Hz, C-1'), 37.04 (d, J=20 Hz, C-3'), 34.03 (C-5'), and 16.34 (d, J=6 Hz, POCH$_2$CH$_3$) MS (FAB): 388 (MH$^+$) $[\alpha]^{20}_D$: +60.1 (c=0.99, MeOH).

EXAMPLE FFFF (+)-9-[(1R,1S)-4-β-(Dihydroxyphosphonomethoxy)-2-β-fluorocyclopentan-1-β-yl]adenine A solution of (+)-9-[4-β-(diethylphosphonomethoxy)-2-β-fluorocyclopentan-1-β-yl]adenine (0.424 g, 1.09 mmol), Example EEEE, in anhydrous DMF (8 mL) at room temperature under argon was treated dropwise via syringe with bromotrimethylsilane (1.68 g, 10.9 mmol). After 14 hr., the reaction mixture was concentrated in vacuo. The residue was concentrated further from DMF (20 mL) and $H_2O$ (20 mL), then dissolved in $H_2O$ (10 mL) and treated with conc. $NH_4OH$ (10 mL). The resulting solution was concentrated in vacuo to give 0.45 g of an off-white solid which was purified by column chromatography on $C_{18}$ adsorbent (40:1, elution with $H_2O$). Fractions containing the product were pooled and concentrated to 1 mL volume. The solution was then treated with acetone (50 mL), and the resulting slurry was stirred for 2 hr. The precipitate was collected by filtration to provide 0.309 g (81%) of the product as a white solid.

Analysis: $C_{11}H_{15}N_5O_4PF \cdot 0.75\ NH_3$: (calc'd): C: 38.40, H: 5.05, N: 23.41. (found): C: 38.04, H: 5.11, N: 23.15.

$^1H$ NMR (300 MHz, D$_2$O): 8.28 (d, J=2 Hz, 1H, H-8), 8.12 (s, 1H, H-2), 5.16 (dt, J=4.54 Ha, 1H, H-2;), 4.66–4.91 (m, 1H, H-1'), 4.32–4.39 (m, 1H, H-4'), 3.64 (d, J=9 Hz, 2H, OCH$_2$P), 2.79 (ddd, J=7, 7, 14 Hz, 1H, H-5'a), and. 2.14–2.56 (m, 3H, H-5'b) and 2×H-3'). $^{13}C$ NMR (75 MHz, D$_2$O): 157.70 (C-6), 154.47 (C-2), 151.65 (C-4), 144.48 (C-8), 120.79 (C-5), 96.20 (d, J=180 Hz, C-2'), 81.08 (d, J=4 Hz, C-4'), 67.98 (d, J=157 Hz, OCH$_2$P), 58.41 (d, J=18 Hz, C-1'), 39.60 (d, J=20 Hz, C-3'), and 36.97 (C-5'). MS (FAB/GLY): 332 (MH$^+$). $[\alpha]^{20}_D$: +80.9 (c=0.15, H$_2$O).

As one skilled in the art will appreciate, the specific Examples of the enantiomeric compounds of the invention are in the "natural" (1R,4S) configuration. The enantiomeric "unnatural" (1S,4R) configuration derivatives also can be prepared in a manner analogous to that provided for the compounds of the natural configuration except that the starting "cyclopentyl" reactant will be in the unnatural (1S,4R) rather than natural (1R,4S) configuration.

Table I provides a comparison of the observed specific rotations for the (1R,4S) and (1S,4R) compounds prepared according to the procedures in the noted Examples.

TABLE I

| SPECIFIC ROTATIONS OF ENANTIOMERIC COMPOUNDS | | |
|---|---|---|
| Structure of Example | Configuration | $[\alpha]_D^{20}$ |
| AAA | 1R, 4S | +3.25 (c = 0.80, CHCl$_3$) |
|  | 1S, 4R | −1.33 (c = 1.57, CHCl$_3$) |
| BBB | 1R, 4S | −20.7 (c = 1.64, MeOH) |
|  | 1S, 4R | +24.6 (c = 1.12, MeOH) |
| CCC | 1R, 4S | +27.5 (c = 1.14, MeOH) |
|  | 1S, 4R | −28.3 (c = 0.72, MeOH) |
| DDD | 1R, 4S | +4.15 (c = 1.47, H$_2$O) |
|  | 1S, 4R | −3.09 (c = 0.68, H$_2$O) |
| GGG | 1R, 4S | −36.9 (c = 0.47, MeOH); |
|  |  | −40.2 (c = 0.60, MeOH) |
|  | 1S, 4R | +36.9 (c = 1.11, MeOH) |
| HHH | 1R, 4S | −15.7 (c = 1.02, MeOH) |
|  | 1S, 4R | +16.17 (c = 0.94, MeOH) |
| III | 1R, 4S | −2.1 (c = .42, MeOH); |
|  |  | −2.4 (c = 0.88, MeOH) |
|  | 1S, 4R | +2.6 (c = 0.87, MeOH) |
| JJJ | 1R, 4S | −20.4 (c = 0.20, H$_2$O); |
|  |  | −14.4 (c = 0.88, H$_2$O) |
|  | 1S, 4R | +20.2 (c = 0.56, H$_2$O) |
| KKK | 1R, 4S | −26.3 (c = 1.22, MeOH) |
| LLL | 1R, 4S | −0.43 (c = 0.94, MeOH) |
| MMM | 1R, 4S | +14.6 (c = 1.04, MeOH) |
| NNN | 1R, 4S | −2.67 (c = 0.60, MeOH) |
| PPP | 1R, 4S | +11.7 (c = 0.18, H$_2$O) |
| RRR | 1R, 4S | −33 (c = 0.56, MeOH) |
|  | 1S, 4R | +31.8 (c = 1.03, MeOH) |

TABLE I-continued

SPECIFIC ROTATIONS OF ENANTIOMERIC COMPOUNDS

| Structure of Example | Configuration | $[\alpha]_D^{20}$ | |
|---|---|---|---|
| SSS | 1R, 4S | −23.5 | (c = 0.22, MeOH) |
| | 1S, 4R | +24.7 | (c = 0.28, MeOH) |
| TTT (ammonium salt) | 1R, 4S | +0.45 | (c = 0.44, H$_2$O) |
| | 1S, 4R | +14.2 | (c = 0.46, H$_2$O) |
| UUU | 1R, 4S | −78.3 | (c = 2.07, CHCl$_3$) |
| | 1S, 4R | +63.5 | (c = 1.05, MeOH) |
| VVV | 1R, 4S | +50.60 | (c = 0.59, MeOH) |
| | 1S, 4R | −48.0 | (c = 0.76, MeOH) |
| WWW | 1R, 4S | +66.2 | (c = 0.62, H$_2$O) |
| | 1S, 4R | −68.6 | (c = 0.79, H$_2$O) |
| XXX | 1R, 4S | +30.5 | (c = 1.46, MeOH) |
| | 1S, 4R | −33.8 | (c = 1.39, MeOH) |
| YYY | 1R, 4S | +15.53 | (c = 0.76, H$_2$O) |
| | 1S, 4R | −11.65 | (c = 1.55, H$_2$O) |
| ZZ | 1R, 4S | +37.5 | (c = 0.79, CHCl$_3$) |
| | 1S, 4R | −37.1 | (c = 1.47, CHCl$_3$) |

BIOLOGICAL ACTIVITIES

The antiviral activity of compounds of the invention, against both herpes viruses and human immunodeficiency virus (HIV), are presented in Table II. In Table II, the numbers in parenthesis in the columns reporting HIV activity represent the TD$_{50}$, that is, the dosage at which toxic effects are observed in 50% of the population of cells tested.

In Vitro Antiviral Activity

A. HSV-1, HSV-2 and HCMV Assays

The compounds were evaluated for antiviral activity in vitro by a standard plaque reduction assay. Experiments were conducted with vero cells (African Green Monkey Kidney cells) infected with herpes simplex virus Type 1 (HSV-1) [BW$^s$ strain, C. D. Sibrack, et al., *Infect. Disc.*, 1982, 146, 673] and herpes simplex virus Type 2 (HSV-2) [G strain, obtained from American Tissue Culture Collection, Rockville, Md.] and with MRC-5 cells (human embryonic lung (diploid) cells) infected with human cytomegalovirus (HCMV) [AD169 strain, obtained from American Tissue Culture Collection, Rockville, Md].

Briefly, confluent cell monolayers in 24-well plates were infected with 3–50 plaque-forming units of virus in 100 μl of phosphate-buffered saline. After a 1 hour adsorption period, residual inoculum was replaced with 1 mL of the appropriate dilution of the test compound which had been freshly prepared in Eagle's minimal essential medium ("EMEM") containing 10% fetal bovine serum. After a 48 hour incubation period at 37° C. in a 5% CO$_2$ atmosphere, cell monolayers were fixed and stained with Carbol fuchsin and plaques were counted. The antiviral potency of the compound was determined by IC$_{50}$, the inhibitory concentration necessary to reduce the number of plaques by 50% of those in the virus control cultures.

B. Human Immunodeficiency Virus (HIV) Assays

I. HIV antiviral Assay (MT-4 cells)

Compounds were evaluated for activity against human immunodeficiency virus (LAV$_{BRU}$ strain obtained from Luc Montagnier, Institut Pasteur, Paris, France) in MT-4 cells (S. Harada, et al., in *Science*, 1985, 229, 563–566) using the XTT assay described by O. S. Weislow, et al., in *J. Natl. Cancer Instit.*, 1989, 81, 577–586. MT-4 cells were obtained from Doug Richman at the University of California at San Diego. Cells were exposed to HIV and cultured in microtiter plates in the presence of test compounds at concentrations of 0.0013, 0.0064, 0.032, 0.16, 0.8, 4, 20, 100, and 500 μM. On day 7 post-infection, the antiviral effect was measured using the XTT assay in which an optical density (OD) reading is obtained at each drug concentration. The optical density reading is proportional to the number of viable cells.

II. HIV antiviral assay (MT-2 cells)

Suspensions of MT-2 cells (S. Harada, et al., *Science*, 229, 563 (1985) were infected at a multiplicity of infection of 0.03 TCID$_{50}$/cell with HIV (strain HTLV-IIIB). After adsorption for 1–2 hours at 37° C., infected cells were diluted in growth medium (RPMI 1640 containing the antibiotics penicillin plus streptomycin and 10% fetal calf serum) to give a final cell concentration of 1×10$^4$ viable cells/culture well in the presence of serial dilutions of the test compound, starting at 100 μg/ml. Triplicate samples at each drug concentration were used. Cultures of uninfected MT-2 cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% CO$_2$. Following incubation, viable cell numbers were counted in each well using a colorimetric assay following incubation of cells with XTT-PMS solution (XTT tetrazolium reagent plus phenazine methosulfate PMS).

III. HIV antiviral assay (CEM cells)

Suspensions of CEM cells (Nara and Fischinger, Nature, 332:469,1988) cells were infected at a multiplicity of infection (e.g. virus/cell) of 0.12 with HIV (strain HTLV-III B). After adsorption for 1–2 hours at 37° C., infected cells were diluted in growth medium (RPMI 1640 containing the antibiotics penicillin plus streptomycin and 10% fetal calf serum) to give a final cell concentration of 1×10$^4$ viable cells/culture well in the presence of serial dilutions of the test compound, starting at 100 μg/ml. Triplicate samples at each drug concentration were used. Cultures of uninfected CEM cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% CO$_2$. Following incubation, viable cell numbers were counted in each well using a colorimetric assay following incubation of cells with XTT-PMS solution (XTT tetrazolium reagent plus phenazine methosulfate PMS).

For either the CEM or MT-2 infected cells, the percent reduction of viral cytopathic effect (CPE) in drug treated compared to untreated virus infected cells, and percent reduction of cell viability in drug treated uninfected cells compared to untreated controls were calculated and plotted versus the drug concentrations tested. From these plots, the ID$_{50}$ (the minimum drug concentration that inhibits CPE by 50%) for each drug was calculated 2',3'-dideoxycytidine and 3'-azido-3'-deoxythymidine were used as positive controls.

C. MuLV Assays

The compounds were evaluated for antiviral activity against Murine leukemia virus (MuLV) strains using the UV-XC plaque assay (Rowe, et. al., *Virology*, 42:1136, 1970).

The MuLV strains were grown in fetal mouse cells, (SC-1) and used for antiviral tests using the UV-XC plaque assay. Briefly, SC-1 cells are grown as monolayers in 4-well tissue culture plates and inoculated with approximately 50–100 plaque forming units of MuLV in 0.5 ml of 5% EMEM containing 20 μg/ml DEAE/Dextran. After 1 hr. adsorption, the inoculum is removed and 5 ml of 5% EMEM containing three-fold dilutions of the appropriate drug are added. Five days later, the cultures are UV-irradiated with an ultraviolet lamp and rat XC sarcoma cells are added to the cultures. Three to four days after UV-irradiation, the cell cultures are stained with Giemsa stain and the plaques are counted. Antiviral activity is expressed in terms of the reduction in the mean number of UV-XC plaques counted in the drug treated, virus-infected cultures compared with mean number of plaques counted in untreated, virus-infected control cultures. IC$_{50}$ values are calculated by determining the concentration of compound necessary to reduce the number of plaques by 50% compared to those in the virus control cultures.

TABLE II

IN VITRO ANTIVIRAL ACTIVITY (μg/ml) - RACEMIC SERIES

| Compound* | HSV-1 | HSV-2 | HCMV | MuLV | CEM* | MT-2* | HIV MT-4 (μM)* |
|---|---|---|---|---|---|---|---|
| 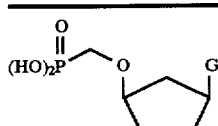 | 13.5 | >50 | >100 | 5.1 | 66, (>100) | 60, (>100) | — |
| 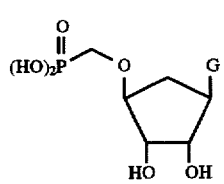 | >100 | >100 | 4.5 | >100 | — | — | >100, (>100) |
| 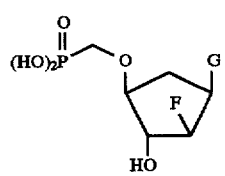 | — | 22 | 0.36 | — | — | — | >500, (>500) |
| 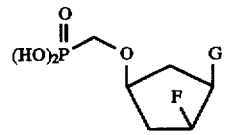 | — | — | — | — | — | — | >100, (>100) |
| 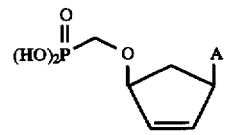 | >116 | >82 | >100 | 0.84 | — | — | 55, (>100) |
| 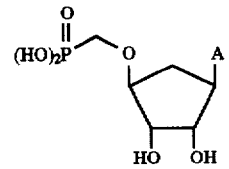 | — | >100 | >100 | >100 | — | — | — |
| 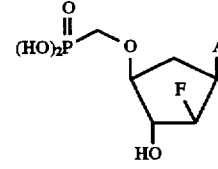 | — | >100 | 85 | — | — | — | — |
| 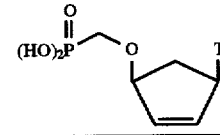 | >140 | >134 | — | — | — | — | 58, (>100) |

*G = guanine; A = adenine; T = thymine; Dosages in parenthesis represent the observed TD$_{50}$.

Additional assays were performed in cell culture systems to determine the concentrations of compounds that are effective in preventing several kinds of viral infections. The assays are described below, and the results are presented in Tables III and IV. In Tables III and IV, the anti-HIV results using CEM cells were obtained using the same protocol described earlier. Figures in parenthesis represent the observed $TD_{50}$ in the HIV screens indicated. Abbreviations: HSV-1 (herpes simplex virus type 1, strain Schooler), HSV-2 (herpes simplex virus type 2, strain 186), VZV (varicella zoster virus, strain ELLEN), HCMV (human cytomegalovirus, strain AD 169 HIV (human immunodeficiency virus, strain HTLV-IIIB).

Cell Culture Assays

HSV-1, HSV-2, HCMV and VZV antiviral assays

Virus was adsorbed to WI-38 cell culture monolayers in 6 well culture plates (Costar, Cambridge, Mass.) for 1 hour prior to addition of maintenance medium containing duplicate dilutions of the test compound. Inhibition of plaque development was evaluated on fixed and stained monolayers after 4 days incubation at 37° C. for HSV-1 and HSV-2, and after 5–7 days incubation at 37° C. for HCMV and VZV. $ID_{50}$ values were determined from the drug concentration which conferred at least a 50% plaque reduction compared to virus controls.

HIV antiviral assay (MT-2 cells)

Suspensions of MT-2 cells (S. Harada, et al., Science, 229, 563 (1985)) were infected at a multiplicity of infection of 0.03 $TCID_{50}$/cell with HIV (strain HTLV-III B). After adsorption of 1–2 hours at 37° C., infected cells were diluted in growth medium (RPMI 1640 containing the antibiotics penicillin plus streptomycin and 10% fetal calf serum) to give a final cell concentration of $1\times10^4$ viable cells/culture well in the presence of serial dilutions of the test compound, starting at 100 µg/ml. Triplicate samples at each drug concentration were used. Cultures of uninfected MT-2 cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate PMS).

TABLE III

IN VITRO ANTIVIRAL ACTIVITY (µg/ml) - RACEMIC SERIES

| Compound* | HSV-1 | HSV-2 | HCMV | VZV | HIV* (CEM Cells) |
|---|---|---|---|---|---|
| (HO)₂P(O)—O—[ring]—G | >72 | >72 | >100 | 12–121 | — |
| (HO)₂P(O)—O—[ring with F]—G | 10–25 | 10–25 | 10–25 | 10–33 | >100, (>100) |
| (HO)₂P(O)—O—[ring]—A | >100 | >100 | >100 | >100 | — |

*G = guanine; A = adenine; Dosages in parenthesis represent the observed $TD_{50}$.

TABLE IV

IN VITRO ANTIVIRAL DATA (µg/ml) - ENANTIOMERIC SERIES

| Compound* | Configuration | Virus | | | | HIV* | |
|---|---|---|---|---|---|---|---|
| | | HSV-1 | HSV-2 | HCMV | VZV | CEM | MT-2 |
| (HO)₂P(O)—O—[ring]—G | (1R, 4S) | 100 | >120 | 199 | 36–59 | 26, (>100) >100, (>100) | 20, (>100) >100, (>100) |
| | (1S, 4R) | >111 | >111 | >111 | >111 | | |

TABLE IV-continued

IN VITRO ANTIVIRAL DATA (μg/ml) - ENANTIOMERIC SERIES

| Compound* | Configuration | Virus | | | | HIV* | |
| --- | --- | --- | --- | --- | --- | --- | --- |
| | | HSV-1 | HSV-2 | HCMV | VZV | CEM | MT-2 |
| (HO)$_2$P(O)-CH$_2$-O-cyclopentane-G (HO, OH) | (1R, 4S) (1S, 4R) | >100 >100$^T$ | >100 >100$^T$ | 10-25 — | 25-50 >100$^T$ | — — | — — |
| (HO)$_2$P(O)-CH$_2$-O-cyclopentane-G (F, HO) | (1R, 4S) (1S, 4R) | 0.2-0.5 >100$^{N.T.}$ | 0.2-0.5 >100$^{N.T.}$ | 0.2-0.5 — | 0.05-0.1 >100$^{N.T.}$ | — — | — — |
| (HO)$_2$P(O)-CH$_2$-O-cyclopentane-G (HO) | (1R, 4S) | 2-5 | 5-10 | 2-5 | 2 | — | — |
| (HO)$_2$P(O)-CH$_2$-O-cyclopentene-A | (1R, 4S) (1S, 4R) | >100 >100 | >100 >100 | >100 >100 | >100 >100 | — — | — — |
| (HO)$_2$P(O)-CH$_2$-O-cyclopentane-A (F, HO) | (1R, 4S) | 10-25 | 10-25 | >100 | 5-10 | — | — |
| (HO)$_2$P(O)-CH$_2$-O-cyclopentane-A (F) | (1R, 4S) | >100$^T$ (Toxic 10-100) | >100$^T$ (Toxic 10-100) | — | 1-10 (Toxic 10-100) | >100 (>100) | >100, (20) |
| (HO)$_2$P(O)-CH$_2$-O-cyclopentene-T | (1R, 4S) (1S, 4R) | >100 >100 | >100 >100 | >100 >100 | >100 >100 | >100, (>100) >100, (>100) | >100, (>100) >100, (>100) |

*G = guanine; A = adenine; T = thymine; Dosages in parenthesis represent the observed TD$_{50}$.
T = Toxic
N.T. = Not Toxic

We claim:

1. A compound of the Formula I or Formula II

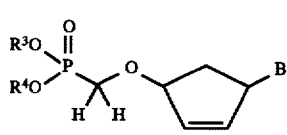

I

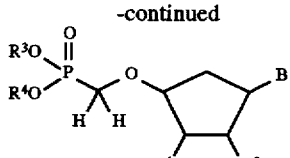

II wherein
R$^1$ and R$^2$ are independently hydrogen, hydroxy, chlorine, fluorine, bromine, or an organic substituent having 1 to 5 carbon atoms and selected from acyloxy having a hydrocarbon stem of 1 to 4 carbon atoms, alkoxy, alkylthio, amino alkylamino and dialkylamino;

$R^3$ and $R^4$ are independently hydrogen, or organic phosphonic ester substituents having 1 to 12 carbon atoms and selected from alkyl, alkenyl, aryl, and aralkyl; and B is a heterocyclic group selected from the group consisting of pyrimidine, purine, triazine, deazapurine, and triazole, attached through a ring nitrogen atom thereof optionally substituted with 1 to 3 substituents selected from the group consisting of hydroxy, mercapto, amino, hydrazino, fluoro, chloro, bromo, iodo, $C_1$ to $C_3$ alkyl, C2–C3 alkenyl, C2–C3 haloalkenyl, C1–C3 alkoxy, and C1–C3 alkylthio;

and the pharmaceutically acceptable acid addition, metal, and amine salts thereof.

2. The compound of claim 1 wherein B is a heterocyclic group selected from the group consisting of pyrimidine, purine, and deazapurine, optionally substituted with 1 to 3 substituents selected from the group consisting of hydroxy, mercapto, amino, hydrazino, fluoro, chloro, bromo, iodo, $C_1$ to $C_3$ alkyl, C2–C3 alkenyl, C2–C3 haloalkenyl, C1–C3 alkoxy, and C1–C3 alkylthio.

3. The compound of claim 1 wherein B is a purine, optionally substituted with 1 to 3 substituents selected from the group consisting of hydroxy, mercapto, amino, hydrazino, fluoro, chloro, bromo, iodo, $C_1$ to $C_3$ alkyl, C2–C3 alkenyl, C2–C3 haloalkenyl, C1–C3 alkoxy, and C1–C3 alkylthio.

4. The compound of claim 1 wherein B is selected from the group consisting of adenine, guanine, and thymine.

5. The compound of claim 1 wherein B is adenine.

6. The compound of claim 1 wherein B is guanine.

7. The compound of claim 1 wherein B is selected from the groups consisting of 8-bromoguanine, 8-chloroguanine, 8-aminoguanine, 8-hydrazinoguanine, 8-hydroxyguanine, 8-methylguanine, 8-mercaptoguanine, 3-deazaguanine, 2-aminopurine, 2,6-diaminopurine, cytosine, 5-ethylcytosine, 5-methylcytosine, thymine, uracil, 5-chlorouracil, 5-bromouracil, 5-ethyluracil, 5-iodouracil, 5-propyluracil, 5-vinyluracil, adenine, and 3-deazaadenine.

8. The compound of claim 1 having formula I and a configuration selected from the group consisting of (1R,4S), and (1S,4R) or having formula II and a configuration selected from the group consisting of (1R,3S), and (1S,3R).

9. The compound of claim 8 having formula I and the configuration (1R,4S) or having formula II and the configuration (1R,3S).

10. A compound of the formula:

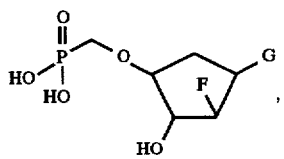

wherein G is guanine attached through a ring nitrogen atom thereof.

11. The compound of claim 10 having the configuration (1R,4S).

12. A compound selected from the group consisting of:

1-[(1β,4β)-4-(dihydroxyphosphonyl)methoxycyclopent-2-en-1-yl]thymine,
1-[(1β,4β)-4-(dihydroxyphosphonyl)methoxycyclopent-2-en-1-yl]cytosine,
9-[(1β,4β)-4-(diethoxyphosphonyl)methoxycyclopent-2-en-1-yl]adenine,
9-[(1β,4β)-4-(ethoxyhydroxyphosphonyl)methoxycyclopent-2-en-1-yl]adenine,
9-[(1β,4β)-4-(dihydroxyphosphonyl)methoxycyclopent-2-en-1-yl]adenine,
9-[(1β,[4]3β)-[4]3-(diethoxyphosphonyl)methoxycyclopentan-1-yl]adenine, and
9-[(1β,[4]3β)-[4]3-(dihydroxyphosphonyl)methoxycyclopentan-1-yl]adenine.

13. A compound selected from the group consisting of:

(±)-1-(4-β-diethylphosphonylmethoxycyclopent-2-ene-1-β-yl)-$N^3$-(2-(trimethylsilyl)-ethoxymethyl)thymine,
(±)-1-(4-β-phosphonylmethoxycyclopent-2-ene-1-β-yl)-$N^3$-(2-(trimethylsilyl)ethoxymethyl)thymine,
(±)-1-(4-β-phosphonylmethoxycyclopent-2-ene-1-β-yl)thymine,
(±)-1-(4-β-phosphonylmethoxycyclopent-2-ene-1-β-yl)-$N^3$-(hydroxymethyl)thymine,
(±)-1-(4-β-diethylphosphonylmethoxycyclopent-2-ene-1-β-yl)-$N^4$-(dimethylaminomethylidene)cytosine,
(±)-1-(4-β-phosphonylmethoxycyclopent-2-ene-1-β-yl)cytosine,
(±)-9-(4-β-diethylphosphonylmethoxycyclopent-2-ene-1-β-yl)adenine,
(±)-9-(4-diethylphosphonylmethoxycyclopent-2-ene-1-β-yl)adenine,
(±)-9-(4-β-monoethylphosphonylmethoxycyclopent-2-ene-1-β-yl)adenine,
(±)-9-(4-β-phosphonylmethoxycyclopent-2-ene-1-β-yl)adenine,
(±)-9-([4]3-β-diethylphosphonylmethoxycyclopentan-1-β-yl)adenine,
(±)-9-([4]3-β-phosphonylmethoxycyclopentan-1-β-yl)adenine,
(±)-$N^2$-monomethoxytrityl-6-O-benzyl-9-(4-β-diethylphosphonylmethoxycyclopent-2-ene-1-β-yl)guanine,
(±)-9-(4-β-diethylphosphonylmethoxycyclopent-2-ene-1-β-yl)guanine, and
(±)-9-(4-β-dihydroxyphosphonylmethoxycyclopent-2-ene-1-β-yl)guanine.

14. A compound of the Formula I or Formula II

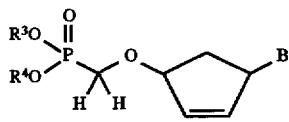

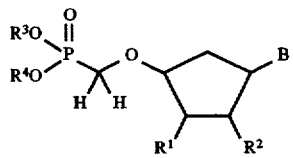

wherein $R^1$ and $R^2$ are independently hydrogen, hydroxy, chlorine, fluorine, bromine, or an organic substituent having 1 to 5 carbon atoms and selected from acyloxy having a hydrocarbon stem of 1 to 4 carbon atoms, alkoxy, alkylthio, amino, alkylamino and dialkylamino;

R³ and R⁴ are independently hydrogen, or organic phosphonic ester substituents having 1 to 12 carbon atoms and selected from alkyl, alkenyl, aryl, and aralkyl;

B is selected from the group consisting of

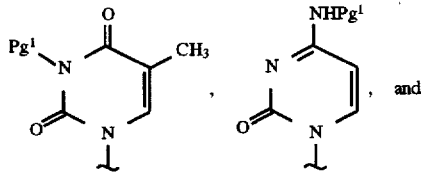

-continued

Pg¹ is an amino protecting group;
Pg² is a hydroxy protecting group; and with the proviso that said Pg¹ and Pg² groups are capable of protecting amino and hydroxy groups, respectively, from reaction with tetrakis(triphenylphosphine)palladium (0) in DMF/THF.

* * * * *